United States Patent
Viet et al.

(10) Patent No.: US 10,981,879 B2
(45) Date of Patent: Apr. 20, 2021

(54) THIOETHER TRIAZOLOPYRIDINE AND TRIAZOLOPYRIMIDINE INHIBITORS OF MYELOPEROXIDASE

(71) Applicant: BRISTOL-MYERS SQUIBB COMPANY, Princeton, NJ (US)

(72) Inventors: Andrew Quoc Viet, Schwenksville, PA (US); Nicholas R. Wurtz, Pennington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 86 days.

(21) Appl. No.: 16/145,345

(22) Filed: Sep. 28, 2018

(65) Prior Publication Data

US 2019/0031623 A1    Jan. 31, 2019

Related U.S. Application Data

(63) Continuation of application No. 15/510,150, filed as application No. PCT/US2015/049095 on Sep. 9, 2015, now abandoned.

(60) Provisional application No. 62/048,857, filed on Sep. 11, 2014.

(51) Int. Cl.
| | |
|---|---|
| *C07D 249/18* | (2006.01) |
| *C07D 249/16* | (2006.01) |
| *C07D 471/04* | (2006.01) |
| *C07D 487/04* | (2006.01) |
| *A61K 31/437* | (2006.01) |
| *A61K 31/7064* | (2006.01) |

(52) U.S. Cl.
CPC .......... *C07D 249/16* (2013.01); *A61K 31/437* (2013.01); *A61K 31/7064* (2013.01); *C07D 471/04* (2013.01); *C07D 487/04* (2013.01)

(58) Field of Classification Search
CPC .................................................. C07D 249/18
See application file for complete search history.

(56) References Cited

FOREIGN PATENT DOCUMENTS

| | | | |
|---|---|---|---|
| WO | WO-9604281 A1 * | 2/1996 | ........... C07D 239/47 |
| WO | WO 2007/120098 A1 | 10/2007 | |

OTHER PUBLICATIONS

Silverman, R.B. "The Organic Chemistry of Drug Design and Drug Action." 2d ed. (2004) (Year: 2004).*
Robins, R.K., "Antitumor Activity and Structural Relationships of Purine Derivatives and Related Compounds against Neoplasms in Experimental Animals," Journal of Medicinal Chemistry, vol. 7, No. 2, pp. 186-199 (1964).
Shealy, Y. Fulmer et al., "v-Triazolo[4,5-d]pyrimidines. I. Synthesis and Nucleophilic Substitution of 7-Chloro Derivatives of 3-Substituted v-Triazolo[4,5-d]pyrimidines," Journal of Organic Chemistry, vol. 26, No. 11, pp. 4433-4400 (1961).

* cited by examiner

*Primary Examiner* — John S Kenyon
(74) *Attorney, Agent, or Firm* — Elliott Korsen; Shrikant Kulkarni

(57) ABSTRACT

The present invention provides compounds of Formula (I):

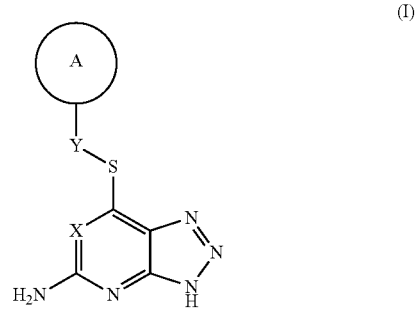

wherein A, X and Y are as defined in the specification, and compositions comprising any of such novel compounds. These compounds are myeloperoxidase (MPO) inhibitors and/or eosinophil peroxidase (EPX) inhibitors, which may be used as medicaments.

5 Claims, No Drawings

THIOETHER TRIAZOLOPYRIDINE AND TRIAZOLOPYRIMIDINE INHIBITORS OF MYELOPEROXIDASE

CROSS-REFERENCE TO RELATED APPLICATIONS

This application is a continuation of U.S. application Ser. No. 15/510,150 filed Mar. 9, 2017, which is the 371 National Stage of International Application No. PCT/US15/49095 filed Sep. 9, 2015, which claims the benefit of U.S. Provisional Application No. 62/048,857 filed Sep. 11, 2014, the disclosures of which are incorporated herein by reference in their entirety.

FIELD OF THE INVENTION

The present invention relates to novel thioether triazolopyridine and triazolopyrimidine compounds, which are myeloperoxidase (MPO) inhibitors and/or eosinophil peroxidase (EPX) inhibitors, compositions containing them, and methods of using them, for example, for the treatment of atherosclerosis, heart failure, chronic obstructive pulmonary disease (COPD), and related diseases.

BACKGROUND OF THE INVENTION

Cardiovascular disease is a major health risk throughout the industrialized world. Atherosclerosis, the most prevalent of cardiovascular diseases, is the principal cause of heart attack and stroke, and thereby the principal cause of death in the United States. Atherosclerosis is a complex disease involving many cell types and molecular factors (for a detailed review, see Weber et al., *Nature Med.*, 17(11):1410-1422 (2011)).

MPO inhibitors have been suggested to reduce the atherosclerotic burden and/or the vulnerability of existing atherosclerotic lesions and thereby decrease the risk of acute myocardial infarction, unstable angina or stroke, and reduce ischemia-reperfusion injury during acute coronary syndrome and ischemic cerebrovascular events. Several lines of data support a role for MPO in atherosclerosis. MPO is expressed in the shoulder regions and necrotic core of human atherosclerotic lesions and active enzyme has been isolated from autopsy specimens of human lesions (Daugherty, A. et al., *J. Clin. Invest.*, 94(1):437-444 (1994)). Moreover, HOCl-modified lipoproteins have been detected in advanced human atherosclerotic lesions (Hazed, L. J. et al., *J. Clin. Invest.*, 97:1535-1544 (1996)). In eroded and ruptured human lesions, as compared to fatty streaks, an increased number of MPO expressing macrophages have been demonstrated, suggesting a particular role for MPO in acute coronary syndromes (Sugiyama, S. et al., *Am. J. Pathol.* 158(3):879-891 (2001); Tavora, F. R., *BMC Cardiovasc. Disord.*, 9:27 (Jun. 23, 2009)).

Data accumulated during the last fifteen years indicate that the pro-atherogenic actions of MPO include oxidation of lipoproteins, induction of endothelial dysfunction via consuming nitric oxide and destabilization of atherosclerotic lesions by activation of proteases (Nicholls, S. J. et al., *Arterioscler. Thromb. Vasc. Biol.*, 25(6):1102-1111 (2005); Nicholls, S. J. et al., *JLR*, S346-S351 (2009)). Several studies have focused on nitro- and chlorotyrosine modifications of LDL and HDL lipoproteins. Since chlorotyrosine modifications in vivo are generated by hypochlorous acid produced by MPO these modifications are regarded as specific markers of MPO activity (Hazen, S. et al., *J. Clin. Invest.*, 99(9):2075-2081 (1997)).

ApoA-I isolated from atherosclerotic lesions is modified by reactive chlorine and nitrogen species as well as by reactive carbonyls (Pennathur, S. et al., *J. Biol. Chem.*, 279:42977-42983 (2004); Shao, B. et al., *J. Biol. Chem.*, 279:7856-7866 (2004); Zheng, L. et al., *J. Clin. Invest.*, 114(4):529-541 (2004); Shao, B. et al., *JBC in press* (2012)). Chlorotyrosine modification of apoA1, the main apolipoprotein of HDL cholesterol, was associated with impaired cholesterol acceptor function (Bergt, C. S. et al., *Proc. Natl. Acad. Sci. USA*, 101(35):13032-13037 (2004); Zheng, L. et al., *J. Clin. Invest.*, 114(4):529-541 (2004)). Thus, oxidation of apoA-I amino acid residues by the MPO—$H_2O_2$—$Cl^-$ system is one mechanism for loss of its biological activities.

The lipid and protein content of LDL are also targets for MPO oxidation and presence of chlorotyrosine in LDL extracted from human atherosclerotic tissues has been shown (Hazen, S. et al., *J. Clin. Invest.*, 2075-2081 (1997)). LDL particles exposed to MPO in vitro become aggregated, leading to facilitated uptake via macrophage scavenger receptors and foam cell formation (Hazed, L. J. et al., *Biochem. J.*, 290(Pt. 1):165-172 (1993); Podrez, E. A. et al., *J. Clin. Invest.* 105:1095-1108 (2000)). Thus, MPO appears to play a role in the generation of oxidized LDL, which contributes to atherosclerosis plaque development.

Further evidence implicating MPO in the pathophysiology of atherosclerosis comes from the study of hMPO transgenic mice crossed with LDL-R KO mice (Castelini L. W. et al., *J. Lipid Res.*, 47:1366-1377 (2006)). These mice expressed MPO in lesions and developed significantly larger aortic lesions than control LDL-R KO mice.

Many clinical studies have implicated MPO in cardiovascular disease in human patients. Patients with established coronary artery disease have higher plasma and leukocyte MPO levels than healthy controls (Zhang, R. et al., *JAMA*, 286(17):2136-2142 (2001)). Moreover, in three large prospective studies plasma levels of MPO predicted the risk of future coronary events or revascularization (Baldus, S. et al., *Circulation*, 108(12):1440-1445 (2003); Brennan, M. et al., *N Engl. J. Med.*, 349(17):1595-1604 (2003); Kohli, P. et al., *Circulation*, 122:A13175 (2010)). In two recent large nested case control prospective studies, the EPIC-Norfolk and MONICA-/KORA Augsburg studies, baseline MPO levels in these initially healthy populations turned out to be an excellent predictor of future risk of CAD and CHD respectively, showing that this inflammatory marker precedes the presentation of clinical symptoms of CVD (Meuwese, M. C. et al., *J. Am. Coll. Cardiol.*, 50:159-165 (2007); Karakas et al., *J. Int. Med.*, 271:43-50 (2011)). Interestingly, MPO deficient humans are less affected by cardiovascular disease than controls with normal MPO levels (Kutter, D. et al., *Acta Haematol.*, 104:10-15 (2000)). A polymorphism in the MPO promoter affects expression leading to high and low MPO expressing individuals. In three different studies the high expression genotype has been associated with an increased risk of cardiovascular disease (Nikpoor, B. et al., *Am. Heart 1*, 142(2):336-339 (2001); Makela, R. et al., *Lab. Invest.* 83(7):919-925 (2003); Asselbergs, F. W. et al., *Am. J. Med.*, 116(6):429-430 (2004)).

MPO inhibitors are expected to preserve heart function and reduce heart failure burden in patients. In MPO null mice, preservation of left ventricular (LV) function has been observed in both a coronary artery ligation model (Askari, A. T. et al., *J. Exp. Med.*, 197:615-624 (2003)) and an ischemia reperfusion model (Vasilyev, N. et al., *Circulation*, 112:2812-2820 (2005)), suggesting that MPO may provide a mechanistic link between inflammation, oxidant stress, and impaired cardiac remodeling. High circulating levels of MPO have also been linked to chronic heart failure in patients. Systemic MPO was increased in patients with established chronic systolic HF and correlated with diastolic dysfunction independent of age and plasma B-type natriuretic peptide (Tang, W. H. et al., *Am. J. Cardiol.*, 98:796-799 (2006)). Studies also showed that systemic MPO in subjects with myocardial infarction (MI) (Mocatta, T. J. et al., *J. Am. Coll. Cardiol.*, 49:1993-2000 (2007)) or chronic systolic HF (Tang, W. H. et al., *J. Am. Coll. Cardiol.*, 49:2364-2370 (2007)) may predict long-term adverse clinical events.

Inhibitors of MPO or EPX may be used to treat other neuroinflammatory diseases, including multiple sclerosis, Alzheimer's disease, Parkinson's disease, multiple system atrophy, and stroke as well as other inflammatory diseases or conditions like asthma, COPD, cystic fibrosis, inflammatory bowel disease, chronic kidney disease, renal glomerular damage and rheumatoid arthritis.

In these chronic inflammatory diseases, a role of MPO in the development of tissue injury has been suggested. In lesional tissues of patients with Alzheimer's disease, MPO protein was detected along with elevated levels of chlorotyrosine (Green, P. S. et al., *J. Neurochem.*, 90:724-733 (2004)). In an animal model of Parkinson's disease, increased levels of chlorotyrosine and HOCl-modified proteins in brain tissues have been reported (Choi, D. K. et al., *J. Neuroscience*, 25(28):6394-6600 (2005)). In asthmatic patients the level of bromotyrosine, a molecular fingerprint of eosinophil-catalyzed oxidation was associated with symptom severity (Wedes, S. H. et al., *J. Pediatr.*, 248-255 (2011)). Upon allergen challenge, a model that elicits primarily a strong eosinophilic response, lung segments of asthmatic subjects exhibit a >10 fold increase in bronchioalveolar lavage 3-bromotyrosine an indicator of eosinophil activity vs. a 3-fold increase in 3-chlorotyrosine characteristic of MPO activity (Wu, W. et al., *JCI*, 105:1455-1463 (2000)). The presence of HOCl-modified protein was also detected in patients with membranous glomerulonephritis (Grone et al., *Lab. Invest.*, 82:5-14 (2002)). High MPO circulating levels have been implicated in the development of cardiovascular and chronic kidney disease in patients on hemodialysis (Honda, H. et al., *Clin. J. Am. Soc., Nephrol.*, 142-151 (2009). In addition MPO activity and 3-chlorotyrosine levels were also increased during hemodialysis in patients with end-stage renal disease (Delporte, C et al., *Talanta*, 99:603-609 (2012)). Similarly, there is accumulation of neutrophils and eosinophils in conjunction with MPO and EPX seen in intestinal mucosa of patients with inflammatory bowel disease (Kruidenier, L. et al., *J. Pathol.*, 201:17-27 (2003); Carlson, M. et al., *Am. J. Gastrol.*, 94(7):1876-1883 (1999)) and in synovial fluids of rheumatoid arthritis patients (Edwards, S. W. et al., *Biochem. J.*, 250:81-85 (1988); Nucombe, H. L. et al., *Ann. Rheum. Dis.*, 50:237-242 (1991)).

Thus, there is considerable evidence that MPO and/or EPX derived oxidants contribute to tissue injury in chronic inflammatory disorders. MPO and/or EPX inhibitors are anticipated to reduce the levels of oxidants and tissue injury associated with the progression of these diseases.

SUMMARY OF THE INVENTION

The present disclosure provides thioether triazolopyridine and triazolopyrimidine compounds, including stereoisomers, tautomers, pharmaceutically acceptable salts, polymorphs, or solvates thereof, which are useful as MPO inhibitors and/or EPX inhibitors.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, polymorphs, or solvates thereof.

The compounds of the invention may be used in the treatment of diseases or disorders associated with the activity of MPO and/or EPX.

The compounds of the invention may be used in therapy.

The compounds of the invention may be used for the manufacture of a medicament for the treatment of diseases or disorders associated with the activity of MPO and/or EPX.

Examples of diseases or disorders associated with the activity of MPO and/or EPX include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

The compounds of the invention can be used alone, in combination with other compounds of the present invention, or in combination with one or more, preferably one to two other agent(s).

Other features and advantages of the invention will be apparent from the following detailed description and claims.

DETAILED DESCRIPTION OF THE INVENTION

I. Compounds of the Invention

In a first aspect, the present invention provides, inter alia, a compound of Formula (I):

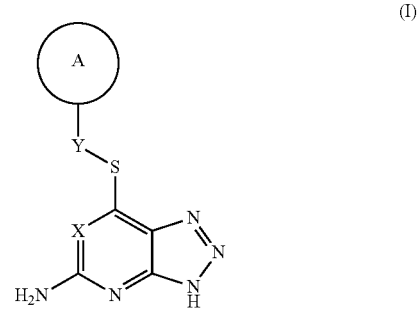

or a stereoisomer, a tautomer, a pharmaceutically acceptable salt, a polymorph, or a solvate thereof, wherein:

ring A is independently phenyl substituted with 0-1 $R^2$ and 0-4 $R^3$, or (a 5- to 6-membered heteroaryl comprising carbon atoms and 1-4 heteroatoms selected from N, $NR^a$, O, and $S(O)_p$, wherein said heterocycle is substituted with 0-1 $R^2$ and 0-3 $R^3$);

X is independently CH or N;

Y is independently selected from: a hydrocarbon linker substituted with 0-1 $R^1$, or a hydrocarbon-heteroatom linker substituted with 0-1 $R^1$; wherein said hydrocarbon linker has one to six carbon atoms and may be straight or branched; and said hydrocarbon-heteroatom linker has one to four carbon atoms and one group selected from O, S, NH, $N(C_{1-4}$ alkyl), CONH, and NHCO;

$R^1$ is independently selected from: CN, OH, —($C_{1-4}$ alkyl substituted with 0-1 $R^{18}$), $C_{1-4}$ haloalkyl, Ph, Bn, COPh, CH(OH)Ph, $CO_2(C_{1-4}$ alkyl), and CONHBn;

$R^2$ is independently selected from: —$CH(NH_2)CF_3$, —$(CH_2)_tOH$, —$O(CH_2)_{2-3}N(C_{1-4}$ alkyl$)_2$, —$(CH_2)_nR^4$, and —$(CH_2)_n(X_1)_n(CH_2)_nR^5$;

$X_1$ is independently selected from: $C(Me)_2$, O, S, CO and $SO_2$;

$R^3$ is, at each occurrence, independently selected from: halogen, CN, $C_{1-4}$ alkyl, $C_{1-4}$ alkoxy, $C_{1-4}$ haloalkyl, $C_{1-4}$ haloalkoxy, $NO_2$, $CONH_2$, and $SO_2(C_{1-4}$ alkyl);

alternatively, $R^2$ and $R^3$, together with the carbon atoms to which they are attached, combine to form a 5- to 6-membered carbocyclic or heterocyclic ring comprising carbon atoms and 0-3 heteroatoms selected from N, $NR^a$, O, and $S(O)_p$; wherein said heterocycle is substituted with 0-2 $R^{19}$;

$R^4$ is independently selected from: halogen, $C_{1-4}$ alkyl, $C_{1-4}$ alkoxy, $C_{1-4}$ alkylthio, $C_{1-4}$ haloalkyl, $C_{1-4}$ haloalkoxy, $C_{1-4}$ haloalkylthio, CN, $CO_2(C_{1-4}$ alkyl), $NO_2$, $NR^6R^7$, $CONR^6R^7$, $COR^{10}$, —$CONH(CH_2)_{1-2}NR^9R^{10}$, $SO_2NR^9R^{10}$, and $S(O)_pR^8$;

$R^5$ is independently selected from: $C_{3-10}$ carbocycle substituted with 0-2 $R^{11}$, phenyl substituted with 0-3 $R^{11}$ and 0-1 $R^{12}$, and 5- to 10-membered heterocycle comprising carbon atoms and 1-4 heteroatoms selected from N, $NR^a$, O, and $S(O)_p$; wherein said heterocycle is substituted with 0-2 $R^{11}$ and 0-1 $R^{13}$;

$R^6$ is, at each occurrence, independently selected from: H, $C_{1-4}$ haloalkyl, $C_{1-6}$ alkyl substituted with 0-2 $R^{15}$, —$(CH_2)_n$—($C_{3-6}$ cycloalkyl substituted with 0-1 $R^{14}$), —$(CH_2)_n$-(phenyl substituted with 0-1 $R^{16}$), —$(CH_2)_n$-(a 5- to 10-membered heterocycle comprising carbon atoms and 1-4 heteroatoms selected from N, $NR^a$, O, and $S(O)_p$, wherein said heterocycle is substituted with 0-1 $R^{17}$);

$R^7$ is, at each occurrence, independently selected from: H and $C_{1-4}$ alkyl substituted with $R^{11}$;

alternatively, $R^6$ and $R^7$, together with the nitrogen atom to which they are attached, combine to form a 4- to 10-membered heterocyclic ring comprising carbon atoms and 1-4 heteroatoms selected from N, $NR^a$, O, and $S(O)_p$; wherein said heterocycle is substituted with 0-1 $R^{17}$;

$R^8$ is, at each occurrence, independently selected from: $C_{1-4}$ alkyl, —$(CH_2)_r$—$C_{3-6}$ cycloalkyl, and —$(CH_2)_r$-phenyl;

$R^9$ is, at each occurrence, independently selected from: H and $C_{1-4}$ alkyl;

$R^{10}$ is, at each occurrence, independently selected from: $R^8$ and H;

$R^{11}$ is, at each occurrence, independently selected from: OH, halogen, $C_{1-4}$ alkoxy, $C_{1-4}$ haloalkyl, and $C_{1-4}$ haloalkoxy;

$R^{12}$ is independently selected from: halogen, CN, $C_{1-4}$ alkyl, $C_{1-4}$ alkoxy, $C_{1-4}$ haloalkyl, $C_{1-4}$ haloalkoxy, $C_{1-4}$ alkylthio, OH, $CH_2OH$, $CO_2H$, $CO_2(C_{1-4}$ alkyl), $NH_2$, $CH_2NH_2$, $N(C_{1-4}$ alkyl$)_2$, $CH_2N(C_{1-4}$ alkyl$)_2$, $CONH_2$, $CONH(C_{1-4}$ alkyl), $CONHCH_2CH_2N(C_{1-4}$ alkyl$)_2$, $CON(C_{1-4}$ alkyl$)_2$, $SO_2NH_2$, $SO_2NH(C_{1-4}$ alkyl), $SO_2N(C_{1-4}$ alkyl$)_2$, CONHPh, NHCOPh, —$(CH_2)_n$—($C_{3-6}$ carbocycle substituted with 0-2 $R^c$), and (a 5- to 6-membered heterocycle comprising carbon atoms and 1-4 heteroatoms selected from N, $NR^a$, O, and $S(O)_p$, wherein said heterocycle is substituted with 0-2 $R^c$);

$R^{13}$ is independently selected from: $R^{12}$ and =O;

$R^{14}$ and $R^{16}$ are, at each occurrence, independently selected from: halogen, $C_{1-4}$ alkyl, $C_{1-4}$ alkoxy, $C_{1-4}$ haloalkyl, $C_{1-4}$ haloalkoxy, OH, $CH_2OH$, $N(C_{1-4}$ alkyl$)_2$, $CONH_2$, $CONH(C_{1-4}$ alkyl), $CON(C_{1-4}$ alkyl$)_2$, $OCH_2CONH_2$, $NHCO(C_{1-4}$ alkyl), $NHCO_2(C_{1-4}$ alkyl), $SO_2(C_{1-4}$ alkyl), —$(CH_2)_n$-phenyl, —O—$(CH_2)_n$-phenyl, and pyridylmethyl;

$R^{15}$ is, at each occurrence, independently selected from: OH, $C_{1-4}$ alkoxy, $C_{1-4}$ haloalkyl, $C_{1-4}$ haloalkoxy, $N(C_{1-4}$ alkyl$)_2$, $CONH_2$, $CONH(C_{1-4}$ alkyl), and $CON(C_{1-4}$ alkyl$)_2$;

$R^{17}$ is independently selected from: $R^{14}$ and =O;

$R^{18}$ is independently selected from: OH, CN, $NH_2$, $N(C_{1-4}$ alkyl$)_2$, NHBn, imidazolyl and morpholinyl;

$R^{19}$ is independently selected from: halogen and $CO_2(C_{1-4}$ alkyl);

$R^a$ is, at each occurrence, independently selected from: H, $C_{1-4}$ alkyl, $CO(C_{1-4}$ alkyl), $CO_2(C_{1-4}$ alkyl), $SO_2(C_{1-4}$ alkyl), —$(CH_2)_n$—$C_{3-6}$ cycloalkyl, —$(CH_2)_n$-(phenyl substituted with 0-2 $R^c$), —CO(—$(CH_2)_n$-phenyl), (a 5- to 6-membered heteroaryl comprising carbon atoms and 1-4 heteroatoms selected from N, $NR^b$, O, and $S(O)_p$, wherein said heterocycle is substituted with 0-2 $R^c$);

$R^b$ is, at each occurrence, independently selected from: H and $C_{1-4}$ alkyl;

$R^c$ is, at each occurrence, independently selected from: OH, CN, $C_{1-4}$ alkyl, halogen, $C_{1-4}$ alkoxy, $C_{1-4}$ haloalkyl, $C_{1-4}$ haloalkoxy, $N(C_{1-4}$ alkyl$)_2$, —$CH_2N(C_{1-4}$ alkyl$)_2$, $CONHCH_2CH_2N(C_{1-4}$ alkyl$)_2$, pyrrolidinyl, piperazinyl, and

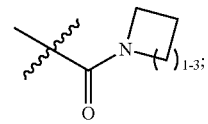

n is, at each occurrence, independently selected from: 0, 1 and 2;

p is, at each occurrence, independently selected from: 0, 1 and 2; and s is, at each occurrence, independently selected from: 1 and 2;

provided that

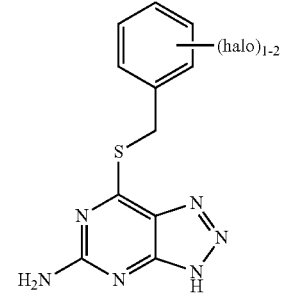

is excluded.

In a second aspect, the present invention includes a compound of Formula (I), or a stereoisomer, a tautomer, a pharmaceutically acceptable salt, a polymorph, or a solvate thereof, within the scope of the first aspect; wherein:

X is CH.

In a third aspect, the present invention includes a compound of Formula (I), or a stereoisomer, a tautomer, a pharmaceutically acceptable salt, a polymorph, or a solvate thereof, within the scope of the second aspect; wherein:

ring A is independently phenyl substituted with 0-1 $R^2$ and 0-3 $R^3$, or a heteroaryl substituted with 0-1 $R^2$ and 0-2 $R^3$ selected from: oxazolyl, isoxazolyl, thiazolyl, pyrazolyl, 1-$R^a$-pyrazolyl, imidazolyl 1-$R^a$-imidazolyl, triazolyl, 1-$R^a$-triazolyl, pyridyl, and pyrimidinyl; and alternatively, $R^2$ and $R^3$, together with the carbon atoms to which they are attached, combine to form a 5- to 6-membered carbocyclic or heterocyclic ring comprising carbon atoms and 0-3 heteroatoms selected from N, $NR^a$, O, and $S(O)_p$; wherein said heterocycle is substituted with 0-2 $R^{19}$.

In a fourth aspect, the present invention includes a compound of Formula (I), or a stereoisomer, a tautomer, a pharmaceutically acceptable salt, a polymorph, or a solvate thereof, within the scope of the second or third aspect, wherein:

ring A is phenyl substituted with 1 $R^2$ and 0-3 $R^3$; and alternatively, $R^2$ and $R^3$, together with the carbon atoms to which they are attached, combine to form a 5- to 6-membered carbocyclic or heterocyclic ring comprising carbon atoms and 0-3 heteroatoms selected from N, $NR^a$, O, and $S(O)_p$; wherein said heterocycle is substituted with 0-2 $R^{19}$.

In a fifth aspect, the present invention includes a compound of Formula (I), or a stereoisomer, a tautomer, a pharmaceutically acceptable salt, a polymorph, or a solvate thereof, within the scope of any of the above aspects, wherein:

Y is independently selected from: $CH_2$, $CHR^1$, $-CH_2CH_2-$, $-CH(C_{1-4}\text{ alkyl})CH_2-$, $-CH_2CH(C_{1-4}\text{ alkyl})-$, $-(CH_2)_{1-3}O(CH_2)_{0-1}-$, $-CH_2CH_2NH(CH_2)_{1-3}-$, $-CH_2CH_2N(C_{1-4}\text{ alkyl})CH_2-$, $-CH_2CH_2NHCHBn-$, $-CH_2CH_2NHCH_2CH(C_{1-4}\text{ alkyl})-$, $-CH_2CH_2NHCH(C_{1-4}\text{ alkyl})CH_2-$, $-CH_2CH_2NHCH_2C(OH)(C_{1-4}\text{ alkyl})-$, and $-(CH_2)_{1-2}CONH-$;

$R^1$ is independently selected from: $-(C_{1-4}\text{ alkyl substituted with 0-1 }R^{18})$, $C_{1-4}$ haloalkyl, COPh, CH(OH)Ph, $CO_2(C_{1-4}\text{ alkyl})$, and CONHBn;

$R^2$ is independently selected from: halogen, CN, $-CH_2CN$, $CH_2OH$, $C_{1-4}$ alkyl, $C_{1-4}$ alkoxy, $C_{1-4}$ haloalkyl, $C_{1-4}$ haloalkoxy, $-CH(NH_2)CF_3$, $-CH_2NHCF_3$, $CO_2(C_{1-4}\text{ alkyl})$, $SO_2(C_{1-4}\text{ alkyl})$, $SO_2Bn$, $SO_2NH_2$, $SO_2NH(C_{1-4}\text{ alkyl})$, $-CH_2SO_2Ph$, $NH_2$, $-CH_2N(C_{1-4}\text{ alkyl})_2$, $-O(CH_2)_3N(C_{1-4}\text{ alkyl})_2$, $CONH_2$, $-CONHCH_2CH_2N(C_{1-4}\text{ alkyl})_2$, $CONH(1-C_{1-4}\text{ alkyl-cyclopropyl})$, $C_{3-6}$ cycloalkyl substituted with 0-1 CN, $-O-C_{3-6}$ cycloalkyl, phenoxy, benzoxy, $-(CH_2)_{0-1}$-(phenyl substituted with 0-2 $R^{11}$ and 0-1 $R^{12}$), pyrrolidinyl, pyrrolidinylmethyl, pyrazolyl, imidazolyl, oxadiazolyl, triazolyl, 1-$C_{1-4}$ alkyl-3-$C_{1-4}$ haloalkyl-pyrazo-5-yl, morpholinylmethyl, pyridyl, $-O$-pyridyl, 2-CN-pyrid-4-yl, 2-$CONH_2$-pyrid-4-yl, 4-(pyrrolidinyl)-pyrid-3-yl, 4-(piperazinyl)-pyrid-3-yl, pyrimidinyl,

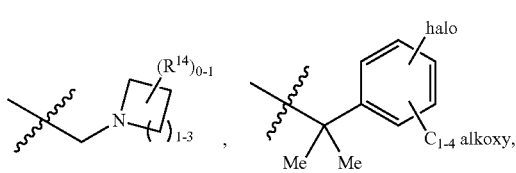

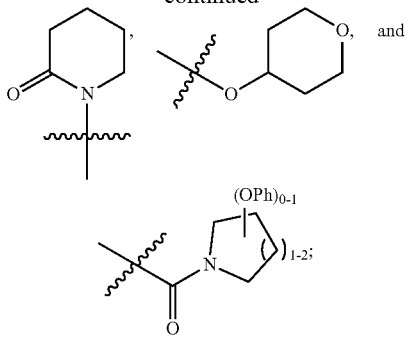

$R^3$ is, at each occurrence, independently selected from: halogen, CN, $C_{1-4}$ alkyl, $C_{1-4}$ alkoxy, and $C_{1-4}$ haloalkyl;

alternatively, $R^2$ and $R^3$, together with the carbon atoms to which they are attached, combine to form a 5- to 6-membered carbocyclic or heterocyclic ring comprising carbon atoms and 0-3 heteroatoms selected from N, $NR^a$, O, and $S(O)_p$; wherein said heterocycle is substituted with 0-2 $R^{19}$;

$R^{18}$ is independently selected from: OH, CN, $N(C_{1-4}\text{ alkyl})_2$, NHBn, imidazolyl and morpholinyl;

$R^{19}$ is independently selected from: halogen and $CO_2(C_{1-4}\text{ alkyl})$; and $R^a$ is, at each occurrence, independently selected from: H, $C_{1-4}$ alkyl, $-(CH_2)_n-C_{3-6}$ cycloalkyl, $-(CH_2)_n$-(phenyl substituted with 0-1 $R^c$), (pyridyl substituted with 0-1 $R^c$), pyrazinyl, pyridazinyl, pyrimidinyl, and

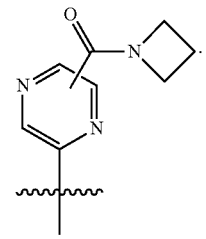

In a sixth aspect, the present disclosure provides a compound of Formula (II),

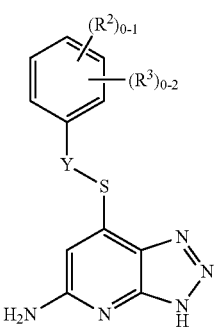

(II)

or a stereoisomer, a tautomer, a pharmaceutically acceptable salt, a polymorph, or a solvate thereof, within the scope of any of the above aspects; wherein:

Y is independently selected from: $CH_2$, $CHR^1$, $-CH_2CH_2-$, $-CH(C_{1-4}\text{ alkyl})CH_2-$, $-CH_2CH(C_{1-4}\text{ alkyl})-$, $-(CH_2)_{1-3}O(CH_2)_{0-1}-$, $-CH_2CH_2NH(CH_2)_{1-3}-$, —CH$_2$CH$_2$N(C$_{1-4}$ alkyl)CH$_2$—, —CH$_2$CH$_2$NHCHBn-, —CH$_2$CH$_2$NHCH$_2$CH(C$_{1-4}$ alkyl)-, —CH$_2$CH$_2$NHCH(C$_{1-4}$ alkyl)CH$_2$—, —CH$_2$CH$_2$NHCH$_2$C(OH)(C$_{1-4}$ alkyl)-, and —CH$_2$CH$_2$CONH—;

R$^1$ is independently selected from: —(C$_{1-4}$ alkyl substituted with 0-1 R$^{18}$), C$_{1-4}$ haloalkyl, COPh, CH(OH)Ph, CO$_2$(C$_{1-4}$ alkyl), and CONHBn;

R$^2$ is independently selected from: halogen, CN, —CH$_2$CN, C$_{1-4}$ alkoxy, C$_{1-4}$ haloalkyl, C$_{1-4}$ haloalkoxy, —CH(NH$_2$)CF$_3$, —CH$_2$NHCF$_3$, CO$_2$(C$_{1-4}$ alkyl), SO$_2$(C$_{1-4}$ alkyl), SO$_2$Bn, SO$_2$NH$_2$, SO$_2$NH(C$_{1-4}$ alkyl), —CH$_2$SO$_2$Ph, —CH$_2$N(C$_{1-4}$ alkyl)$_2$, —O(CH$_2$)$_3$N(C$_{1-4}$ alkyl)$_2$, CONH$_2$, —CONHCH$_2$CH$_2$N(C$_{1-4}$ alkyl)$_2$, CONH(1-C$_{1-4}$ alkyl-cyclopropyl), C$_{3-6}$ cycloalkyl substituted with 0-1 CN, —O—C$_{3-6}$ cycloalkyl, 2-(SO$_2$NH(C$_{1-4}$ alkyl))-Ph, Bn, phenoxyl, pyrazolyl, imidazolyl, oxadiazolyl, triazolyl, 1-C$_{1-4}$ alkyl-3-C$_{1-4}$ haloalkyl-pyrazo-5-yl, morpholinylmethyl, pyridyl, —O-pyridyl, 2-CN-pyrid-4-yl, 2-CONH$_2$-pyrid-4-yl, 4-(pyrrolidinyl)-pyrid-3-yl, 4-(piperazinyl)-pyrid-3-yl, pyrimidinyl,

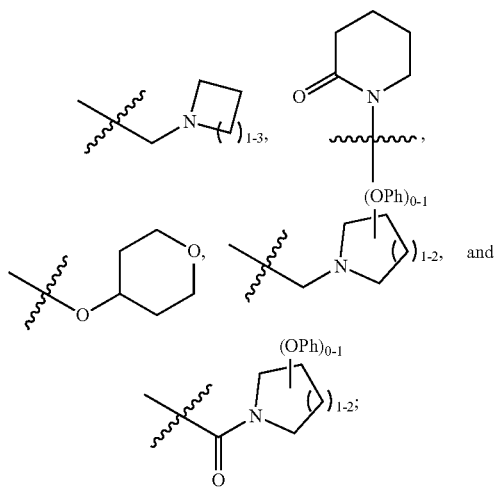

R$^3$ is, at each occurrence, independently selected from: halogen, CN, C$_{1-4}$ alkyl, C$_{1-4}$ alkoxy, and C$_{1-4}$ haloalkyl; and R$^{18}$ is independently selected from: OH, CN, N(C$_{1-4}$ alkyl)$_2$, NHBn, imidazolyl and morpholinyl.

In a seventh aspect, the present invention provides a compound selected from the exemplified examples a stereoisomer, a tautomer, a pharmaceutically acceptable salt, a polymorph, or a solvate thereof.

In another aspect, the present invention provides a compound selected from any subset list of compounds within the scope of the eighth aspect.

In another embodiment, the compounds of the present invention have IC$_{50}$ values ≤10 μM, using the MPO peroxidation assay disclosed herein, preferably, IC$_{50}$ values ≤3 μM, more preferably, IC$_{50}$ values 0.3 μM, even more preferably, IC$_{50}$ values ≤0.1 μM.

In another embodiment, the compounds of the present invention have IC$_{50}$ values ≤10 μM, using the MPO chlorination assay disclosed herein, preferably, IC$_{50}$ values ≤3 μM, more preferably, IC$_{50}$ values 0.3 μM, even more preferably, IC$_{50}$ values ≤0.1 μM.

In another embodiment, the compounds of the present invention have IC$_{50}$ values ≤10 μM, using the EPX bromination assay described herein, preferably, IC$_{50}$ values ≤3 μM, more preferably, IC$_{50}$ values 0.3 μM, even more preferably, IC$_{50}$ values ≤0.1 μM.

II. Other Embodiments of the Invention

In another embodiment, the present invention provides a composition comprising at least one of the compounds of the present invention or a stereoisomer, a tautomer, a pharmaceutically acceptable salt, a polymorph, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, a polymorph, or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, a pharmaceutically acceptable salt, a polymorph, or a solvate thereof.

In another embodiment, the present invention provides a pharmaceutical composition as defined above further comprising additional therapeutic agent(s).

In another embodiment, the present invention provides a process for making a compound of the present invention.

In another embodiment, the present invention provides an intermediate for making a compound of the present invention.

In another embodiment, the present invention provides a compound of the present invention, for use in therapy, alone, or optionally in combination with another compound of the present invention and/or at least one other type of therapeutic agent.

In another embodiment, the present invention provides a compound of the present invention for use in therapy, for the treatment of diseases or disorders associated with the activity of MPO and/or EPX, alone, or optionally in combination with another compound of the present invention and/or at least one other type of therapeutic agent.

In another embodiment, the present invention provides a method for the treatment of diseases or disorders associated with the activity of MPO and/or EPX, comprising administering to a patient in need of such treatment a therapeutically effective amount of at least one of the compounds of the present invention, alone, or optionally in combination with another compound of the present invention and/or at least one other type of therapeutic agent.

In another embodiment, the present invention provides a method for the treatment of diseases or disorders associated with the activity of MPO and/or EPX, comprising administering to a patient in need thereof a therapeutically effective amount of a first and second therapeutic agent, wherein the first therapeutic agent is a compound of the present invention and the second therapeutic agent is one other type of therapeutic agent.

In another embodiment, the present invention also provides the use of a compound of the present invention for the manufacture of a medicament for the treatment of diseases or disorders associated with the activity of MPO and/or EPX, alone, or optionally in combination with another compound of the present invention and/or at least one other type of therapeutic agent.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of diseases or disorders associated with the activity of MPO and/or EPX.

Examples of diseases or disorders associated with the activity of MPO and/or EPX that may be prevented, modulated, or treated according to the present invention include, but are not limited to, atherosclerosis, coronary heart disease, coronary artery disease, coronary vascular disease, cerebrovascular disorders, peripheral vascular disease, dyslipidemias and the sequelae thereof, cardiovascular disorders, angina, ischemia, cardiac ischemia, heart failure, stroke, myocardial infarction, reperfusion injury, angioplastic restenosis, hypertension, vascular complications of diabetes, obesity or endotoxemia.

In one embodiment, examples of diseases or disorders include, but are not limited to, atherosclerosis, coronary artery disease, acute coronary syndrome, dyslipidemias and the sequelae thereof, heart failure, lung diseases including asthma, COPD and cystic fibrosis, and neuroinflammatory diseases, including multiple sclerosis, Alzheimer's disease, Parkinson's disease, multiple system atrophy, transient ischemic attack and stroke. In one embodiment, examples of diseases or disorders include atherosclerosis, coronary heart disease, cerebrovascular disorders and dyslipidemias and the sequelae thereof. In one embodiment, examples of diseases or disorders include coronary artery disease and acute coronary syndrome. In one embodiment, examples of diseases or disorders include dyslipidemias and the sequelae thereof. In one embodiment, examples of diseases or disorders include heart failure. In one embodiment, examples of diseases or disorders include lung diseases including asthma, COPD and cystic fibrosis. In one embodiment, examples of diseases or disorders include neuroinflammatory diseases, including multiple sclerosis, Alzheimer's disease, Parkinson's disease, multiple system atrophy, and stroke.

The compounds of the present invention may be employed in combination with additional therapeutic agent(s) selected from one or more, preferably one to three, of the following therapeutic agents: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, diuretics, mineralocorticoid receptor antagonists, calcium channel blockers, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

In another embodiment, additional therapeutic agent(s) used in combined pharmaceutical compositions or combined methods or combined uses, are selected from one or more, preferably one to three, of the following therapeutic agents in treating atherosclerosis: anti-hyperlipidemic agents, plasma high-density lipoprotein (HDL)-raising agents, anti-hypercholesterolemic agents, cholesterol biosynthesis inhibitors (such as HMG CoA reductase inhibitors), acyl-coenzyme A:cholesterol acytransferase (ACAT) inhibitors, cholesterylester transfer protein (CETP) inhibitors, liver X receptor (LXR) agonists, anti-probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, diuretics, mineralocorticoid receptor antagonists, calcium channel blockers, anti-diabetes agents, angiotensin II receptor antagonists, angiotensin converting enzyme inhibitors, platelet aggregation inhibitors, factor Xa inhibitors, anti-thrombotic agents, renin inhibitors, fibrinogen receptor antagonists, aspirin and fibric acid derivatives.

In another embodiment, additional therapeutic agent(s) used in combined pharmaceutical compositions or combined methods or combined uses, are selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. The term "stereoisomer(s)" refers to compound(s) which have identical chemical constitution, but differ with regard to the arrangement of the atoms or groups in space. Unless otherwise indicated, all chiral (enantiomeric and diastereomeric) and racemic forms are within the scope of the invention. The term "chiral" refers to molecules which have the property of non-superimposability of the mirror image partner, while the term "achiral" refers to molecules which are superimposable on their mirror image partner. The terms "racemic mixture" and "racemate" refer to an equimolar mixture of two enantiomeric species, devoid of optical activity.

Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms.

The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization.

Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

Unless otherwise indicated, any heteroatom with unsatisfied valences is assumed to have hydrogen atoms sufficient to satisfy the valences.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_{1-6}$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond.

"Alkenyl" or "alkenylene" is intended to include hydrocarbon chains of either straight or branched configuration having the specified number of carbon atoms and one or more, preferably one to two, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, and 4-methyl-3-pentenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with one or more fluorine atoms.

"Haloalkoxy" or "haloalkyloxy" represents a haloalkyl group as defined above with the indicated number of carbon atoms attached through an oxygen bridge. For example, "$C_1$ to $C_6$ haloalkoxy" or "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, indanyl, and tetrahydronaphthyl. When the term "carbocycle" is used, it is intended to include "aryl". A bridged ring occurs when one or more, preferably one to three, carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 15th Edition, John Wiley & Sons, Inc., New York (2007). "$C_6$ or $C_{10}$ aryl" or "$C_{6-10}$ aryl" refers to phenyl and naphthyl.

The term "benzyl", as used herein, refers to a methyl group on which one of the hydrogen atoms is replaced by a phenyl group.

As used herein, the term "heterocycle", "heterocyclyl", or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and S(O)$_p$, wherein p is 0, 1 or 2).

Examples of 5- to 6-membered heteroaryls include, but are not limited to, pyridinyl, furanyl, thienyl, pyrrolyl, pyrazolyl, pyrazinyl, imidazolyl, imidazolidinyl, tetrazolyl, isoxazolyl, oxazolyl, oxadiazolyl, oxazolidinyl, thiadiazinyl, thiadiazolyl, thiazolyl, triazinyl, and triazolyl.

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counter ion" is used to represent a negatively charged species such as chloride, bromide, hydroxide, acetate, and sulfate or a positively charged species such as sodium (Na+), potassium (K+), ammonium (R$_n$NH$_m$+ where n=0-4 and m=0-4) and the like.

When a dotted ring is used within a ring structure, this indicates that the ring structure may be saturated, partially saturated or unsaturated.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Greene, T. W. et al., *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent.

Combinations of substituents and/or variables are permissible only if such combinations result in stable compounds.

As a person of ordinary skill in the art would be able to understand, a ketone (—CH—C=O) group in a molecule may tautomerize to its enol form (—C=C—OH). Thus, this disclosure is intended to cover all possible tautomers even when a structure depicts only one of them.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

Compounds of the present invention can form salts which are also within the scope of this invention. Unless otherwise indicated, reference to an inventive compound is understood to include reference to one or more salts thereof. Pharmaceutically acceptable salts are preferred. However, other salts may be useful, e.g., in isolation or purification steps which may be employed during preparation, and thus, are contemplated within the scope of the invention.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Allen, L. V., Jr., ed., *Remington: The Science and Practice of Pharmacy,* 22nd Edition, Pharmaceutical Press, London, UK (2012), the disclosure of which is hereby incorporated by reference.

In addition, compounds of the present invention may have prodrug forms. Any compound that will be converted in vivo to provide the bioactive agent (i.e., a compound of Formula (I) or Formula (II)) is a prodrug within the scope and spirit of the invention. Various forms of prodrugs are well known in the art. For examples of such prodrug derivatives, see:

a) Bundgaard, H., ed., *Design of Prodrugs,* Elsevier (1985), and Widder, K. et al., eds., *Methods in Enzymology,* 112:309-396, Academic Press (1985);

b) Bundgaard, H., Chapter 5, "Design and Application of Prodrugs", *A Textbook of Drug Design and Development,* pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988);

e) Kakeya, N. et al., *Chem. Pharm. Bull.,* 32:692 (1984); and f) Rautio, J., ed., Prodrugs and Targeted Delivery (*Methods and Principles in Medicinal Chemistry*), Vol. 47, Wiley-VCH (2011).

Compounds containing a carboxy group can form physiologically hydrolyzable esters that serve as prodrugs by being hydrolyzed in the body to yield Formula (I) or Formula (II) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of Formula (I) or Formula (II) include $C_1$ to $C_6$ alkyl, $C_1$ to $C_6$ alkylbenzyl, 4-methoxybenzyl, indanyl, phthalyl, methoxymethyl, $C_{1-6}$ alkanoyloxy-$C_{1-6}$ alkyl (e.g., acetoxymethyl, pivaloyloxymethyl or propionyloxymethyl), $C_1$ to $C_6$ alkoxycarbonyloxy-$C_1$ to $C_6$ alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice,* The Royal Society of Chemistry, Cambridge, UK (2nd Edition, reproduced, 2006); Testa, B. et al., *Hydrolysis in Drug and Prodrug Metabolism. Chemistry, Biochemistry and Enzymology,* VCHA and Wiley-VCH, Zurich, Switzerland (2003); Wermuth, C. G., ed., *The Practice of Medicinal Chemistry,* 3rd Edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, "polymorph(s)" refer to crystalline form(s) having the same chemical structure/composition but different spatial arrangements of the molecules and/or ions forming the crystals. Compounds of the present invention can be provided as amorphous solids or crystalline solids. Lyophilization can be employed to provide the compounds of the present invention as a solid.

Abbreviations as used herein, are defined as follows: "1×" for once, "2×" for twice, "3×" for thrice, "° C." for degrees Celsius, "aq" for aqueous, "Col" for column, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "RT" for retention time, "ON" for overnight, "atm" for atmosphere, "psi" for pounds per square inch, "conc." for concentrate, "aq" for aqueous, "sat" or "sat'd" for saturated, "MW" for molecular weight, "mw" or "µwave" for microwave, "mp" for melting point, "Wt" for weight, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1H$" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Ac: Acetic (AcOH: acetic acid, EtOAc: ethyl acetate)
ACN (or MeCN): acetonitrile
APF: aminophenyl fluorescein
BINAP: 2,2'-bis(diphenylphosphino)-1,1'-binaphthyl Bn: benzyl
Boc: tert-butyl carbonyl
Boc₂O: Di-tert-butyl dicarbonate
Bu: butyl
dba: dibenzylideneacetone (e.g. Pd₂(dba)₃):
DCM: dichloromethane
DEAD: diethyl azodicarboxylate
DIEA: diisopropylethylamine
DMAP: 4-dimethylaminopyridine
DME: dimethoxyethane
DMF: dimethylformamide
DMSO: dimethyl sulfoxide
dppf (PdCl₂(dppf)): 1,1'-bis(diphenylphosphino)ferrocene
Et: ethyl (EtOH: ethanol, EtOAc: ethyl acetate)
HATU: 2-(7-Aza-1H-benzotriazole-1-yl)-1,1,3,3-tetramethyluronium
hexafluorophosphate hex: hexanes
HBTU: 2-(1H-Benzotriazole-1-yl)-1,1,3,3-tetramethyluronium hexafluorophosphate
i-Bu: isobutyl
i-Pr: isopropyl
Me: methyl (MeOH: methanol, MeCN: acetonitrile)
NMP: N-Methylpyrrolidone
Ph: phenyl
Pr: propyl
rt: room temperature
t-Bu: tert-butyl
TCA: Trichloroacetic acid
TFA: Trifluoroacetic acid
THF: tetrahydrofuran
Trt: trityl
Ts: tosyl Synthesis The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

A particularly useful compendium of synthetic methods which may be applicable to the preparation of compounds of the present invention may be found in Larock, R. C., *Comprehensive Organic Transformations*, VCH Publishers, Inc., New York, N.Y. (1999). Preferred methods include, but are not limited to, those described below. All references cited herein are hereby incorporated in their entirety herein by reference.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene, T. W. et al., *Protecting Groups in Organic Synthesis*, 4th Edition, Wiley (2007)). Protecting groups incorporated in making of the triazolopyridine and triazolopyrimidine compounds of the present invention, such as the trityl protecting group, may be shown as one regioisomer but may also exist as a mixture of regioisomers.

Compounds having the general Formula (I):

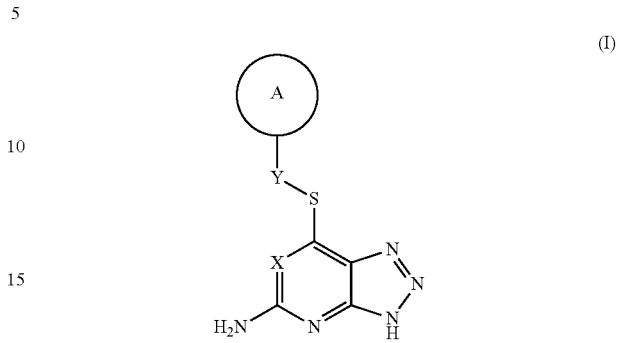

wherein A and Y are defined above, can be prepared by the following one or more of the synthetic Schemes.

Scheme 1

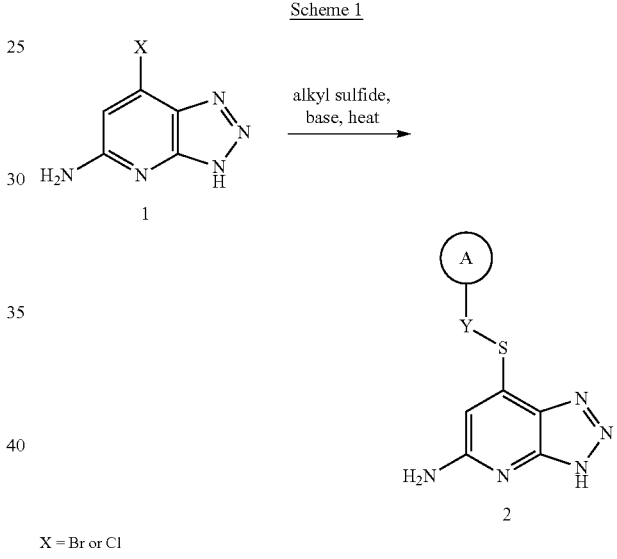

X = Br or Cl

A mixture of chloro or bromotriazolopyridine 1 with a base such as sodium hydride or cesium carbonate and an alkyl sulfide can be heated in a suitable solvent such as DMSO to afford the desired triazolopyridine. The synthesis of chloro or bromotriazolopyridine 1 is provided in the methods below as Intermediate 2. Many sulfides are commercially available and can also be prepared by methods known in the art.

Scheme 2

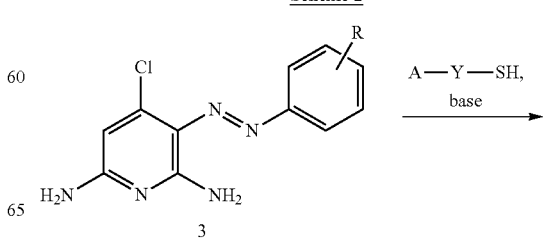

-continued

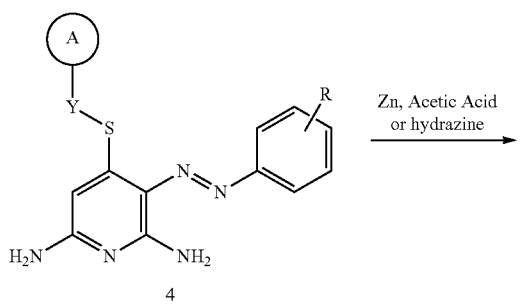
4

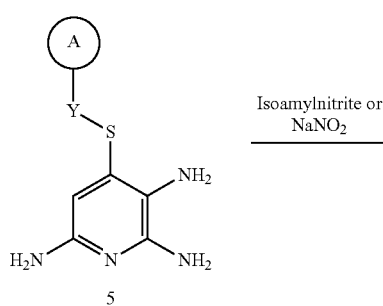
5

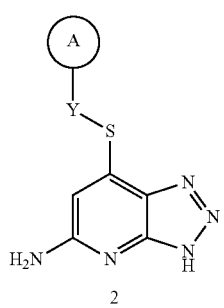
2

R is a variable

Alternatively as described in Scheme 2, diaza intermediate 3 can be heated with a base such as cesium carbonate and a thiol in a solvent such as DMSO to yield thioether 4. Compound 4 can be converted to triamine 5 by heating with hydrazine or with zinc in a mixture of acetic acid and ethanol or methanol. The triamine can be cyclized with isoamylnitrite or sodium nitrite or other reagent with similar reactivity to yield triazolopyridine 2. The synthesis of an example diaza intermediate 3 is described below in the General Synthesis Procedures as Intermediate 1.

Scheme 3

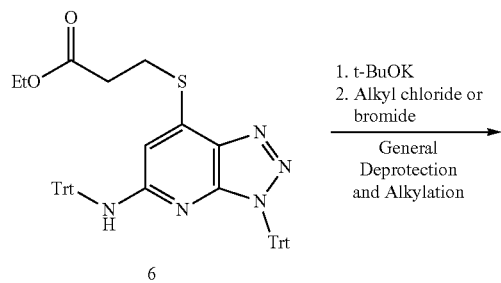
6

-continued

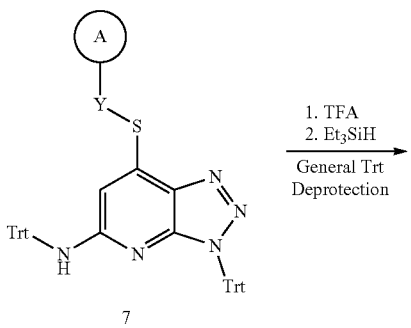
7

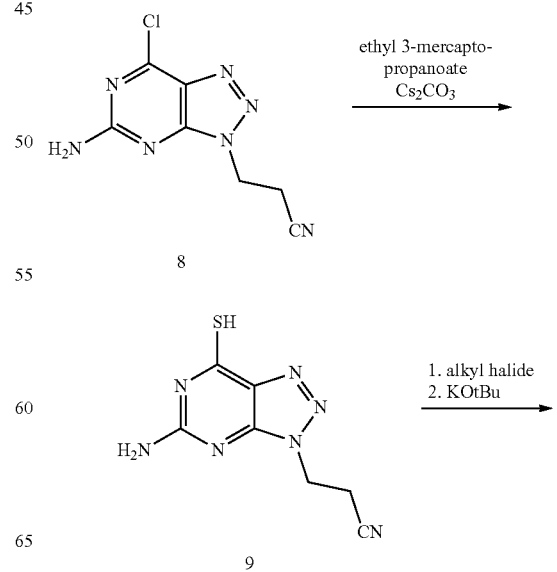

Additionally, the described triazolopyridines can be synthesized via deprotection of the ethyl propionate from compound 6 with a suitable base such as t-BuOK (2-4 eq) to yield the free aryl thiol. Addition of an alkyl chloride or bromide (1-2 eq) to the reaction mixture produces thioether 7. Deprotection of the trityl groups with a TFA/DCM mixture in the presence of triethyl silane (2-10 eq) results in the described triazolopyridines. The synthesis of compound 6 is described below in the General Synthesis Procedures as Intermediate 3.

Scheme 4

-continued

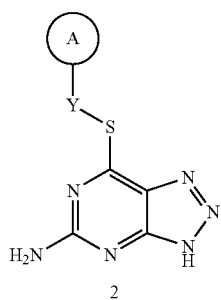

2

The thiopyrimidines can be prepared by treating chloride 8 with ethyl 3-mercaptopropanoate (3 eq) and $Cs_2CO_3$ (3 eq), in DMSO for 12-16 hours to yield intermediate thiol 9, which is treated with an alkyl bromide or alkyl chloride (3 eq). The protecting group can be removed with potassium tert-butoxide (4 eq). The synthesis of compound 8 is described below in the General Synthesis Procedures as Intermediate 4.

General Methods

The following methods were used in the exemplified Examples, except where noted otherwise.

Purification of intermediates and final products was carried out via either normal or reverse phase chromatography. Normal phase chromatography was carried out using pre-packed $SiO_2$ cartridges eluting with either gradients of hexanes and ethyl acetate or DCM and MeOH unless otherwise indicated. For highly polar amines, gradients of DCM and 1M $NH_3$ in MeOH were used. Reverse phase preparative HPLC was carried out using C18 columns with UV 220 nm or prep LCMS detection eluting with gradients of Solvent A (90% water, 10% MeOH, 0.1% TFA) and Solvent B (10% water, 90% MeOH, 0.1% TFA) or with gradients of Solvent A (90% water, 10% ACN, 0.1% TFA) and Solvent B (10% water, 90% ACN, 0.1% TFA) or with gradients of Solvent A (95% water, 2% ACN, 0.1% HCOOH) and Solvent B (98% ACN, 2% water, 0.1% HCOOH) or with gradients of Solvent A (95% water, 5% ACN, 10 mM $NH_4OAc$) and Solvent B (98% ACN, 2% water, 10 mM $NH_4OAc$) or with gradients of Solvent A (98% water, 2% ACN, 0.1% $NH_4OH$) and Solvent B (98% ACN, 2% water, 0.1% $NH_4OH$).

LC/MS Methods Employed in Characterization of Examples

Reverse phase analytical HPLC/MS was performed on Shimadzu LC10AS systems coupled with Waters ZMD Mass Spectrometers (Methods A-E) or Waters Acquity system coupled with a Waters MICROMASS® ZQ Mass Spectrometer (Method F and G).

Method A: Linear gradient of 0 to 100% B over 4 min, with 1 min hold at 100% B;
  UV visualization at 220 nm
  Column: PHENOMENEX® Luna C18 4.6×50 mm
  Flow rate: 4 mL/min
  Solvent A: 0.1% trifluoroacetic acid, 90% water, 10% acetonitrile
  Solvent B: 0.1% trifluoroacetic acid, 90% acetonitrile, 10% water.

Method B: Linear gradient of 0 to 100% B over 4 min, with 1 min hold at 100% B;
  UV visualization at 220 nm
  Column: PHENOMENEX® Luna C18 2×50 mm
  Flow rate: 4 mL/min
  Solvent A: 98% water, 2% methanol, 0.1% formic acid
  Solvent B: Methanol, 0.1% formic acid.

Method C: Linear gradient of 0 to 100% B over 4 min, with 1 min hold at 100% B;
  UV visualization at 220 nm
  Column: PHENOMENEX® Luna C18 4.6×50 mm
  Flow rate: 4 mL/min
  Solvent A: 0.1% trifluoroacetic acid, 90% water, 10% methanol
  Solvent B: 0.1% trifluoroacetic acid, 90% methanol, 10% water.

Method D: Linear gradient of 0 to 100% B over 2 min, with 1 min hold at 100% B;
  UV visualization at 220 nm
  Column: PHENOMENEX® Luna C18 2.0×30 mm
  Flow rate: 1 mL/min
  Solvent A: 0.1% trifluoroacetic acid, 90% water, 10% methanol
  Solvent B: 0.1% trifluoroacetic acid, 90% methanol, 10% water.

Method E: Linear gradient of 0 to 100% B over 2 min, with 1 min hold at 100% B;
  UV visualization at 220 nm
  Column: PHENOMENEX® Luna C18 2.0×30 mm
  Flow rate: 1 mL/min
  Solvent A: 98% water, 2% methanol, 0.1% formic acid
  Solvent B: Methanol, 0.1% formic acid.

Method F: Linear gradient of 0 to 100% B over 3 min, with 0.75 min hold time at 100% B;
  UV visualization at 220 nm
  Column: Waters BEH C18 2.1×50 mm
  Flow rate: 1.1 mL/min
  Solvent A: 0.1% TFA, 95% water, 5% acetonitrile
  Solvent B: 0.1% TFA, 5% water, 95% acetonitrile Method G: Linear gradient of 0 to 100% B over 3 min, with 0.75 min hold time at 100% B;
  UV visualization at 220 nm
  Column: Waters BEH C18 2.1×50 mm
  Flow rate: 1.1 mL/min
  Solvent A: 10 mM ammonium acetate, 95% water, 5% acetonitrile
  Solvent B: 10 mM ammonium acetate, 5% water, 95% acetonitrile NMR Employed in Characterization of Examples $^1$H NMR spectra were obtained with Bruker or JEOL® Fourier transform spectrometers operating at frequencies as follows: $^1$H NMR: 400 MHz (Bruker or JEOL®) or 500 MHz (Bruker or JEOL®). $^{13}$C NMR: 100 MHz (Bruker or JEOL®). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for $CD_2HSOCD_3$, 3.30 ppm for $CD_2HOD$, 1.94 for $CD_3CN$, and 7.24 ppm for $CHCl_3$, and which in $^{13}$C NMR spectra appear at 39.7 ppm for $CD_3SOCD_3$, 49.0 ppm for $CD_3OD$, and 77.0 ppm for $CDCl_3$. All $^{13}$C NMR spectra were proton decoupled.

IV. Biology

Myeloperoxidase (MPO) and eosinophil peroxidase (EPX) are heme-containing enzymes and are members of the family of mammalian heme peroxidases that also includes salivary peroxidase, lactoperoxidase (LPO), thyroid peroxidase (TPO), prostaglandin H synthase and others. Both MPO and EPX use hydrogen peroxide to oxidize an array of substrates to either hypohalous acids or free radicals. Whereas both EPX and MPO are able to oxidize bromine (Br⁻), iodine (I⁻) and thiocyanate (⁻SCN), only MPO is able to oxidize chloride (Cl⁻) to hypochlorous acid (HOCl) efficiently.

MPO is present predominantly in neutrophils and to a lesser extent in monocytes and subtypes of tissue macrophages. The processed mature form of the enzyme is a glycosylated 146 kDa homodimer. Each subunit is made of a light and heavy polypeptide chain and contains a protoporphyrin IX group with a central iron. The three-fold linkage of the heme is unique compared to other heme proteins and provides specific spectral and catalytic properties to MPO. MPO uses hydrogen peroxide to oxidize an array of substrates to either hypohalous acids or free radicals. The main substrate for MPO is generally accepted to be chloride, which is oxidized to hypochlorous acid. This is one of the most reactive oxidants produced in vivo. Other substrates include thiocyanate, bromide, tyrosine, tryptophan, sulfhydryls, phenol and indole derivatives, ascorbate, nitrite, nitric oxide, and urate.

The physiological role of MPO is to participate in the killing of invading bacterial and fungal pathogens (Klebanoff, S. J., *J. Exp Med.*, 126:1063-1078 (1967); Klebanoff, S. J., *J. Bacteriol.*, 95:2131-2138 (1968); Klebanoff, S. J., *Science*, 169:1095-1097 (1970)). However, excessive generation of oxidants by MPO and other peroxidases has been linked to tissue damage in many diseases, especially those characterized by acute or chronic inflammation. At sites of inflammation, PMNs or tissue macrophages can generate hydrogen peroxide and upon activation also produce myeloperoxidase. This is evidenced by the fact that, in many cases, enzymatically active MPO in conjunction with 3-chlorotyrosine, a tissue marker for HOCl-mediated damage, or HOCl-modified proteins can be detected in diseased tissues colocalized with neutrophils or macrophages (Daugherty, A. et al., *JCI*, 94:437-444 (1994); Bergt et al., *Proc. Natl. Acad. Sci.*, 101:13032-13037 (2004); Pennathur, S. et al., *JBC*, 279:42977-42983 (2004); Choi, D. K. et al., *J. Neurosci.*, 25(28):6394-6600 (2005)).

Eosinophil peroxidase (EPX) is a cationic heme-containing protein, and represents nearly 25% of the total mass of the secondary granule protein in eosinophils. It is an highly basic 77 kDa protein made up of two subunits containing a modified Fe-protoporphyrin-IX prosthetic group. EPX shares with MPO the ability to use $H_2O_2$ to oxidize thiocyanate, bromide, and nitrite in vivo to kill bacteria, and viruses (Jong, E. C. et al., *J. Immunol.*, 124:1949-1953 (1980)). Eosinophils play a unique role in host defense mechanisms but increased levels of circulating and tissue eosinophils are implicated in promoting cellular and tissue injury in particular in asthma, and during allergic inflammatory responses of lung diseases.

MPO Peroxidation Assay

MPO peroxidation activity was measured in 100 mM KPi (pH 7.4) by utilizing the non-fluorescent reagent Amplex Red (Invitrogen catalog #A12222) which can be oxidized to the highly fluorescent resorufin. Amplex Red is oxidized by the peroxidase action of MPO to resorufin. Reactions were carried out in 50 μL total volume by adding a 25 μL mixture of 200 pM myeloperoxidase and 40 nM $H_2O_2$ (Sigma #349887) to 100 nL inhibitor in 100% DMSO in a 384 well Perkin Elmer Optiplate. Enzyme and compound were preincubated for ten minutes at rt.

After the ten minute preincubation, 25 μL of an Amplex Red mixture containing 200 μM Amplex Red and 10 mM $H_2O_2$ was added to the plate. Kinetic determinations were carried out immediately on a Perkin Elmer Envision (15 minute kinetic read, Ex: 535 nm, Em: 590 nm).

$IC_{50}$ values were calculated by determining the slope of the linear portion of the kinetic trace (180-540 secs), and using that calculated slope to determine % inhibition occurring at each concentration of inhibitor using the following equation:

$$Y = A + \frac{B - A}{1 + (C/x)^D}$$

where A=minimal Y value (activity level of inhibited sample), B=maximal Y value (activity level of uninhibited sample), C=Log $IC_{50}$, D=Hill Slope, x=concentration of inhibitor.

MPO Chlorination Assay

MPO chlorination activity was measured in 100 mM KPi (pH 7.4) by utilizing the non-fluorescent reagent Aminophenyl fluorescein (APF, Invitrogen catalog #A36003). APF is cleaved by (—OCl) to yield the fluorescent compound fluorescein. Reactions were carried out in 50 μL total volume by adding a 25 μL mixture of 200 pM myeloperoxidase and 120 mM NaCl to 100 nL inhibitor in 100% DMSO in a 384 well, non-binding surface clear bottom plate (CORNING® #3655). Enzyme, inhibitor, and chloride were preincubated for ten minutes at rt.

After the ten minute preincubation, 25 μL of an APF mixture containing 10 mM APF, 120 mM NaCl and 10 μM $H_2O_2$ was added to the plate using the internal dispensing system of a Hammatsu FDSS 6000. Kinetic determinations were carried out immediately on the FDSS 6000 (3 minute kinetic read, 1 read every second, ex: 485 nm, em: 535 nm). $IC_{50}$ values for inhibitors were calculated by taking the slope of the linear portion of the kinetic measurement (20 seconds to ~80-120 secs).

$IC_{50}$ values were calculated by determining the slope of the linear portion of the kinetic trace (180-540 secs), and using that calculated slope to determine % inhibition occurring at each concentration of inhibitor using the following equation:

$$Y = A + \frac{B - A}{1 + (C/x)^D}$$

where A=minimal Y value (activity level of inhibited sample), B=maximal Y value (activity level of uninhibited sample), C=Log $IC_{50}$, D=Hill Slope, x=concentration of inhibitor.

EPX Bromination Assay

EPX bromination activity was measured in 100 mM KPi (pH 7.4) by monitoring the $H_2O_2$ catalyzed formation of 3-bromo tyrosine from tyrosine and potassium bromide. A 50 μl mixture of 0.6 μM EPX (Lee Biosolutions Cat #342-60) was added to 100 nL inhibitor in 100% DMSO in a 384 well REMP plate. Enzyme and compound were preincubated for ten minutes at rt.

After the ten minute preincubation of enzyme and inhibitor, 25 μL of a mixture containing 400 μM tyrosine and 1200 μM potassium bromide was added to the plate containing enzyme and inhibitor, followed by the addition of 25 μl of 20 μM $H_2O_2$. The reaction was allowed to proceed for 15 minutes, at which time it was quenched with 10 μL of 20% TCA. The final concentrations of all components were 0.3 μM EPX, 100 μM tyrosine, 400 μM potassium bromide, 5 μM $H_2O_2$, 0.1% DMSO, 2.0% TCA.

IC$_{50}$ values were determined by determining the peak areas of 3-bromotyrosine present at the end of the 15 minute reaction and fitting the data to:

$$Y = A + \frac{B-A}{1+(C/x)^D}$$

where A=minimal Y value (activity level of inhibited sample), B=maximal Y value (activity level of uninhibited sample), C=Log IC$_{50}$, D=Hill Slope, x=concentration of inhibitor.

Reversed-phase analysis was performed on a Waters Acquity Ultra Performance LC system using an Acquity UPLC BEH C$_{18}$ 1.7 µM, 2.1×50 mm analytical column. The column was maintained at 60° C. Samples were eluted using a gradient of 0%-100% B over 2.5 minutes, followed by equilibration with 100% A for 1 minute where A consisted of 0.1% TFA and B consisted of 90% MeOH/0.1% TFA at a flow rate of 0.6 mL/min. The retention time of 3-bromo tyrosine was 1.22 min.

The exemplified Examples disclosed below were tested in the MPO peroxidation assay described above and found having MPO inhibitory activity. A range of IC$_{50}$ values of ≤3 µM (3000 nM) was observed.

Some of the exemplified Examples disclosed below were tested in the MPO chlorination assay described above and found having MPO inhibitory activity. A range of IC$_{50}$ values of ≤3 µM (3000 nM) was observed.

Some compounds of the invention were tested in the EPX bromination assay described above and were found to inhibit EPX with a range of IC$_{50}$ values of ≤3 µM (3000 nM), as demonstrated by Example 2 (EPX IC$_{50}$=0.001 µM), Example 7 (EPX IC$_{50}$=0.02 µM), Example 11 (EPX IC$_{50}$=0.002 µM) and Example 51 (EPX IC$_{50}$=0.006 µM).

Table 1 below lists IC$_{50}$ values in the MPO peroxidation (Amplex Red) assay and/or MPO chlorination assay (APF) measured for the following examples.

TABLE 1

| Example No. | APF IC$_{50}$ (µM) | Amplex Red IC$_{50}$ (µM) |
|---|---|---|
| 2 | 0.01 | 0.01 |
| 3 | 0.01 | 0.007 |
| 28 | 0.08 | 0.01 |
| 39 | 0.02 | 0.01 |
| 41 | 0.08 | 0.02 |
| 45 | 0.08 | 0.02 |
| 57 | 0.50 | 0.10 |
| 59 | 0.08 | 0.03 |
| 66 | 0.02 | 0.01 |
| 70 | 0.76 | 0.05 |
| 72 | 0.58 | 0.46 |
| 77 | 0.61 | 0.14 |
| 79 | 0.007 | 0.03 |
| 88 | 0.009 | 0.03 |
| 98 | 0.64 | 0.53 |
| 104 | 0.09 | 0.01 |
| 113 | 0.01 | 0.02 |
| 116 | 0.53 | 0.10 |
| 126 | 0.08 | 0.02 |
| 139 | 0.01 | 0.17 |
| 144 | 0.08 | 0.04 |
| 145 | 0.08 | 0.03 |
| 164 | 0.77 | 0.22 |
| 166 | 0.57 | 0.79 |

The following Examples were tested in the MPO chlorination assay described above and found having MPO inhibitory activity with IC$_{50}$ values of ≤0.06 µM (60 nM): 1, 4, 5, 6, 7, 8, 9, 10, 11, 12, 14, 15, 17, 18, 19, 20, 23, 29, 42, 43, 47, 56, 60, 64, 68, 74, 78, 83, 84, 85, 86, 87, 90, 91, 93, 109, 112, 117, 118, 121, 122, 125, 130, 133, 134, 135, 136, 137, 138, 141, 142, 148, 150, and 151.

The following Examples were tested in the MPO chlorination assay described above and found having MPO inhibitory activity in the range of IC$_{50}$ values between 0.06 µM (60 nM) and 0.20 µM (200 nM): 16, 21, 22, 24, 25, 30, 32, 33, 34, 35, 44, 46, 48, 49, 50, 51, 52, 53, 54, 61, 62, 63, 65, 73, 75, 76, 80, 81, 82, 89, 92, 94, 95, 96, 97, 99, 100, 101, 102, 103, 105, 106, 107, 108, 110, 111, 114, 115, 119, 123, 128, 132, 149, 153, 154, 155, and 156.

The following Examples were tested in the MPO chlorination assay described above and found having MPO inhibitory activity in the range of IC$_{50}$ values between 0.20 µM (200 nM) and 1.0 µM (1000 nM): 26, 27, 31, 36, 37, 38, 40, 55, 58, 67, 69, 71, 120, 124, 127, 129, 131, 140, 143, 146, 147, 152, 157, 158, 159, 160, 161, 162, 163, and 165.

Accordingly, the compounds of the present invention may be administered to mammals, preferably humans, for the treatment of a variety of conditions and disorders, including, but not limited to, atherosclerosis, coronary artery disease, acute coronary syndrome, dyslipidemias and the sequelae thereof, angina, ischemia, cardiac ischemia, myocardial infarction, reperfusion injury, angioplastic restenosis, hypertension, vascular complications of diabetes, obesity or endotoxemia, heart failure, lung diseases including asthma, COPD and cystic fibrosis, and neuroinflammatory diseases, including multiple sclerosis, Alzheimer's disease, Parkinson's disease, multiple system atrophy, and stroke, as well as chronic inflammatory diseases such as inflammatory bowel disease, renal glomerular damage and rheumatoid arthritis.

As used herein, the term "patient" encompasses all mammalian species.

As used herein, the term "subject" refers to any human or non-human organism that could potentially benefit from treatment with a MPO inhibitor. Exemplary subjects include human beings of any age with risk factors for cardiovascular disease. Common risk factors include, but are not limited to, age, sex, weight, family history, or signs of insulin resistance such as acanthosis nigricans, hypertension, dyslipidemia, or polycystic ovary syndrome (PCOS).

As used herein, "treating" or "treatment" cover the treatment of a disease-state in a mammal, particularly in a human, and include: (a) inhibiting the disease-state, i.e., arresting it development; (b) relieving the disease-state, i.e., causing regression of the disease state; and/or (c) preventing the disease-state from occurring in a mammal, in particular, when such mammal is predisposed to the disease-state but has not yet been diagnosed as having it.

As used herein, "preventing" or "prevention" cover the preventive treatment (i.e., prophylaxis and/or risk reduction) of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" or "reducing risk" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit MPO and/or to prevent or treat the disorders listed herein. When applied to a combination, the term refers to combined amounts of the active ingredients that result in the preventive or therapeutic effect, whether administered in combination, serially, or simultaneously.

V. Pharmaceutical Compositions, Formulations and Combinations

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., HMG-CoA reductase inhibitors, antihypertensives or other pharmaceutically active material.

The compounds of the present invention may be employed in combination with other suitable therapeutic agents useful in the treatment of the aforementioned diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The compounds of the present invention may be employed in combination with additional therapeutic agent(s) selected from one or more, preferably one to three, of the following therapeutic agents in treating atherosclerosis: anti-hyperlipidemic agents, plasma HDL-raising agents, anti-hypercholesterolemic agents, cholesterol biosynthesis inhibitors (such as HMG CoA reductase inhibitors), LXR agonist, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, β-blockers, anti-diabetes agents, angiotensin II antagonists, angiotensin converting enzyme inhibitors, platelet aggregation inhibitors, fibrinogen receptor antagonists, aspirin and fabric acid derivatives.

The compounds of the present invention may be employed in combination with additional therapeutic agent(s) selected from one or more, preferably one to three, of the following therapeutic agents in treating cholesterol biosynthesis inhibitor, particularly an HMG-CoA reductase inhibitor. Examples of suitable HMG-CoA reductase inhibitors include, but are not limited to, lovastatin, simvastatin, pravastatin, fluvastatin, atorvastatin, and rosuvastatin.

The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art.

The compounds of the invention may be used in combination with one or more, preferably one to three, of the following anti-diabetic agents depending on the desired target therapy. Studies indicate that diabetes and hyperlipidemia modulation can be further improved by the addition of a second agent to the therapeutic regimen.

Examples of anti-diabetic agents include, but are not limited to, sulfonylureas (such as chlorpropamide, tolbutamide, acetohexamide, tolazamide, glyburide, gliclazide, glynase, glimepiride, and glipizide), biguanides (such as metformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); anti-glucocorticoids; TNFα inhibitors; dipeptidyl peptidase IV (DPP4) inhibitor (such as sitagliptin, saxagliptin), GLP-1 agonists or analogs (such as exenatide), α-glucosidase inhibitors (such as acarbose, miglitol, and voglibose), pramlintide (a synthetic analog of the human hormone amylin), other insulin secretagogues (such as repaglinide, gliquidone, and nateglinide), insulin, as well as the therapeutic agents discussed above for treating atherosclerosis.

The compounds of the invention may be used in combination with one or more, preferably one to three, of the following anti-obesity agents selected from phenylpropanolamine, phentermine, diethylpropion, mazindol, fenfluramine, dexfenfluramine, phentiramine, $β_3$-adrenoreceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving the myeloperoxidase. Such compounds may be provided in a commercial kit, for example, for use in pharmaceutical research involving myeloperoxidase activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving myeloperoxidase.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention should become apparent in the course of the above descriptions of exemplary embodiments that are given for illustration of the invention and are not intended to be limiting thereof.

VI. Examples

The following Examples have been prepared, isolated and characterized using the methods disclosed herein. The following examples demonstrate a partial scope of the invention and are not meant to be limiting of the scope of the invention.

General Synthesis Procedures:

General Route 1

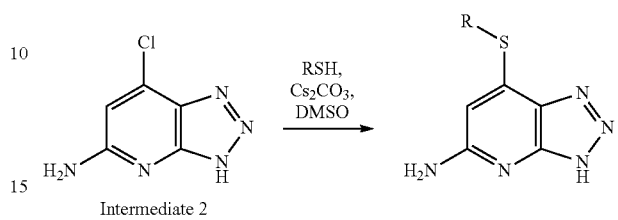

Intermediate 2

$Cs_2CO_3$ (2-5 eq) or was added to a mixture of RSH (1.5-4.0 eq) and 7-chloro-3H[1,2,3]triazolo[4,5-b]pyridin-5-amine (1.0 eq) in DMSO (0.050-0.50 M) and stirred at 75-100° C. for 1-3 days. The reaction was quenched with aqueous ammonium acetate, partially concentrated and purified by prep HPLC to yield the desired product.

General Route 2

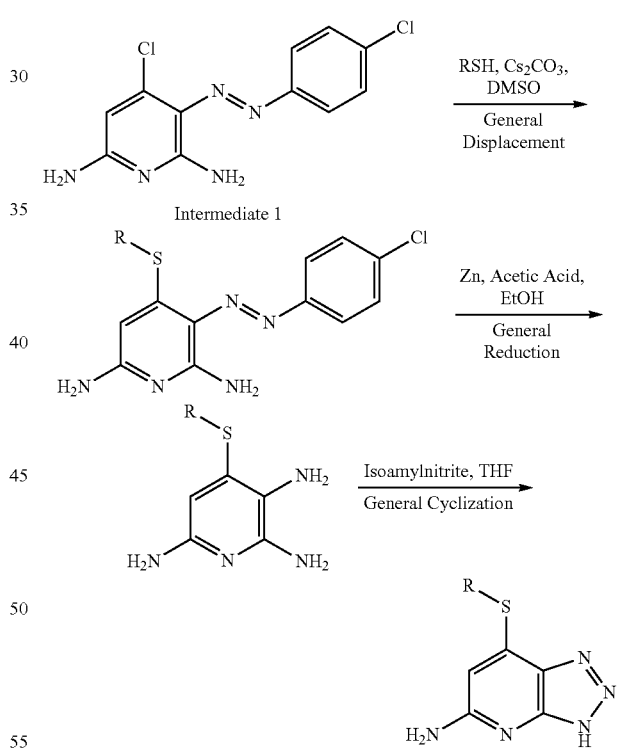

General Displacement

A mixture of (E)-4-bromo-3-((4-chlorophenyl)diazenyl) pyridine-2,6-diamine (Intermediate 1) (1.0 eq), RSH (1.0-3.0 eq) and $Cs_2CO_3$ (2.0 eq) in DMSO (0.10-0.30 M) was heated for 2 h –2 days at 60-100° C. The reaction mixture was diluted with water/brine and extracted with EtOAc. The combined organics were washed with brine, dried over $Na_2SO_4$ and concentrated in vacuo. The crude mixture was purified by column chromatography to yield the desired diazo intermediate.

General Reduction

A mixture of the diazo compound (1.0 eq) and zinc (3.0-5.0 eq) in EtOH (0.10-0.20 M) and acetic acid (5.0-10 eq) was stirred at 40-70° C. for 15 min-5 h. The mixture was filtered and concentrated. The crude material was optionally redissolved in 7.0 M NH$_3$ (0.50 M) in MeOH and concentrated. The crude product was purified by column chromatography to yield the triamine intermediate.

General Cyclization

Isoamyl nitrite (0.90-3.0 eq) was added to a mixture of the triamine (1.0 eq) in THF (0.10 M) and acetic acid (0-10 eq) and stirred at rt for 2 h-64 h. The reaction mixture was concentrated and purified by prep HPLC to yield compounds of the invention.

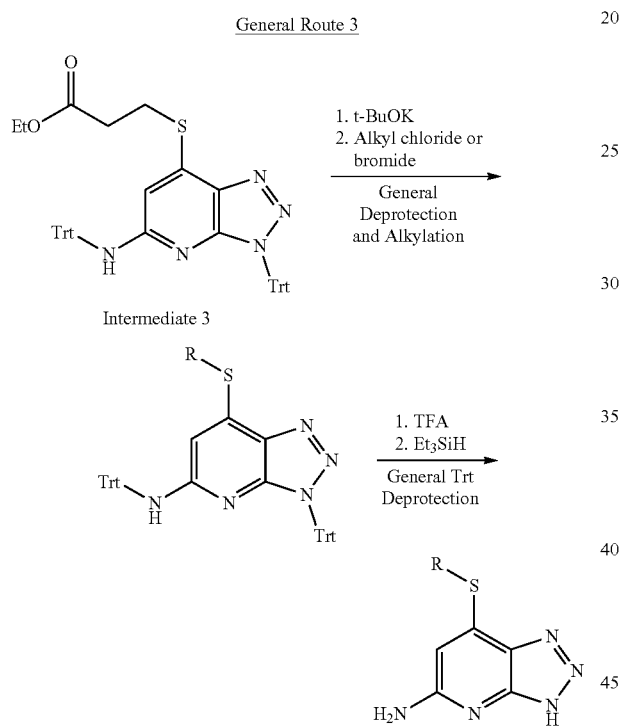

General Ethyl Propionate Deprotection and Alkylation

To a solution of Intermediate 3 (1.0 eq) in THF (0.05-2 M) was added potassium tert-butoxide (2.0 eq). The reaction mixture was stirred at rt for 30-45 min. To this reaction mixture was added alkyl halide (1-2 eq), and the resulting reaction mixture was stirred at rt for 1-12 h. The reaction mixture was concentrated, redissolved in EtOAc, washed with brine, dried over Mg$_2$SO$_4$ and concentrated in vacuo to obtain the crude desired product which was not purified before the following synthetic step.

General Trt Deprotection

TFA was added to a solution of the pyridine thioether in DCM or THF (0.10-0.50 M) and stirred at rt for 1-8 h. Triethylsilane (2-10 eq) was added and the mixture was concentrated in vacuo. The crude product was purified by preparatory HPLC to afford compounds of the invention.

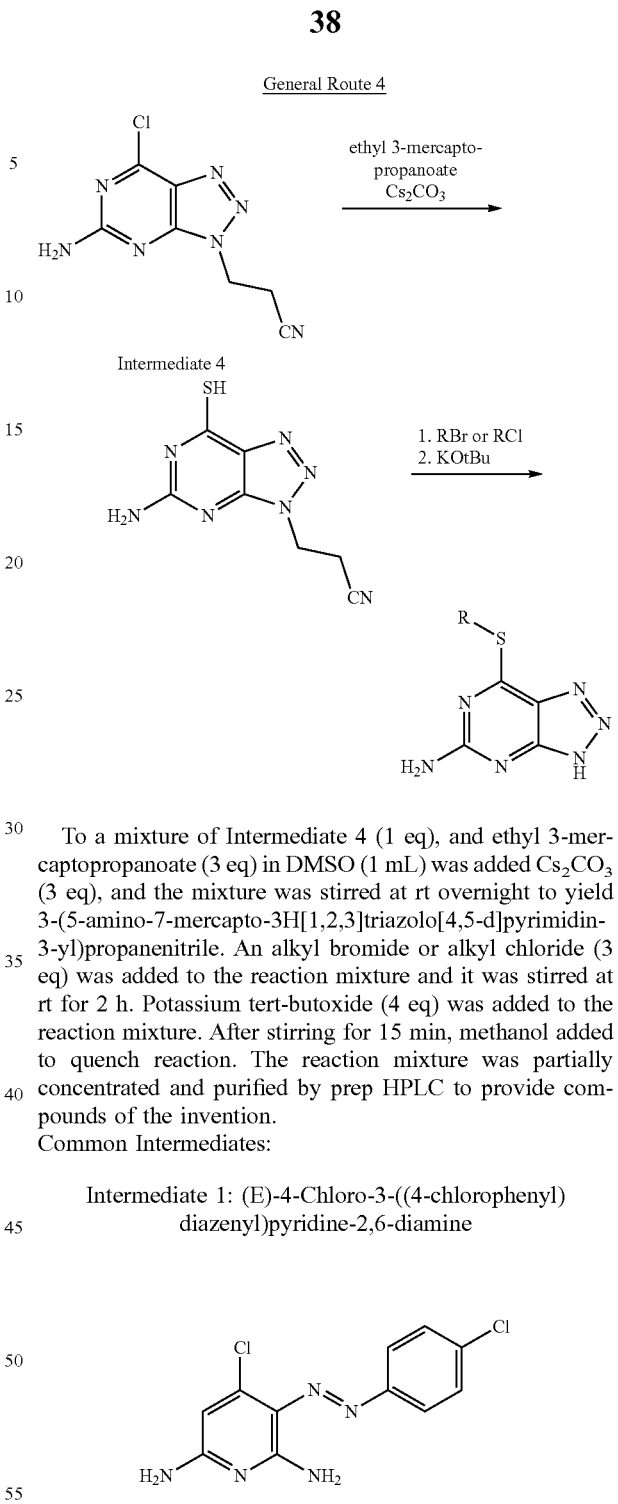

To a mixture of Intermediate 4 (1 eq), and ethyl 3-mercaptopropanoate (3 eq) in DMSO (1 mL) was added Cs$_2$CO$_3$ (3 eq), and the mixture was stirred at rt overnight to yield 3-(5-amino-7-mercapto-3H[1,2,3]triazolo[4,5-d]pyrimidin-3-yl)propanenitrile. An alkyl bromide or alkyl chloride (3 eq) was added to the reaction mixture and it was stirred at rt for 2 h. Potassium tert-butoxide (4 eq) was added to the reaction mixture. After stirring for 15 min, methanol added to quench reaction. The reaction mixture was partially concentrated and purified by prep HPLC to provide compounds of the invention.

Common Intermediates:

Intermediate 1: (E)-4-Chloro-3-((4-chlorophenyl)diazenyl)pyridine-2,6-diamine

A solution of HCl (15 mL, 91 mmol, 6N HCl) was added to 4-chloroaniline (3.4 g, 26 mmol) with vigorous stirring at 0° C. A solution of sodium nitrite (1.7 g, 24 mmol) in water (7.5 mL) was added to the flask. After stirring for 30 mins, urea (0.14 g, 2.4 mmol) was added to destroy excess NaNO$_2$.

The above solution was poured into a heterogeneous mixture of 4-chloropyridine-2,6-diamine (3.4 g, 24 mmol) in water (75 mL) and was stirred for 0.5 h. Sodium acetate (6.9 g, 84 mmol) was added and the mixture was stirred overnight. The precipitate was collected by filtration and washed thoroughly with water (5×) and dried in vacuo to yield Intermediate 1 (5.5 g, 19 mmol, 81% yield) as a yellow solid. MS (ESI) m/z 282.0 (M+H).

Intermediate 2: 7-Chloro-3H-[1,2,3]triazolo[4,5-b]pyridin-5-amine

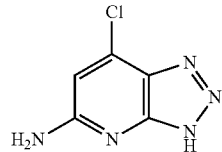 [SMILES: Nc1cc(Cl)c2nn[nH]c2n1]

Intermediate 2A: 4-Chloropyridine-2,3,6-triamine

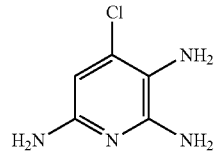

A mixture of Intermediate 1 (7.0 g, 25 mmol) and zinc (4.9 g, 74 mmol) in EtOH (120 mL)/acetic acid (7.1 mL) was stirred at 70° C. for 2 h. The mixture was filtered and concentrated. The crude product was purified by column chromatography (2.0 M NH$_3$ in MeOH/DCM, 0-20% gradient) to yield intermediate 2A (2.3 g, 14 mmol, 57% yield) as a brown solid. MS (ESI) m/z 159.1 (M+H).

Intermediate 2

Isoamyl nitrite (1.1 mL, 8.0 mmol) was added to a mixture of 4-chloropyridine-2,3,6-triamine (1.4 g, 8.8 mmol) in THF (50 mL) and acetic acid (2.5 mL), and the mixture was stirred at rt overnight. The reaction mixture was concentrated and purified by column chromatography (0% to 20% gradient, MeOH/DCM with 0.5% AcOH) to yield Intermediate 2 (600 mg, 3.5 mmol, 40% yield) as a brown solid. MS (ESI) m/z 170.1 (M+H).

Intermediate 3: ethyl 3-((3-trityl-5-(tritylamino)-3H-[1,2,3]triazolo[4,5-b]pyridin-7-yl)thio)propanoate

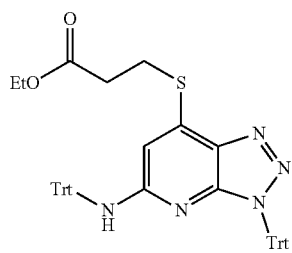

Intermediate 3A: 7-Bromo-3H-[1,2,3]triazolo[4,5-b]pyridin-5-amine

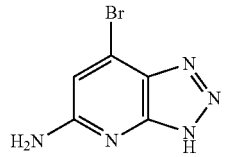 [SMILES: Nc1cc(Br)c2nn[nH]c2n1]

Intermediate 3 was synthesized from 4-bromopyridine-2,6-diamine using the procedures described in the synthesis of Intermediates 1 and 2.

Intermediate 3B: 7-Bromo-N,3-ditrityl-3H-[1,2,3]triazolo[4,5-b]pyridin-5-amine

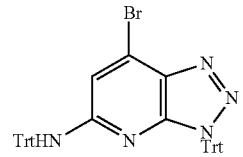

Triethylamine (2.6 mL, 18 mmol) was added to a suspension of Intermediate 3A (1.3 g, 6.1 mmol) in DCM (61 mL), followed by trityl chloride (3.4 g, 12 mmol). The reaction mixture was stirred for 1 hour at rt. The crude mixture was partially concentrated and purified by column chromatography to yield Intermediate 3B (2.7 g, 3.8 mmol, 63% yield) as a tan powder. MS (ESI) m/z 698.1/700.1 (M+H).

Intermediate 3

A mixture of Intermediate 3B (5.9 g, 8.4 mmol), (oxybis(2,1-phenylene))bis(diphenylphosphine) (0.91 g, 1.7 mmol), Pd$_2$(dba)$_3$ (0.77 g, 0.84 mmol), K$_2$CO$_3$ (3.5 g, 25 mmol) and ethyl 3-mercaptopropanoate (3.4 g, 25 mmol) in toluene (30 mL) in a heat resistant sealed vessel was evacuated and backfilled with argon (3×). The mixture was heated at 100° C. overnight. The contents of the vessel were filtered and loaded directly on a silica gel column. The product was eluted with EtOAc/Hexanes (0-30% EtOAc/Hexanes) to yield Intermediate 3 (4.9 g, 6.5 mmol, 77% yield) as a light pink solid. MS (ESI) m/z 752.3 (M+H).

Intermediate 4: 3-(5-Amino-7-chloro-3H-[1,2,3]triazolo[4,5-d]pyrimidin-3-yl)propanenitrile

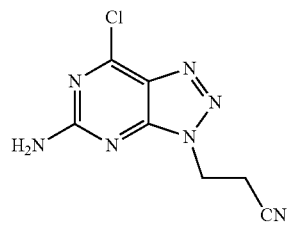 [SMILES: N#CCCn1nnc2c(Cl)nc(N)nc21]

Intermediate 4A: 3-((2,5-Diamino-6-chloropyrimidin-4-yl)amino)propanenitrile

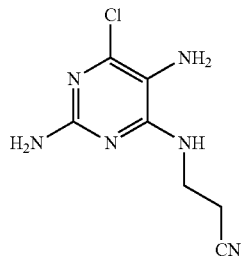 [SMILES: N#CCCNc1nc(N)nc(Cl)c1N]

A mixture of 4,6-dichloropyrimidine-2,5-diamine (prepared according to U.S. Pat. No. 4,543,255) (2.0 g, 11 mmol) and 3-aminopropionitrile (4.1 mL, 56 mmol) was heated to 100° C. and stirred 1 h. The material was cooled to rt, concentrated to yield 3-(2,5-diamino-6-chloropyrimidin-4-ylamino)propanenitrile (2.4 g, 11 mmol, 100% yield) which was used in the subsequent step without purification. MS (ESI) m/z 212.9 (M+H.

Intermediate 4

To a solution of Intermediate 4A (2.4 g, 11 mmol) in AcOH (9.3 mL)/water (28 mL) was added $NaNO_2$ (0.93 g, 13 mmol) in water (19 mL) at 0° C. After 10 min, the reaction mixture was diluted with EtOAc and adjusted to pH=6 using sat. aq. $NaHCO_3$. The organic layer was washed with brine, dried over $MgSO_4$, filtered and concentrated. The residue was purified by filtration through a silica plug with EtOAc as the eluent, and the resulting solution was concentrated to furnish Intermediate 4 (1.1 g, 5.0 mmol, 44% yield). MS (ESI) m/z 224.4 (M+H). $^1$H NMR (400 MHz, DMSO-$d_6$) δ 7.76 (br. s., 2H), 4.67 (t, J=6.3 Hz, 2H), 3.22 (t, J=6.3 Hz, 2H).

Example 1: 7-(Benzylthio)-3H-[1,2,3]triazolo[4,5-b]pyridin-5-amine

To a mixture of Intermediate 2 (15 mg, 0.088 mmol), and phenylmethanethiol (22 mg, 0.18 mmol) in DMSO (1 mL) was added cesium carbonate (58 mg, 0.18 mmol), and the reaction mixture was stirred at 85° C. for 10 h. The crude mixture was filtered, and the filtrate was diluted with MeOH and purified by preparatory HPLC to obtain the title compound (19 mg, 0.069 mmol, 78% yield) as a yellow solid. MS (ESI) m/z 258.2 (M+H). $^1$H NMR (500 MHz, $CD_3OD$) δ 8.25 (d, J=7.2 Hz, 2H), 8.21-8.00 (m, 3H), 7.45 (br. s., 1H), 5.34-5.22 (m, 2H).

The following compounds were prepared in a manner similar to experimental procedures that are described in Example 1 using Intermediate 2 and the appropriate thiol as starting materials:

| Ex. No. | Structure | Name | Analytical Data |
|---|---|---|---|
| 2 | 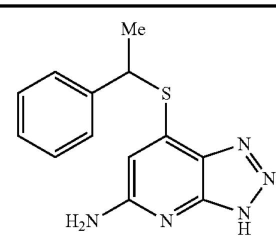 | 7-((1-phenylethyl)thio)-3H-[1,2,3]triazolo[4,5-b]pyridin-5-amine | MS(ESI) 272.1 (M + H)$^+$. $^1$H NMR (500 MHz, $CD_3OD$)) δ 7.55-7.49 (m, 2H), 7.39-7.33 (m, 2H), 7.31-7.24 (m, 1H), 6.63 (s, 1H), 5.02 (q, J = 6.9 Hz, 1H), 1.78 (d, J = 6.9 Hz, 3H). |
| 3 | 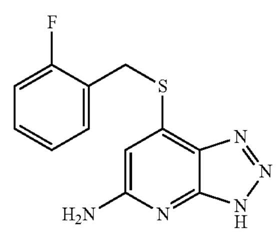 [SMILES: Nc1cc(SCc2ccccc2F)c2nn[nH]c2n1] | 7-((2-fluorobenzyl)thio)-3H-[1,2,3]triazolo[4,5-b]pyridin-5-amine | MS(ESI) 276.1 (M + H)$^+$. $^1$H NMR (500 MHz, $CD_3OD$) δ 7.53 (d, J = 1.4 Hz, 1H), 7.37 (d, J = 8.0 Hz, 1H), 7.25-7.09 (m, 2H), 6.72 (s, 1H), 4.56 (s, 2H). |
| 4 | 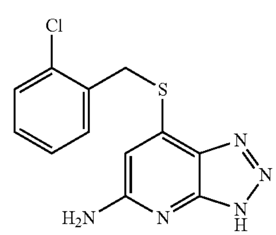 [SMILES: Nc1cc(SCc2ccccc2Cl)c2nn[nH]c2n1] | 7-((2-chlorobenzyl)thio)-3H-[1,2,3]triazolo[4,5-b]pyridin-5-amine | MS(ESI) 292.2 (M + H)$^+$. $^1$H NMR (500 MHz, $CD_3OD$) δ 7.62-7.54 (m, 1H), 7.47 (s, 1H), 7.38-7.24 (m, 2H), 6.71 (s, 1H), 4.64 (s, 2H). |

| Ex. No. | Structure | Name | Analytical Data |
|---|---|---|---|
| 5 | 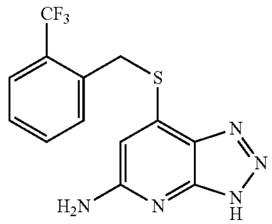 | 7-((2-(trifluoromethyl) benzyl)thio)-3H-[1,2,3] triazolo[4,5-b]pyridin-5-amine | MS(ESI) 326.2 (M + H)+. 1H NMR (500 MHz, CD3OD) δ 7.83-7.70 (m, 2H), 7.68-7.61 (m, 1H), 7.58-7.50 (m, 1H), 6.72-6.61 (m, 1H), 4.70 (s, 2H). |
| 6 | 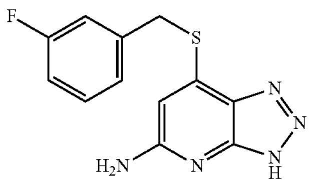 [SMILES: Nc1cc(SCc2cccc(F)c2)c2nn[nH]c2n1] | 7-((3-fluorobenzyl) thio)-3H-[1,2,3]triazolo [4,5-b]pyridin-5-amine | MS(ESI) 276.0 (M + H)+. 1H NMR (500 MHz, CD3OD) δ 7.44-7.29 (m, 2H), 7.27-7.20 (m, 1H), 7.11-6.98 (m, 1H), 6.66 (s, 1H), 4.54 (s, 2H). |
| 7 | 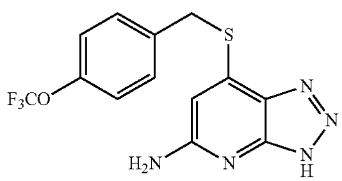 [SMILES: Nc1cc(SCc2ccc(OC(F)(F)F)cc2)c2nn[nH]c2n1] | 7-((4-(trifluoromethoxy) benzyl)thio)-3H-[1,2,3] triazolo[4,5-b]pyridin-5-amine | MS(ESI) 342.0 (M + H)+. 1H NMR (500 MHz, CD3OD) δ 7.59 (d, J = 8.0 Hz, 2H), 7.28 (d, J = 8.0 Hz, 2H), 6.66 (s, 1H), 4.56 (s, 2H). |
| 8 | 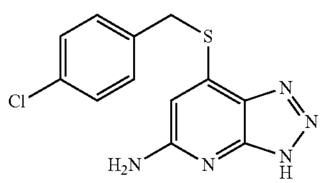 [SMILES: Nc1cc(SCc2ccc(Cl)cc2)c2nn[nH]c2n1] | 7-((4-chlorobenzyl) thio)-3H-[1,2,3]triazolo [4,5-b]pyridin-5-amine | MS(ESI) 292.0/294.0 (M + H)+. 1H NMR (500 MHz, CD3OD) δ 7.53-7.43 (m, 1H), 7.41-7.33 (m, 1H), 6.65 (s, 1H), 4.51 (s, 2H). |
| 9 | 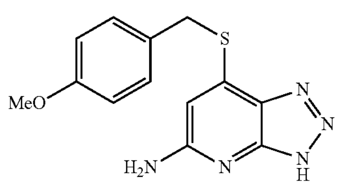 [SMILES: COc1ccc(CSc2cc(N)nc3[nH]nnc23)cc1] | 7-((4-methoxybenzyl) thio)-3H-[1,2,3]triazolo [4,5-b]pyridin-5-amine | MS(ESI) 288.15 (M + H)+. 1H NMR (500 MHz, CD3OD) δ 7.41-7.26 (m, 2H), 6.91-6.82 (m, 2H), 6.52-6.41 (m, 1H), 4.37 (s, 2H), 3.79 (s, 3H). |

Example 10: 7-((2,6-Difluorobenzyl)thio)-3H-[1,2,3]triazolo[4,5-b]pyridin-5-amine

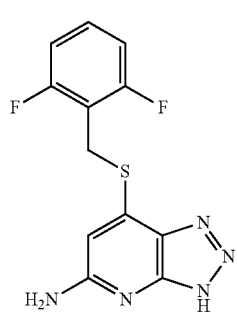 [SMILES: Nc1cc(SCc2c(F)cccc2F)c2nn[nH]c2n1]

Example 10A: (E)-3-((4-Chlorophenyl)diazenyl)-4-((2,6-difluorobenzyl)thio)pyridine-2,6-diamine

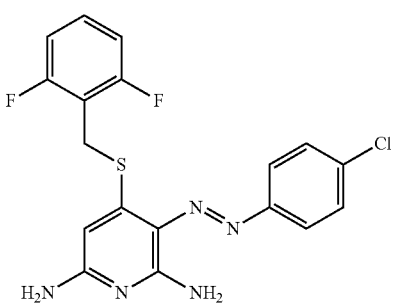 [SMILES: Nc1cc(SCc2c(F)cccc2F)c(/N=N/c2ccc(Cl)cc2)c(N)n1]

A mixture of Intermediate 2A, (2,6-difluorophenyl)methanethiol (230 mg, 1.4 mmol) and $Cs_2CO_3$ (1800 mg, 5.7 mmol) in DMSO (2 mL) was heated for 1 h at 90° C. The mixture was diluted with water, and the mixture was extracted with EtOAc. The combined organics were washed with 1N HCl and brine, dried over $MgSO_4$ and concentrated. The crude was purified by column chromatography to yield Example 10A as an impure brown oil. MS (ESI) m/z 406.2/408.2.

Example 10B: 4-((2,6-Difluorobenzyl)thio)pyridine-2,3,6-triamine

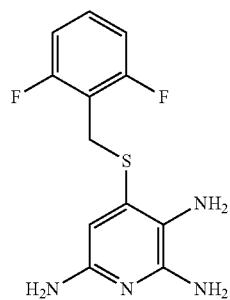 [SMILES: Nc1cc(SCc2c(F)cccc2F)c(N)c(N)n1]

To a solution of 10A (700 mg, 1.7 mmol) in MeOH (50 mL) was added zinc powder (340 mg, 5.2 mmol) followed by glacial acetic acid (0.296 mL, 5.17 mmol). The resulting reaction mixture was heated at 60° C. for 2 h. The reaction mixture was cooled to rt and filtered through a pad of celite. The filtrates were combined and concentrated. The crude product was dissolved in 5.0 mL of 7.0 M $NH_3$ in MeOH and concentrated. The crude product was purified by column chromatography (2.0 M $NH_3$ in MeOH/$CH_2Cl_2$, 0-20% gradient) to yield Example 10B (300 mg, 1.1 mmol, 62% yield). MS (ESI) m/z 283.3.

Example 10

To a solution of 10B (280 mg, 0.98 mmol) in THF (10 mL) was added a solution of isoamyl nitrite (0.13 mL, 0.93 mmol). The resulting solution was stirred at rt overnight. The mixture was concentrated and purified by preparatory HPLC to yield Example 10 (8 mg, 0.079 mmol, 2.3% yield) as a purple solid. MS(ESI) m/z 294.0 (M+H). $^1$H NMR (500 MHz, $CD_3OD$) δ 7.48-7.34 (m, 1H), 7.05 (s, 2H), 6.83-6.74 (m, 1H), 4.57 (s, 2H).

Example 11: 7-((2,6-Dichlorobenzyl)thio)-3H-[1,2,3]triazolo[4,5-b]pyridin-5-amine

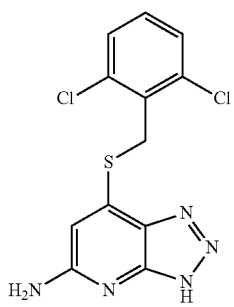

KOtBu (12 mg, 0.11 mmol) was added to a solution of Intermediate 3 (40 mg, 0.053 mmol) in THF (1 mL). After stirring for 1 h, 1,3-dichloro-2-(chloromethyl)benzene (10 mg, 0.053 mmol) was added to the reaction mixture. The reaction mixture was stirred for 3 h. DCM (1 mL), TFA (2 mL) and triethysilane (0.048 mL, 0.030 mmol) were added to the reaction mixture and stirred for 20 min at rt. The mixture was concentrated and purified by preparatory HPLC to yield Example 11 (13 mg, 0.040 mmol, 75% yield). MS (ESI) 326.1 (M+H)+. $^1$H NMR (500 MHz, DMSO-$d_6$) δ 7.57 (d, J=8.0 Hz, 2H), 7.48-7.37 (m, 1H), 6.61 (br. s., 1H), 4.71 (s, 2H).

Example 12: 2-(((5-Amino-3H-[1,2,3]triazolo[4,5-b]pyridin-7-yl)thio)methyl)-4-(1H-pyrazol-1-yl)benzonitrile

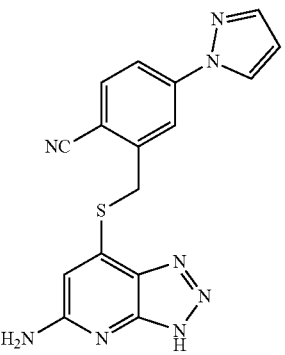 [SMILES: N#Cc1ccc(-n2cccn2)cc1CSc1cc(N)nc2[nH]nnc12]

Example 12A: 2-Methyl-4-(1H-pyrazol-1-yl)benzonitrile

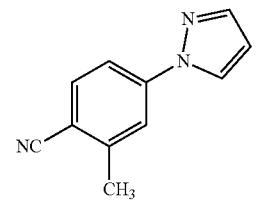

4-Bromo-2-methylbenzonitrile (300 mg, 1.5 mmol), 1H-pyrazole (830 mg, 12 mmol). CuI (440 mg, 2.3 mmol), $K_2CO_3$ (630 mg, 4.6 mmol), quinolin-8-ol (330 mg, 2.3 mmol) and DMSO (2 mL) were added to a 5 mL vial. The vial was quickly purged with argon and sealed, and the contents were stirred at 100° C. overnight. The reaction mixture was diluted with DCM (5 mL) and loaded onto a 40 g silica column. The column was eluted with EtOAc/Hexanes (0-100%). The fractions of interest were pooled and concentrated to obtain Example 12A (100 mg, 0.56 mmol, 36% yield) as a white solid. $^1$H NMR (400 MHz, $CDCl_3$) δ 8.05-7.95 (m, 1H), 7.82-7.66 (m, 3H), 7.64-7.52 (m, 1H), 6.52 (dd, J=2.6, 1.8 Hz, 1H), 2.62 (s, 3H).

Example 12B: 2-(Bromomethyl)-4-(1H-pyrazol-1-yl)benzonitrile

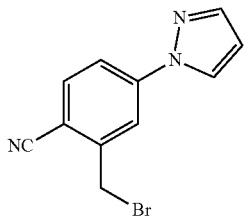 [SMILES: N#Cc1ccc(-n2cccn2)cc1CBr]

A mixture of Example 12A (100 mg, 0.55 mmol), NBS (120 mg, 0.66 mmol) and AIBN (27 mg, 0.16 mmol) in ACN (2 mL) was subjected to microwave irradiation for 1 hour at 170° C. The mixture was diluted with DCM, washed with NaHCO$_3$ and brine, dried over MgSO$_4$ and concentrated to obtain Example 12B (85 mg, 0.32 mmol, 59% yield) as a yellow solid. The crude was used in subsequent step without further purification. MS (ESI) 262.0/264.0 (M+H)$^+$.

Example 12

Example 12 was synthesized from Intermediate 3 and Example 12B as described in Example 11. MS(ESI) 349.1 (M+H)$^+$. $^1$H NMR (500 MHz, DMSO-d$_6$) δ 8.64 (s, 1H), 8.23 (s, 1H), 8.09-7.96 (m, 2H), 7.85 (s, 1H), 6.65 (br. s., 1H), 6.54 (br. s., 1H), 4.75 (s, 2H).

Example 14: 7-((4-(Benzylamino)-1-phenylbutyl)thio)-3H-[1,2,3]triazolo[4,5-b]pyridin-5-amine

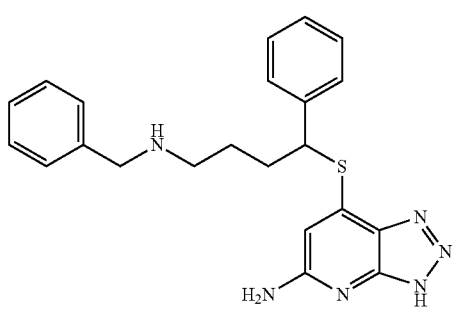 [SMILES: Nc1cc(SC(CCCNCc2ccccc2)c2ccccc2)c2nn[nH]c2n1]

Example 14A: N-Benzyl-4-hydroxy-4-phenylbutanamide

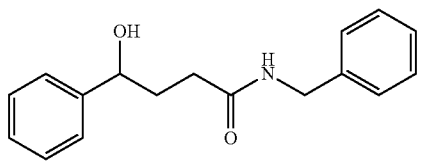 [SMILES: O=C(CCC(O)c1ccccc1)NCc1ccccc1]

A mixture of 5-phenyldihydrofuran-2(3H)-one (500 mg, 3.1 mmol) and phenylmethanamine (330 mg, 3.1 mmol) in EtOH (4 mL) were placed in a vessel in a microwave and heated for 90 min at 150° C. The reaction mixture was concentrated to obtain Example 14A as a yellow solid. $^1$H NMR (500 MHz, CDCl$_3$) δ 7.37-7.08 (m, 10H), 4.80-4.63 (m, 2H), 4.37 (d, J=5.8 Hz, 1H), 2.63-2.52 (m, 1H), 2.35-2.25 (m, 1H), 2.12-1.76 (m, 3H).

Example 14B: 4-(Benzylamino)-1-phenylbutan-1-ol

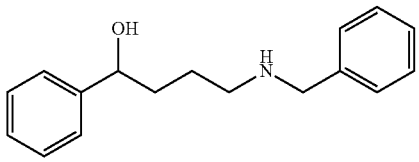 [SMILES: OC(CCCNCc1ccccc1)c1ccccc1]

BH$_3$-THF (5.3 mL, 5.3 mmol, 1.0 M in THF) was added to a mixture of N-benzyl-4-hydroxy-4-phenylbutanamide (480 mg, 1.8 mmol) in THF (5 mL). The resulting reaction mixture was heated at reflux in a sealed vessel overnight. Another portion of BH$_3$-THF (5.3 mL, 5.3 mmol) added and the reaction mixture was refluxed overnight. HCl (10 mL, 1 N) was added and the reaction mixture was heated at 50° C. for 2 h. NaHCO$_3$ (40 mL, saturated aqueous) was added and the mixture was extracted with EtOAc (3×). The combined organics were washed with brine, dried over MgSO$_4$ and concentrated to obtain Example 14B (380 mg, 1.5 mmol, 84% yield) as a colorless liquid. MS(ESI) 256.3 (M+H)$^+$.

Example 14C: tert-Butyl benzyl(4-hydroxy-4-phenylbutyl)carbamate

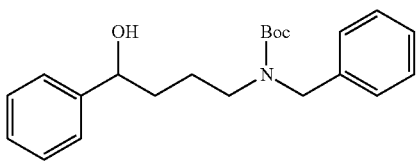 [SMILES: CC(C)(C)OC(=O)N(CCCC(O)c1ccccc1)Cc1ccccc1]

To a mixture of 4-(benzylamino)-1-phenylbutan-1-ol (380 mg, 1.5 mmol) in DCM (10 mL) was added BOC$_2$O (0.86 mL, 3.7 mmol). The reaction mixture was stirred overnight. The reaction mixture was concentrated to 2 mL and loaded onto a 40 g silica gel column and eluted with EtOAc/hexanes (0-100%) to obtain Example 14C (370 mg, 1.0 mmol, 70% yield). MS(ESI) 356.3 (M+H)$^+$.

Example 14D: tert-Butyl benzyl(4-chloro-4-phenylbutyl)carbamate

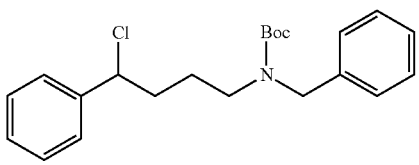 [SMILES: CC(C)(C)OC(=O)N(CCCC(Cl)c1ccccc1)Cc1ccccc1]

To a mixture of tert-butyl benzyl(4-hydroxy-4-phenylbutyl)carbamate (88 mg, 0.25 mmol) in DCM (2 mL) was added thionyl chloride (0.018 mL, 0.25 mmol). The reaction mixture was stirred at room temperature for 2 h. The mixture was concentrated in vacuo and the crude product was used in the subsequent reaction without further purification. MS(ESI) 374.3 (M+H)+.

Example 14

Example 14 was synthesized using conditions found in Example 11. MS(ESI) 405.2 (M+H)+. ¹H NMR (500 MHz, CD₃OD) δ 7.41 (m, 7H), 7.34-7.18 (m, 3H), 6.48-6.32 (m, 1H), 5.17-5.02 (m, 1H), 4.17-4.00 (m, 2H), 3.06-2.94 (m, 2H), 2.24-2.04 (m, 2H), 1.88-1.63 (m, 2H).

Example 15: 7-((3-(Pyrrolidin-1-ylmethyl)benzyl)thio)-3H-[1,2,3]triazolo[4,5-b]pyridin-5-amine

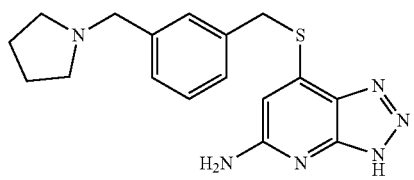 [SMILES: Nc1cc(SCc2cccc(CN3CCCC3)c2)c2nn[nH]c2n1]

Example 15A: (3-(Pyrrolidin-1-ylmethyl)phenyl)methanol

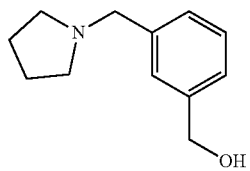 [SMILES: OCc1cccc(CN2CCCC2)c1]

To a solution of 3-(pyrrolidin-1-ylmethyl)benzoic acid, HCl (340 mg, 1.4 mmol) in THF (3 mL) was added BH₃·THF (4.2 mL, 4.2 mmol, 1.0 M in THF). The reaction mixture was heated at 90° C. in a sealed tube overnight. The mixture was cooled to room temperature, diluted with 1N HCl and stirred for 1 h. After neutralization with NaHCO₃ (sat'd aqueous), the mixture was extracted with EtOAc (3×). The combined organics were washed with brine, dried over MgSO₄ and concentrated to obtain Example 15A (140 mg, 0.73 mmol, 52% yield) as a white solid. ¹H NMR (400 MHz, CDCl₃) δ 7.40-7.20 (m, 4H), 4.68 (s, 2H), 3.67-3.59 (m, 2H), 2.58-2.45 (m, 4H), 1.90-1.69 (m, 4H).

Example 15B: 1-(3-(Chloromethyl)benzyl)pyrrolidine

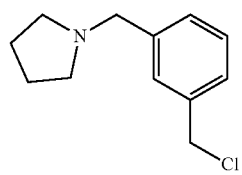 [SMILES: ClCc1cccc(CN2CCCC2)c1]

To a mixture of (3-(pyrrolidin-1-ylmethyl)phenyl)methanol (140 mg, 0.73 mmol) in DCM (1 mL) was added thionyl chloride (0.13 mL, 1.83 mmol). The reaction mixture was stirred at room temperature for 15 min and then concentrated in vacuo to obtain Example 15B (130 mg, 0.61 mmol, 83% yield) as a white solid. ¹H NMR (400 MHz, CDCl₃) δ 7.74-7.63 (m, 2H), 7.51-7.40 (m, 2H), 4.61 (s, 2H), 4.21 (d, J=5.7 Hz, 2H), 3.66 (m, 2H), 2.92-2.75 (m, 2H), 2.34-2.17 (m, 2H), 2.05 (m, 2H).

Example 15

Example 15 was synthesized using conditions found in Example 11. MS(ESI) 341.2 (M+H)+. ¹H NMR (500 MHz, DMSO-d₆) δ 7.66-7.52 (m, 2H), 7.48-7.31 (m, 2H), 6.50 (s, 1H), 4.49 (s, 2H), 4.35-4.21 (m, 2H), 3.28 (br. s., 2H), 3.03 (br. s., 2H), 2.08-1.93 (m, 2H), 1.83 (br. s., 2H).

Example 16: 7-(((3-Cyclopropyl-4-fluoro-1-methyl-1H-pyrazol-5-yl)methyl)thio)-3H-[1,2,3]triazolo[4,5-b]pyridin-5-amine

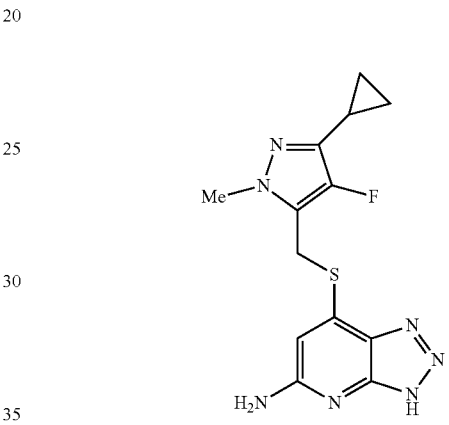

Example 16A: (3-Cyclopropyl-4-fluoro-1-methyl-1H-pyrazol-5-yl)methanol

SELECTFLUOR® (770 mg, 2.2 mmol) was added portionwise at 0° C. over 5 min to a solution of (3-cyclopropyl-1-methyl-1H-pyrazol-5-yl)methanol (300 mg, 2.0 mmol) in Acn (10 mL). The reaction mixture was stirred at rt for 3 h and then concentrated in vacuo. The residue was redissolved in EtOAc/water. The combined organics were washed with brine, dried over Na₂SO₄ and concentrated in vacuo. The crude product was purified by flash chromatography (loading in chloroform, 0% to 50% ethyl acetate in hexane over 10 min using a 4 g silica gel cartridge) to yield Example 16A (64 mg, 0.38 mmol, 19% yield) as a clear oil. ¹H NMR (400 MHz, CDCl₃) δ 4.60-4.52 (m, 2H), 3.76-3.69 (m, 3H), 1.87-1.72 (m, 1H), 0.93-0.76 (m, 4H).

Example 16

Example 16 was synthesized using conditions found in Example 11. MS(ESI) 320.1 (M+H)+. ¹H NMR (500 MHz, CD₃OD) δ 6.59 (s, 1H), 4.54 (s, 2H), 3.77 (s, 3H), 1.79 (m, 1H), 0.90-0.82 (m, 2H), 0.82-0.72 (m, 2H).

Example 17: 7-(((4-Fluoro-1-methyl-3-phenyl-1H-pyrazol-5-yl)methyl)thio)-3H-[1,2,3]triazolo[4,5-b]pyridin-5-amine

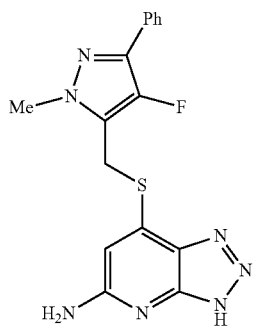

Example 17 was synthesized from (1-methyl-3-phenyl-1H-pyrazol-5-yl)methanol using conditions found in Example 18. MS(ESI) 356.2 (M+H)$^+$. $^1$H NMR (500 MHz, DMSO-d$_6$) δ 7.70 (d, J=7.4 Hz, 2H), 7.43 (t, J=7.6 Hz, 2H), 7.38-7.29 (m, 1H), 6.63 (s, 2H), 6.52 (s, 1H), 4.72 (s, 2H), 3.89 (s, 3H).

The following compounds were prepared in a manner similar to experimental procedures that are described in Example 11 using ethyl 3-((3-trityl-5-(tritylamino)-3H-[1,2,3]triazolo[4,5-b]pyridin-7-yl)thio)propanoate and the appropriate alkyl chloride or bromide as starting material. The alkyl chloride and bromide can be prepared from the corresponding ester or alcohol using standard procedures.

| Ex. No. | Structure | Name | Analytical Data |
| --- | --- | --- | --- |
| 18 | 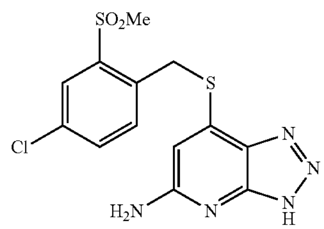 [SMILES: CS(=O)(=O)c1cc(Cl)ccc1CSc1cc(N)nc2[nH]nnc12] | 7-((4-chloro-2-(methylsulfonyl)benzyl)thio)-3H-[1,2,3]triazolo[4,5-b]pyridin-5-amine | MS(ESI) 370.2 (M + H)$^+$. $^1$H NMR (500 MHz, DMSO-d$_6$) δ 8.05-7.95 (m, 1H), 7.81 (m, 1H), 7.77-7.66 (m, 1H), 6.52 (br. s., 1H), 4.95 (s, 2H), 3.47 (s, 3H). |
| 19 | 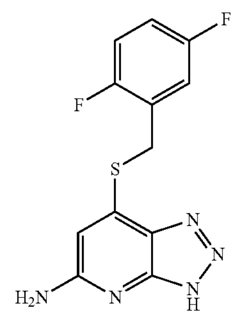 [SMILES: Nc1cc(SCc2cc(F)ccc2F)c2nn[nH]c2n1] | 7-((2,5-difluorobenzyl)thio)-3H-[1,2,3]triazolo[4,5-b]pyridin-5-amine | MS(ESI) 294.2 (M + H)$^+$. $^1$H NMR (500 MHz, DMSO-d$_6$) δ 7.40 (m, 1H), 7.32 (m, 1H), 7.25-7.15 (m, 1H), 6.53 (s, 1H), 4.52 (s, 2H). |
| 20 | 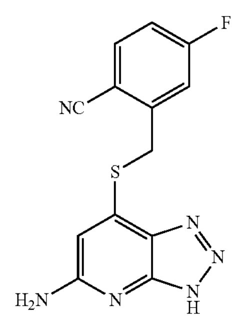 [SMILES: N#Cc1ccc(F)cc1CSc1cc(N)nc2[nH]nnc12] | 2-(((5-amino-3H-[1,2,3]triazolo[4,5-b]pyridin-7-yl)thio)methyl)-4-fluorobenzonitrile | MS(ESI) 301.2 (M + H)$^+$. $^1$H NMR (500 MHz, DMSO-d$_6$) δ 8.08-7.93 (m, 1H), 7.62-7.51 (m, 1H), 7.45-7.33 (m, 1H), 6.73-6.59 (m, 2H), 6.52-6.41 (m, 1H), 4.69 (s, 2H). |
| 21 | 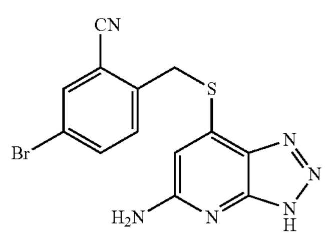 [SMILES: N#Cc1cc(Br)ccc1CSc1cc(N)nc2[nH]nnc12] | 2-(((5-amino-3H-[1,2,3]triazolo[4,5-b]pyridin-7-yl)thio)methyl)-5-bromobenzonitrile | MS(ESI) 361.1/363.1 (M + H)$^+$. $^1$H NMR (500 MHz, DMSO-d$_6$) δ 8.20 (d, J = 1.9 Hz, 1H), 7.93-7.83 (m, 1H), 7.58 (d, J = 8.3 Hz, 1H), 6.58 (br. s., 2H), 6.45 (s, 1H), 4.68 (s, 2H). |

| Ex. No. | Structure | Name | Analytical Data |
|---|---|---|---|
| 22 | 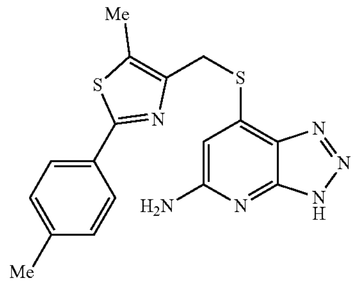 [SMILES: Cc1ccc(-c2nc(CSc3cc(N)nc4[nH]nnc34)c(C)s2)cc1] | 7-(((5-methyl-2-(p-tolyl)thiazol-4-yl)methyl)thio)-3H-[1,2,3]triazolo[4,5-b]pyridin-5-amine | MS(ESI) 419 (M + H)+. 1H NMR (500 MHz, DMSO-d6) δ 7.77 (d, J = 8.0 Hz, 2H), 7.29 (d, J = 8.0 Hz, 2H), 6.71 (br. s., 1H), 4.58 (s, 2H), 2.51 (s, 3H), 2.36 (s, 3H) |
| 23 | 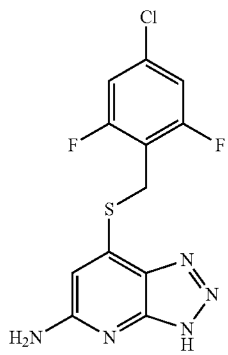 [SMILES: Nc1cc(SCc2c(F)cc(Cl)cc2F)c2nn[nH]c2n1] | 7-((4-chloro-2,6-difluorobenzyl)thio)-3H-[1,2,3]triazolo[4,5-b]pyridin-5-amine | MS(ESI) 328.1 (M + H)+. 1H NMR (500 MHz, DMSO-d6) δ 7.43 (d, J = 7.7 Hz, 2H), 6.61 (br. s., 2H), 6.53 (s, 1H), 4.53 (s, 2H) |
| 24 | 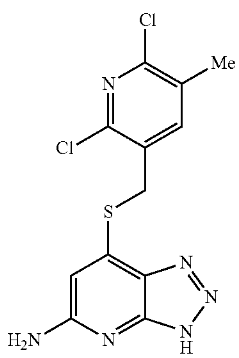 [SMILES: Cc1cc(CSc2cc(N)nc3[nH]nnc23)c(Cl)nc1Cl] | 7-(((2,6-dichloro-5-methylpyridin-3-yl)methyl)thio)-3H-[1,2,3]triazolo[4,5-b]pyridin-5-amine | MS(ESI) 341.1 (M + H)+. 1H NMR (500 MHz, DMSO-d6) δ 15.24 (br. s., 1H), 8.02 (s, 1H), 6.63 (br. s., 2H), 6.43 (br. s., 1H), 4.54 (s, 2H), 2.31 (s, 3H) |
| 25 | 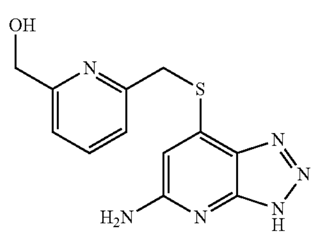 [SMILES: Nc1cc(SCc2cccc(CO)n2)c2nn[nH]c2n1] | (6-(((5-amino-3H-[1,2,3]triazolo[4,5-b]pyridin-7-yl)thio)methyl)pyridin-2-yl)methanol | MS(ESI) 289.1 (M + H)+. 1H NMR (500 MHz, DMSO-d6) δ 7.78 (m, 1H), 7.38 (m, 2H), 6.52 (br. s., 3H), 5.42 (br. s., 1H), 4.61-4.48 (m, 4H) |
| 26 | 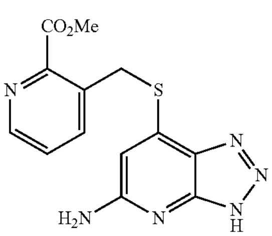 [SMILES: COC(=O)c1ncccc1CSc1cc(N)nc2[nH]nnc12] | methyl 3-(((5-amino-3H-[1,2,3]triazolo[4,5-b]pyridin-7-yl)thio)methyl)picolinate | MS(ESI) 317.3 (M + H)+. 1H NMR (500 MHz, DMSO-d6) δ 8.59 (m, 1H), 8.04 (m, 1H), 7.58 (m, 1H), 6.49 (br. s., 1H), 4.78 (s, 2H), 4.04-3.84 (m, 3H). |

-continued

| Ex. No. | Structure | Name | Analytical Data |
|---|---|---|---|
| 27 | 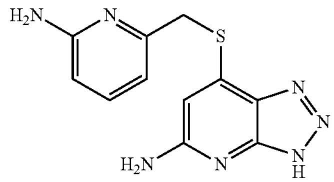 [SMILES: Nc1cccc(CSc2cc(N)nc3[nH]nnc23)n1] | 7-(((6-aminopyridin-2-yl)methyl)thio)-3H-[1,2,3]triazolo[4,5-b]pyridin-5-amine | MS(ESI) 274.2 (M + H)$^+$. $^1$H NMR (500 MHz, DMSO-$d_6$) δ 7.69 (s, 2H), 7.25-7.09 (m, 1H), 6.79-6.50 (m, 3H), 4.40 (s, 2H). |
| 28 | 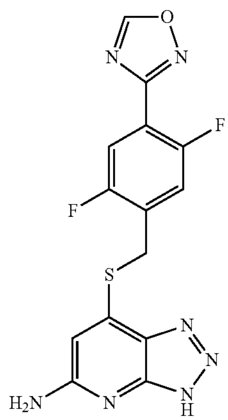 [SMILES: Nc1cc(SCc2cc(F)c(-c3ncon3)cc2F)c2nn[nH]c2n1] | 7-((2,5-difluoro-4-(1,2,4-oxadiazol-3-yl)benzyl)thio)-3H-[1,2,3]triazolo[4,5-b]pyridin-5-amine | MS(ESI) 362.1 (M + H)$^+$. $^1$H NMR (500 MHz, DMSO-$d_6$) δ 9.87-9.69 (m, 1H), 7.94-7.79 (m, 1H), 7.72-7.56 (m, 1H), 6.73-6.58 (m, 2H), 6.52-6.35 (m, 1H), 4.61 (s, 2H). |
| 29 | 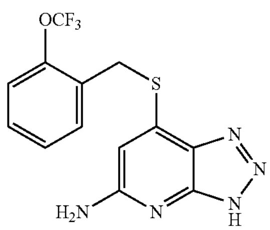 [SMILES: Nc1cc(SCc2ccccc2OC(F)(F)F)c2nn[nH]c2n1] | 7-((2-(trifluoromethoxy)benzyl)thio)-3H-[1,2,3]triazolo[4,5-b]pyridin-5-amine | MS(ESI) 342.1 (M + H)$^+$ $^1$H NMR (500 MHz, DMSO-$d_6$) δ 7.96 (s, 1H), 7.63 (d, J = 7.7 Hz, 1H), 7.52-7.31 (m, 3H), 6.57 (br. s., 2H), 6.48 (s, 1H), 4.55 (s, 2H) |
| 30 | 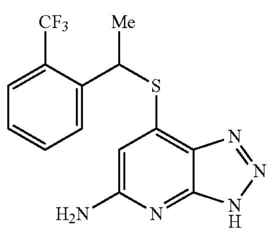 [SMILES: CC(Sc1cc(N)nc2[nH]nnc12)c1ccccc1C(F)(F)F] | 7-((1-(2-(trifluoromethyl)phenyl)ethyl)thio)-3H-[1,2,3]triazolo[4,5-b]pyridin-5-amine | MS(ESI) 340.1 (M + H)$^+$. |
| 31 | 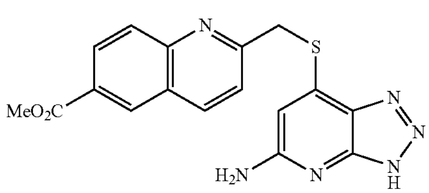 [SMILES: COC(=O)c1ccc2nc(CSc3cc(N)nc4[nH]nnc34)ccc2c1] | methyl 2-(((5-amino-3H-[1,2,3]triazolo[4,5-b]pyridin-7-yl)thio)methyl)quinoline-6-carboxylate | MS(ESI) 367.1 (M + H)$^+$. $^1$H NMR (500 MHz, DMSO-$d_6$) δ 8.70 (s, 1H), 8.60 (d, J = 8.5 Hz, 1H), 8.24 (dd, J = 8.8, 1.4 Hz, 1H), 8.14 (d, J = 8.8 Hz, 1H), 7.80 (d, J = 8.5 Hz, 1H), 6.71 (br. s., 1H), 4.82 (s, 2H), 3.94 (s, 3H). |
| 32 | 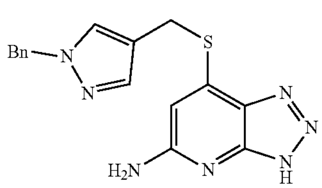 [SMILES: Nc1cc(SCc2cnn(Cc3ccccc3)c2)c2nn[nH]c2n1] | 7-(((1-benzyl-1H-pyrazol-4-yl)methyl)thio)-3H-[1,2,3]triazolo[4,5-b]pyridin-5-amine | MS(ESI) 338.2 (M + H)$^+$. $^1$H NMR (500 MHz, DMSO-$d_6$) δ 7.85 (s, 1H), 7.51 (s, 1H), 7.40-7.25 (m, 3H), 7.18 (d, J = 7.2 Hz, 2H), 6.57 (br. s., 2H), 6.47 (s, 1H), 5.28 (s, 2H), 4.31 (s, 2H) |

-continued

| Ex. No. | Structure | Name | Analytical Data |
|---|---|---|---|
| 33 | 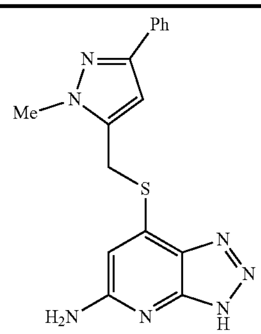 | 7-(((1-methyl-3-phenyl-1H-pyrazol-5-yl)methyl)thio)-3H-[1,2,3]triazolo[4,5-b]pyridin-5-amine | MS(ESI) 338.2 (M + H)$^+$. $^1$H NMR (500 MHz, DMSO-d$_6$) δ 7.73 (d, J = 7.2 Hz, 2H), 7.47-7.34 (m, 2H), 7.32-7.21 (m, 1H), 6.75 (s, 1H), 6.59 (br. s., 2H), 6.51 (s, 1H), 4.65 (s, 2H), 3.93 (s, 3H) |
| 34 | 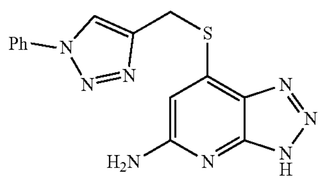 [SMILES: Nc1cc(SCc2cn(-c3ccccc3)nn2)c2nn[nH]c2n1] | 7-(((1-phenyl-1H-1,2,3-triazol-4-yl)methyl)thio)-3H-[1,2,3]triazolo[4,5-b]pyridin-5-amine | MS(ESI) 325.2 (M + H)$^+$. $^1$H NMR (500 MHz, DMSO-d$_6$) δ 8.82 (s, 1H), 7.89 (d, J = 7.7 Hz, 2H), 7.61 (t, J = 8.0 Hz, 2H), 7.50 (s, 1H), 6.64-6.48 (m, 1H), 4.62 (s, 2H) |
| 35 | 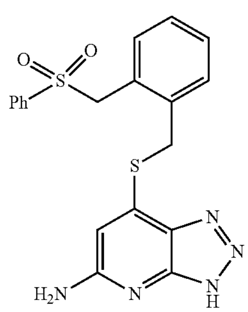 [SMILES: Nc1cc(SCc2ccccc2CS(=O)(=O)c2ccccc2)c2nn[nH]c2n1] | 7-((2-((phenylsulfonyl)methyl)benzyl)thio)-3H-[1,2,3]triazolo[4,5-b]pyridin-5-amine | MS(ESI) 412.0 (M + H)$^+$. $^1$H NMR (500 MHz, DMSO-d$_6$) δ 7.86-7.73 (m, 3H), 7.68-7.58 (m, 2H), 7.51 (d, J = 7.7 Hz, 1H), 7.35 (t, J = 7.4 Hz, 1H), 7.25 (t, J = 7.6 Hz, 1H), 7.13 (d, J = 7.4 Hz, 1H), 6.54-6.40 (m, 1H), 4.85 (s, 2H), 4.53 (s, 2H) |
| 36 | 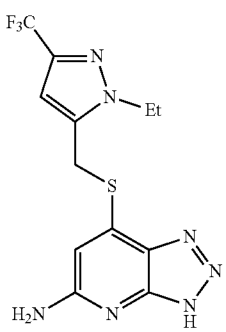 [SMILES: CCn1nc(C(F)(F)F)cc1CSc1cc(N)nc2[nH]nnc12] | 7-(((1-ethyl-3-(trifluoromethyl)-1H-pyrazol-5-yl)methyl)thio)-3H-[1,2,3]triazolo[4,5-b]pyridin-5-amine | MS(ESI) 344 (M + H)$^+$ $^1$H NMR (500 MHz, DMSO-d$_6$) δ 6.88 (s, 1H), 6.62-6.52 (m, 2H), 6.49 (s, 1H), 4.45 (s, 2H), 4.23 (q, J = 7.3 Hz, 2H), 1.38 (t, J = 7.3 Hz, 3H) |
| 37 | 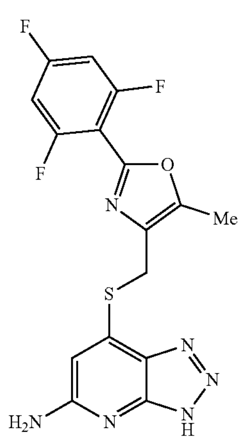 [SMILES: Cc1oc(-c2c(F)cc(F)cc2F)nc1CSc1cc(N)nc2[nH]nnc12] | 7-(((5-methyl-2-(2,4,6-trifluorophenyl)oxazol-4-yl)methyl)thio)-3H-[1,2,3]triazolo[4,5-b]pyridin-5-amine | MS(ESI) 393.1 (M + H)$^+$. $^1$H NMR (500 MHz, CD$_3$OD-d$_4$) δ 6.93 (t, J = 8.7 Hz, 2H), 6.73 (s, 1H), 4.44 (s, 2H), 2.43 (s, 3H) |

-continued

| Ex. No. | Structure | Name | Analytical Data |
|---|---|---|---|
| 38 | (structure) | 7-((2,2,2-trifluoro-1-phenylethyl)thio)-3H-[1,2,3]triazolo[4,5-b]pyridin-5-amine | MS(ESI) 326.1 (M + H)$^+$. $^1$H NMR (500 MHz, CD$_3$OD) δ 7.57-7.52 (m, 2H), 7.43-7.34 (m, 3H), 6.64-6.57 (m, 1H), 6.20-6.08 (m, 1H) |
| 39 | (structure) | 7-((2,5-bis(trifluoromethyl)benzyl)thio)-3H-[1,2,3]triazolo[4,5-b]pyridin-5-amine | MS(ESI) 394.0 (M + H)$^+$. $^1$H NMR (500 MHz, CD$_3$OD) δ 7.94 (s, 1H), 7.90 (d, J = 8.4 Hz, 1H), 7.74 (d, J = 7.9 Hz, 1H), 6.50 (s, 1H), 4.73 (s, 2H) |
| 40 | (structure) | 2-((5-amino-3H-[1,2,3]triazolo[4,5-b]pyridin-7-yl)thio)-1,2-diphenylethanone | MS(ESI) 362.1 (M + H)$^+$. $^1$H NMR (500 MHz, CD$_3$OD) δ 8.06 (d, J = 8.4 Hz, 1H), 7.64 (s, 1H), 7.55 (s, 1H), 7.49-7.40 (m, 4H), 7.35-7.17 (m, 3H), 6.48 (s, 1H) |
| 41 | (structure) | 7-((2-(1H-pyrazol-1-yl)benzyl)thio)-3H-[1,2,3]triazolo[4,5-b]pyridin-5-amine | MS(ESI) 324.1 (M + H)$^+$. |
| 42 | (structure) | 7-((4-bromo-2-fluoro-6-(methylsulfonyl)benzyl)thio)-3H-[1,2,3]triazolo[4,5-b]pyridin-5-amine | MS(ESI) 432/434 (M + H)$^+$. $^1$H NMR (500 MHz, DMSO-d$_6$) δ 8.16-8.05 (m, 1H), 8.01-7.95 (m, 1H), 6.63-6.48 (m, 1H), 4.97-4.82 (m, 2H), 3.45 (s, 3H) |

| Ex. No. | Structure | Name | Analytical Data |
|---|---|---|---|
| 43 | 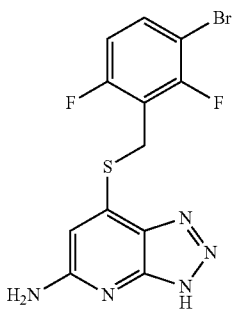 [SMILES: Nc1cc(SCc2c(F)ccc(Br)c2F)c2nn[nH]c2n1] | 7-((3-bromo-2,6-difluorobenzyl)thio)-3H-[1,2,3]triazolo[4,5-b]pyridin-5-amine | MS(ESI) 372/373.9 (M + H)+. 1H NMR (500 MHz, DMSO-$d_6$) δ 7.81-7.70 (m, 1H), 7.27-7.13 (m, 1H), 6.68-6.58 (m, 2H), 6.56-6.49 (m, 1H), 4.58 (s, 2H) |
| 44 | 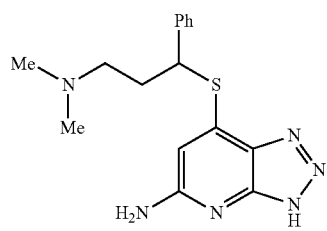 [SMILES: CN(C)CCC(Sc1cc(N)nc2[nH]nnc12)c1ccccc1] | 7-((3-(dimethylamino)-1-phenylpropyl)thio)-3H-[1,2,3]triazolo[4,5-b]pyridin-5-amine | MS(ESI) 329.2 (M + H)+. 1H NMR (500 MHz, DMSO-$d_6$) δ 7.48 (m, 3H), 7.37 (m, 2H), 6.88-6.76 (m, 2H), 6.73-6.62 (m, 2H), 6.46-6.33 (m, 1H), 5.20-5.00 (m, 1H), 3.08-3.01 (m, 1H), 3.01-2.89 (m, 1H), 2.77 (br. s., 6H), 2.41 (d, J = 8.3 Hz, 2H) |
| 45 | 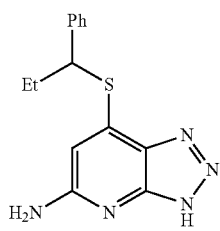 [SMILES: CCC(Sc1cc(N)nc2[nH]nnc12)c1ccccc1] | 7-((1-phenylpropyl)thio)-3H-[1,2,3]triazolo[4,5-b]pyridin-5-amine | MS(ESI) 286.1 (M + H)+. 1H NMR (500 MHz, DMSO-$d_6$) δ 7.45 (d, J = 7.4 Hz, 2H), 7.34 (t, J = 7.6 Hz, 2H), 7.28-7.11 (m, 1H), 6.52 (br. s., 2H), 6.42 (s, 1H), 4.90-4.76 (m, 1H), 2.16-1.87 (m, 2H), 0.90 (t, J = 7.3 Hz, 3H) |
| 46 | 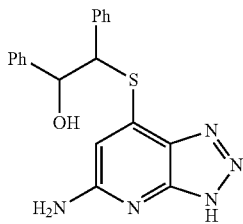 [SMILES: Nc1cc(SC(c2ccccc2)C(O)c2ccccc2)c2nn[nH]c2n1] | 2-((5-amino-3H-[1,2,3]triazolo[4,5-b]pyridin-7-yl)thio)-1,2-diphenylethanol | MS(ESI) 364.1 (M + H)+. 1H NMR (500 MHz, DMSO-$d_6$) δ 7.32 (m, 3H), 7.23-7.13 (m, 6H), 7.11-7.06 (m, 1H), 6.54-6.45 (m, 2H), 6.39-6.30 (m, 1H), 5.99-5.93 (m, 1H), 5.21 (br. s., 1H) |
| 47 | 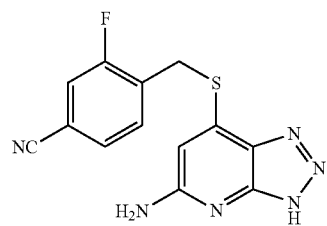 [SMILES: N#Cc1ccc(CSc2cc(N)nc3[nH]nnc23)c(F)c1] | 4-(((5-amino-3H-[1,2,3]triazolo[4,5-b]pyridin-7-yl)thio)methyl)-3-fluorobenzonitrile | MS(ESI) 301.1 (M + H)+. 1H NMR (500 MHz, DMSO-$d_6$) δ 7.92-7.85 (m, 1H), 7.67 (m, 2H), 6.61-6.53 (s, 2H), 6.48-6.35 (s, 1H), 4.62 (s, 2H). |

-continued

| Ex. No. | Structure | Name | Analytical Data |
|---|---|---|---|
| 48 | 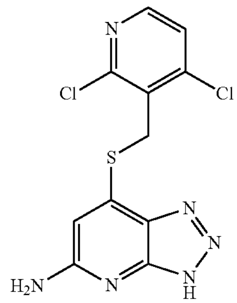 [SMILES: Nc1cc(SCc2c(Cl)ccnc2Cl)c2nn[nH]c2n1] | 7-(((2,4-dichloropyridin-3-yl)methyl)thio)-3H-[1,2,3]triazolo[4,5-b]pyridin-5-amine | MS(ESI) 327.0 (M + H)+. 1H NMR (500 MHz, DMSO-d6) δ 8.39 (d, J = 5.2 Hz, 1H), 7.71 (d, J = 5.2 Hz, 1H), 6.68 (br. s., 2H), 6.59 (br. s., 1H), 4.72 (s, 2H) |
| 49 | 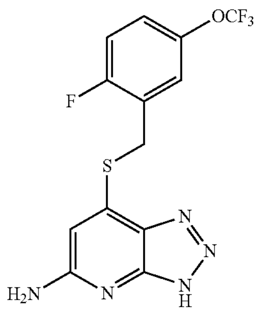 [SMILES: Nc1cc(SCc2cc(OC(F)(F)F)ccc2F)c2nn[nH]c2n1] | 7-((2-fluoro-5-(trifluoromethoxy)benzyl)thio)-3H-[1,2,3]triazolo[4,5-b]pyridin-5-amine | MS(ESI) 360.1 (M + H)+. 1H NMR (500 MHz, DMSO-d6) δ 7.52 (d, J = 4.4 Hz, 1H), 7.42-7.35 (m, 2H), 6.60 (br. s., 2H), 6.49 (s, 1H), 4.57 (s, 2H) |
| 50 | 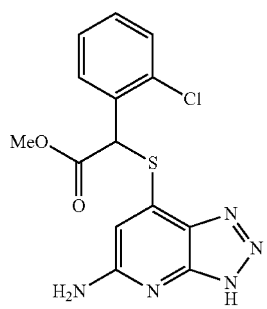 [SMILES: COC(=O)C(Sc1cc(N)nc2[nH]nnc12)c1ccccc1Cl] | methyl 2-((5-amino-3H-[1,2,3]triazolo[4,5-b]pyridin-7-yl)thio)-2-(2-chlorophenyl)acetate | MS(ESI) 350.1 (M + H)+. 1H NMR (500 MHz, DMSO-d6) δ 7.60-7.51 (m, 2H), 7.44-7.36 (m, 2H), 6.69 (br. s., 2H), 6.44 (br. s., 1H), 3.71 (s, 3H) |
| 51 | 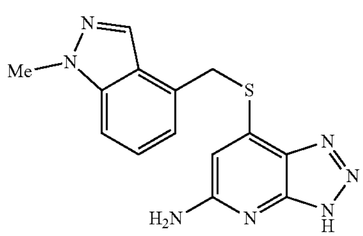 [SMILES: Cn1ncc2c(CSc3cc(N)nc4[nH]nnc34)cccc21] | 7-(((1-methyl-1H-indazol-4-yl)methyl)thio)-3H-[1,2,3]triazolo[4,5-b]pyridin-5-amine | MS(ESI) 312.1 (M + H)+. 1H NMR (500 MHz, DMSO-d6) δ 8.26 (s, 1H), 7.58 (d, J = 8.5 Hz, 1H), 7.35 (t, J = 7.7 Hz, 1H), 7.22 (d, J = 6.9 Hz, 1H), 6.67-6.45 (m, 1H), 4.83 (s, 2H), 4.06 (s, 3H) |
| 52 | 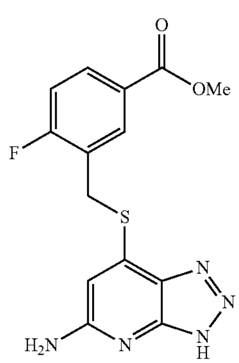 [SMILES: COC(=O)c1ccc(F)c(CSc2cc(N)nc3[nH]nnc23)c1] | methyl 3-(((5-amino-3H-[1,2,3]triazolo[4,5-b]pyridin-7-yl)thio)methyl)-4-fluorobenzoate | MS(ESI) 334.7 (M + H)+. 1H NMR (500 MHz, DMSO-d6) δ 8.18-8.09 (m, 1H), 8.01-7.89 (m, 1H), 7.41 (s, 1H), 6.54-6.44 (m, 1H), 4.62 (s, 2H), 3.84 (s, 3H) |

-continued

| Ex. No. | Structure | Name | Analytical Data |
|---|---|---|---|
| 53 | 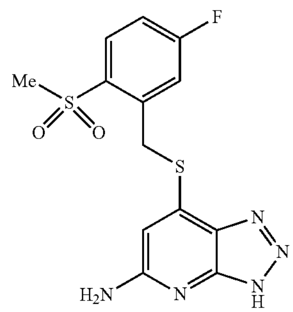 [SMILES: CS(=O)(=O)c1ccc(F)cc1CSc1cc(N)nc2[nH]nnc12] | 7-((5-fluoro-2-(methylsulfonyl)benzyl)thio)-3H-[1,2,3]triazolo[4,5-b]pyridin-5-amine | MS(ESI) 354 (M + H)+. 1H NMR (500 MHz, DMSO-d6) δ 8.16-8.06 (m, 1H), 7.66-7.55 (m, 1H), 7.48 (br. s., 1H), 6.54-6.43 (m, 1H), 4.96 (s, 2H), 3.37-3.28 (m, 3H) |
| 54 | 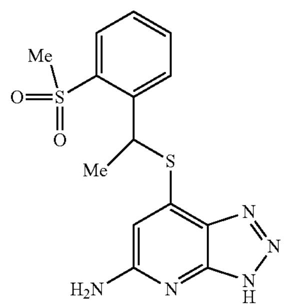 [SMILES: CC(Sc1cc(N)nc2[nH]nnc12)c1ccccc1S(C)(=O)=O] | 7-((1-(2-(methylsulfonyl)phenyl)ethyl)thio)-3H-[1,2,3]triazolo[4,5-b]pyridin-5-amine | MS(ESI) 350.1 (M + H)+. |
| 55 | 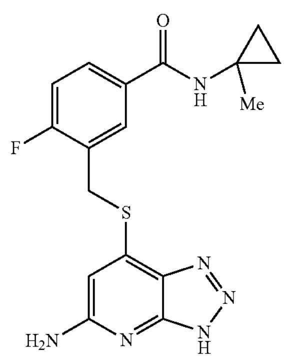 [SMILES: CC1(NC(=O)c2ccc(F)c(CSc3cc(N)nc4[nH]nnc34)c2)CC1] | 3-(((5-amino-3H-[1,2,3]triazolo[4,5-b]pyridin-7-yl)thio)methyl)-4-fluoro-N-(1-methylcyclopropyl)benzamide | MS(ESI) 373.2 (M + H)+. 1H NMR (500 MHz, DMSO-d6) δ 8.66 (s, 1H), 8.10-7.99 (m, 1H), 7.89-7.77 (m, 1H), 7.31 (s, 1H), 6.56-6.38 (m, 1H), 4.55 (s, 2H), 1.36 (s, 3H), 0.73 (s, 2H), 0.61 (s, 2H) |
| 56 | 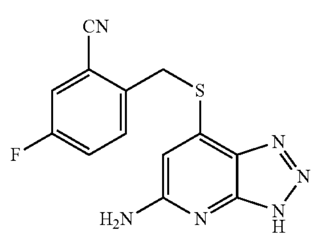 [SMILES: N#Cc1cc(F)ccc1CSc1cc(N)nc2[nH]nnc12] | 2-(((5-amino-3H-[1,2,3]triazolo[4,5-b]pyridin-7-yl)thio)methyl)-5-fluorobenzonitrile | MS(ESI) 301.1 (M + H)+. 1H NMR (500 MHz, DMSO-d6) δ 7.93 (m, 1H), 7.71 (m, 1H), 7.58 (s, 1H), 6.65 (br. s., 2H), 6.48 (br. s., 1H), 4.68 (s, 2H) |
| 57 | 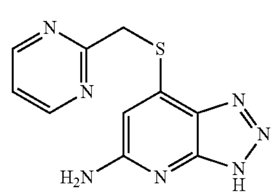 [SMILES: Nc1cc(SCc2ncccn2)c2nn[nH]c2n1] | 7-((pyrimidin-2-ylmethyl)thio)-3H-[1,2,3]triazolo[4,5-b]pyridin-5-amine | MS(ESI) 260.1 (M + H)+. 1H NMR (500 MHz, DMSO-d6) δ 8.91-8.69 (m, 2H), 7.50-7.40 (m, 1H), 6.68-6.57 (m, 2H), 6.54-6.44 (m, 1H), 4.74-4.58 (m, 2H) |

-continued

| Ex. No. | Structure | Name | Analytical Data |
|---|---|---|---|
| 58 | 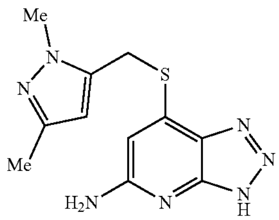 [SMILES: Cc1cc(CSc2cc(N)nc3[nH]nnc23)n(C)n1] | 7-(((1,3-dimethyl-1H-pyrazol-5-yl)methyl)thio)-3H-[1,2,3]triazolo[4,5-b]pyridin-5-amine | MS(ESI) 276.2 (M + H)+. $^1$H NMR (500 MHz, DMSO-$d_6$) δ 6.40 (s, 1H), 6.03 (s, 1H), 4.56 (s, 2H), 3.77 (s, 3H), 2.06 (s, 3H) |
| 59 | 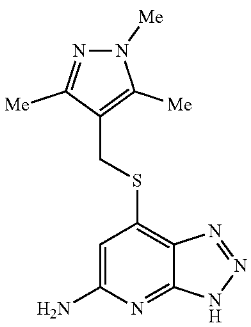 | 7-(((1,3,5-trimethyl-1H-pyrazol-4-yl)methyl)thio)-3H-[1,2,3]triazolo[4,5-b]pyridin-5-amine | MS(ESI) 289.1 (M + H)+. $^1$H NMR (500 MHz, DMSO-$d_6$) δ 6.60 (br. s., 2H), 6.49 (s, 1H), 4.24 (s, 2H), 3.65 (s, 3H), 2.22 (s, 3H), 2.13 (s, 3H) |
| 60 | 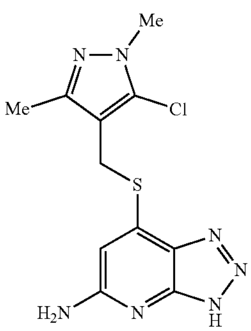 [SMILES: Cc1nn(C)c(Cl)c1CSc1cc(N)nc2[nH]nnc12] | 7-(((5-chloro-1,3-dimethyl-1H-pyrazol-4-yl)methyl)thio)-3H-[1,2,3]triazolo[4,5-b]pyridin-5-amine | MS(ESI) 310.2 (M + H)+. $^1$H NMR (500 MHz, DMSO-$d_6$) δ 6.56 (br. s., 1H), 4.29 (s, 2H), 3.74 (s, 3H), 2.19 (s, 3H) |
| 61 | 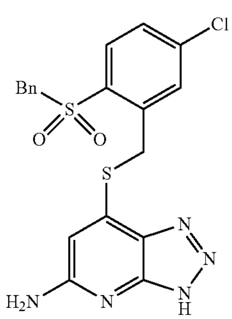 [SMILES: Nc1cc(SCc2cc(Cl)ccc2S(=O)(=O)Cc2ccccc2)c2nn[nH]c2n1] | 7-((2-(benzylsulfonyl)-5-chlorobenzyl)thio)-3H-[1,2,3]triazolo[4,5-b]pyridin-5-amine | MS(ESI) 446.1 (M + H)+. $^1$H NMR (500 MHz, DMSO-$d_6$) δ 7.97 (s, 1H), 7.74 (s, 1H), 7.70-7.65 (m, 1H), 7.62-7.57 (m, 1H), 7.41-7.27 (m, 4H), 7.18 (d, J = 7.4 Hz, 2H), 6.53 (br. s., 1H), 4.83 (s, 2H), 4.77 (s, 2H) |
| 62 | 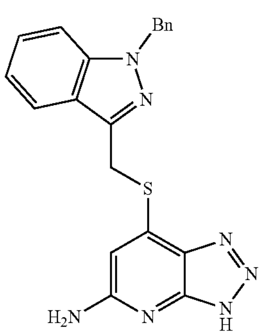 [SMILES: Nc1cc(SCc2nn(Cc3ccccc3)c3ccccc23)c2nn[nH]c2n1] | 7-(((1-benzyl-1H-indazol-3-yl)methyl)thio)-3H-[1,2,3]triazolo[4,5-b]pyridin-5-amine | MS(ESI) 388.2 (M + H)+. $^1$H NMR (500 MHz, DMSO-$d_6$) δ 7.90 (d, J = 8.0 Hz, 1H), 7.68 (d, J = 8.3 Hz, 1H), 7.39 (s, 1H), 7.33-7.22 (m, 5H), 7.16 (s, 1H), 6.66 (br. s., 3H), 5.63 (s, 2H), 4.85 (s, 2H) |

-continued

| Ex. No. | Structure | Name | Analytical Data |
|---|---|---|---|
| 63 | 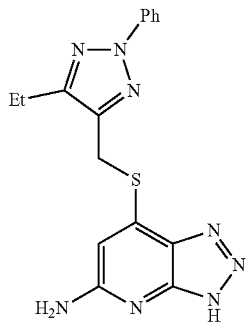 [SMILES: CCc1nn(-c2ccccc2)nc1CSc1cc(N)nc2[nH]nnc12] | 7-(((5-ethyl-2-phenyl-2H-1,2,3-triazol-4-yl)methyl)thio)-3H-[1,2,3]triazolo[4,5-b]pyridin-5-amine | MS(ESI) 353.2 (M + H)+. 1H NMR (500 MHz, DMSO-d6) δ 7.97 (d, J = 8.0 Hz, 2H), 7.54 (t, J = 7.6 Hz, 2H), 7.45-7.33 (m, 1H), 6.81-6.49 (m, 3H), 4.65 (s, 2H), 2.81 (q, J = 7.5 Hz, 2H), 1.28 (t, J = 7.5 Hz, 3H) |
| 64 | 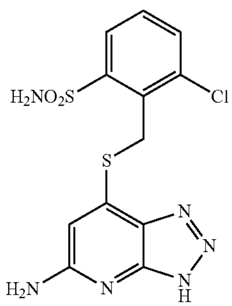 [SMILES: Nc1cc(SCc2c(Cl)cccc2S(N)(=O)=O)c2nn[nH]c2n1] | 2-(((5-amino-3H-[1,2,3]triazolo[4,5-b]pyridin-7-yl)thio)methyl)-3-chlorobenzenesulfonamide | MS(ESI) 371.1 (M + H)+. |
| 65 | 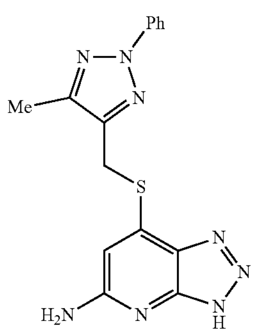 [SMILES: Cc1nn(-c2ccccc2)nc1CSc1cc(N)nc2[nH]nnc12] | 7-(((5-methyl-2-phenyl-2H-1,2,3-triazol-4-yl)methyl)thio)-3H-[1,2,3]triazolo[4,5-b]pyridin-5-amine | MS(ESI) 338.9 (M + H)+. 1H NMR (500 MHz, DMSO-d6) δ 7.97 (d, J = 7.7 Hz, 2H), 7.54 (t, J = 7.6 Hz, 2H), 7.44-7.26 (m, 1H), 6.67 (br. s., 1H), 4.65 (s, 2H), 2.43-2.35 (m, 3H) |
| 66 | 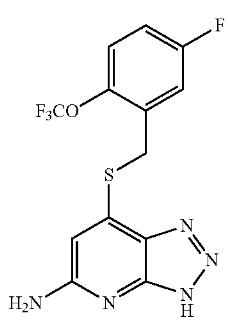 [SMILES: Nc1cc(SCc2cc(F)ccc2OC(F)(F)F)c2nn[nH]c2n1] | 7-((5-fluoro-2-(trifluoromethoxy)benzyl)thio)-3H-[1,2,3]triazolo[4,5-b]pyridin-5-amine | MS(ESI) 359.9 (M + H)+. |

-continued

| Ex. No. | Structure | Name | Analytical Data |
|---|---|---|---|
| 67 | 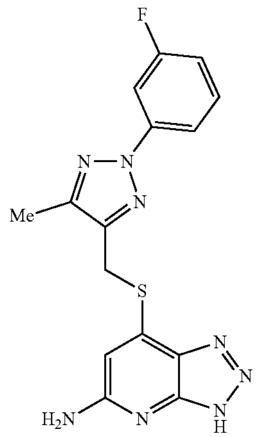 [SMILES: Cc1nn(-c2cccc(F)c2)nc1CSc1cc(N)nc2[nH]nnc12] | 7-(((2-(3-fluorophenyl)-5-methyl-2H-1,2,3-triazol-4-yl)methyl)thio)-3H-[1,2,3]triazolo[4,5-b]pyridin-5-amine | MS(ESI) 357.1 (M + H)$^+$. $^1$H NMR (500 MHz, DMSO-d$_6$) δ 7.85-7.71 (m, 2H), 7.59 (q, J = 7.5 Hz, 1H), 7.30-7.18 (m, 1H), 6.63 (br. s., 1H), 4.64 (s, 2H), 2.41 (s, 3H) |
| 68 | 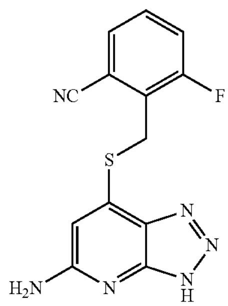 [SMILES: N#Cc1cccc(F)c1CSc1cc(N)nc2[nH]nnc12] | 2-(((5-amino-3H-[1,2,3]triazolo[4,5-b]pyridin-7-yl)thio)methyl)-3-fluorobenzonitrile | MS(ESI) 301.1 (M + H)$^+$. $^1$H NMR (500 MHz, DMSO-d$_6$) δ 7.80 (d, J = 7.4 Hz, 1H), 7.72-7.57 (m, 2H), 6.70 (br. s., 2H), 6.54 (br. s., 1H), 4.67 (br. s., 2H) |
| 69 | 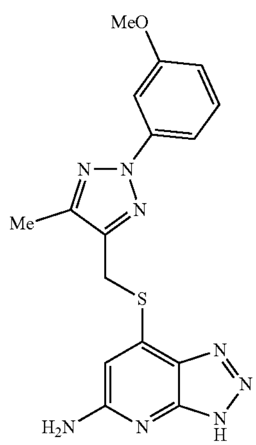 [SMILES: COc1cccc(-n2nc(C)c(CSc3cc(N)nc4[nH]nnc34)n2)c1] | 7-(((2-(3-methoxyphenyl)-5-methyl-2H-1,2,3-triazol-4-yl)methyl)thio)-3H-[1,2,3]triazolo[4,5-b]pyridin-5-amine | MS(ESI) 369.1 (M + H)$^+$. $^1$H NMR (500 MHz, DMSO-d$_6$) δ 7.52 (br. s., 1H), 7.46 (br. s., 2H), 6.99-6.91 (m, 1H), 6.60 (br. s., 3H), 4.64 (s, 2H), 3.84 (s, 3H), 2.39 (s, 3H) |
| 70 | 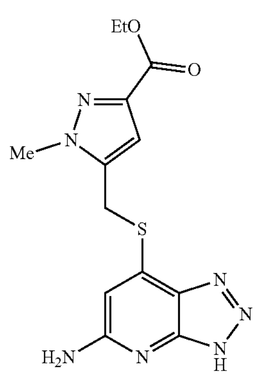 [SMILES: CCOC(=O)c1cc(CSc2cc(N)nc3[nH]nnc23)n(C)n1] | ethyl 5-(((5-amino-3H-[1,2,3]triazolo[4,5-b]pyridin-7-yl)thio)methyl)-1-methyl-1H-pyrazole-3-carboxylate | MS(ESI) 334.1 (M + H)$^+$. $^1$H NMR (500 MHz, DMSO-d$_6$) δ 6.75 (br. s., 1H), 6.47 (br. s., 1H), 4.65 (s, 2H), 4.23 (q, J = 6.7 Hz, 2H), 4.01-3.89 (m, 3H), 1.26 (t, J = 6.9 Hz, 3H) |

| Ex. No. | Structure | Name | Analytical Data |
|---|---|---|---|
| 71 | 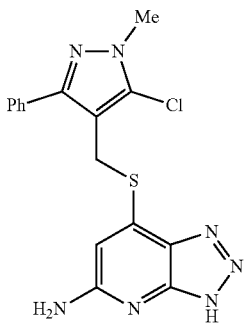 [SMILES: Cn1nc(-c2ccccc2)c(CSc2cc(N)nc3[nH]nnc23)c1Cl] | 7-(((5-chloro-1-methyl-3-phenyl-1H-pyrazol-4-yl)methyl)thio)-3H-[1,2,3]triazolo[4,5-b]pyridin-5-amine | MS(ESI) 372.1 (M + H)+. $^1$H NMR (500 MHz, DMSO-$d_6$) δ 7.72 (d, J = 7.2 Hz, 2H), 7.55-7.36 (m, 3H), 6.55-6.45 (m, 1H), 4.43 (br. s., 2H), 3.97-3.87 (m, 3H) |
| 72 | 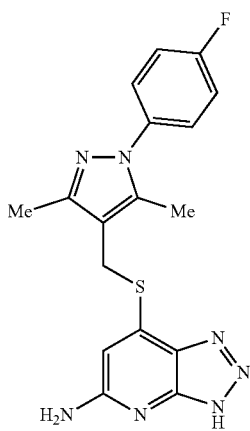 [SMILES: Cc1nn(-c2ccc(F)cc2)c(C)c1CSc1cc(N)nc2[nH]nnc12] | 7-(((1-(4-fluorophenyl)-3,5-dimethyl-1H-pyrazol-4-yl)methyl)thio)-3H-[1,2,3]triazolo[4,5-b]pyridin-5-amine | MS(ESI) 370.1 (M + H)+. $^1$H NMR (500 MHz, DMSO-$d_6$) δ 7.62-7.50 (m, 2H), 7.42-7.24 (m, 2H), 6.44-6.35 (m, 1H), 6.22-6.01 (m, 2H), 4.40-4.29 (m, 2H), 2.34-2.20 (m, 6H) |
| 73 | 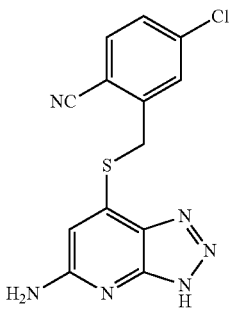 [SMILES: N#Cc1ccc(Cl)cc1CSc1cc(N)nc2[nH]nnc12] | 2-(((5-amino-3H-[1,2,3]triazolo[4,5-b]pyridin-7-yl)thio)methyl)-4-chlorobenzonitrile | MS(ESI) 317.0 (M + H)+. $^1$H NMR (500 MHz, DMSO-$d_6$) δ 8.04-7.90 (m, 1H), 7.83-7.75 (m, 1H), 7.68-7.56 (m, 1H), 6.69 (br. s., 2H), 6.53-6.42 (m, 1H), 4.69 (br. s., 2H) |
| 74 | 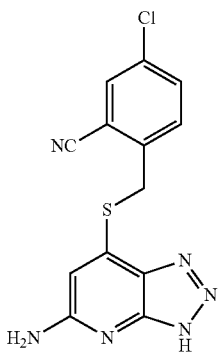 [SMILES: N#Cc1cc(Cl)ccc1CSc1cc(N)nc2[nH]nnc12] | 2-(((5-amino-3H-[1,2,3]triazolo[4,5-b]pyridin-7-yl)thio)methyl)-5-chlorobenzonitrile | MS(ESI) 317.0 (M + H)+. $^1$H NMR (500 MHz, DMSO-$d_6$) δ 8.11 (br. s., 1H), 7.76 (d, J = 8.3 Hz, 1H), 7.67 (d, J = 8.3 Hz, 1H), 6.66 (br. s., 2H), 6.45 (br. s., 1H), 4.69 (br. s., 2H) |

-continued

| Ex. No. | Structure | Name | Analytical Data |
|---|---|---|---|
| 75 | 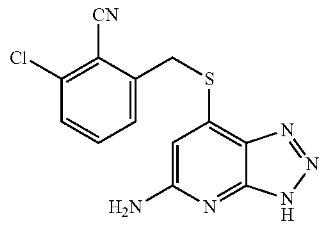 [SMILES: N#Cc1c(Cl)cccc1CSc1cc(N)nc2[nH]nnc12] | 2-(((5-amino-3H-[1,2,3]triazolo[4,5-b]pyridin-7-yl)thio)methyl)-6-chlorobenzonitrile | MS(ESI) 317.0 (M + H)+. 1H NMR (500 MHz, DMSO-$d_6$) δ 7.70 (m, 2H), 7.63 (m, 1H), 6.67 (br. s., 2H), 6.44 (br. s., 1H), 4.73 (br. s., 2H) |
| 76 | 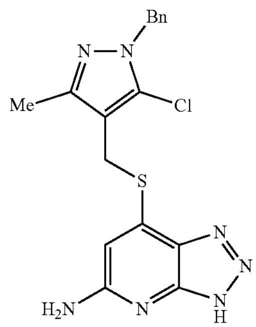 [SMILES: Cc1nn(Cc2ccccc2)c(Cl)c1CSc1cc(N)nc2[nH]nnc12] | 7-(((1-benzyl-5-chloro-3-methyl-1H-pyrazol-4-yl)methyl)thio)-3H-[1,2,3]triazolo[4,5-b]pyridin-5-amine | MS(ESI) 386.1 (M + H)+. 1H NMR(500 MHz, DMSO-$d_6$) δ 7.36 (d, J = 7.7 Hz, 3H), 7.16 (s, 2H), 6.65-6.56 (m, 2H), 6.53-6.42 (m, 1H), 5.30 (s, 2H), 4.30 (s, 2H), 2.22 (s, 3H) |
| 77 | 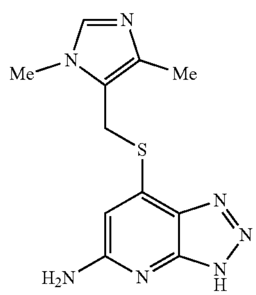 [SMILES: Cc1ncn(C)c1CSc1cc(N)nc2[nH]nnc12] | 7-(((1,4-dimethyl-1H-imidazol-5-yl)methyl)thio)-3H-[1,2,3]triazolo[4,5-b]pyridin-5-amine | MS(ESI) 276.1 (M + H)+. 1H NMR (500 MHz, DMSO-$d_6$) δ 7.58-7.39 (m, 1H), 6.34 (s, 1H), 6.01 (s, 2H), 4.58 (s, 2H), 3.63 (s, 3H), 2.03 (s, 3H) |
| 78 | 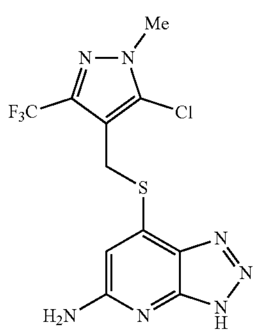 [SMILES: Cn1nc(C(F)(F)F)c(CSc2cc(N)nc3[nH]nnc23)c1Cl] | 7-(((5-chloro-1-methyl-3-(trifluoromethyl)-1H-pyrazol-4-yl)methyl)thio)-3H-[1,2,3]triazolo[4,5-b]pyridin-5-amine | MS(ESI) 364.0 (M + H)+. 1H NMR (500 MHz, DMSO-$d_6$) δ 6.62 (br. s., 2H), 6.53 (br. s., 1H), 4.42 (s, 2H), 3.92 (s, 3H) |
| 79 | 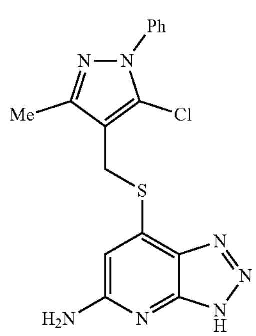 [SMILES: Cc1nn(-c2ccccc2)c(Cl)c1CSc1cc(N)nc2[nH]nnc12] | 7-(((5-chloro-3-methyl-1-phenyl-1H-pyrazol-4-yl)methyl)thio)-3H-[1,2,3]triazolo[4,5-b]pyridin-5-amine | MS(ESI) 372.1 (M + H)+. 1H NMR (500 MHz, DMSO-$d_6$) δ 7.61-7.53 (m, 4H), 7.51-7.43 (m, 1H), 6.61 (br. s., 2H), 6.56 (s, 1H), 4.39 (s, 2H), 2.31 (s, 3H) |

| Ex. No. | Structure | Name | Analytical Data |
|---|---|---|---|
| 80 | 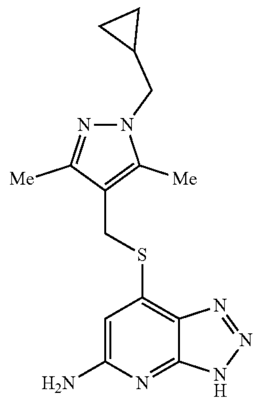 [SMILES: Cc1nn(CC2CC2)c(C)c1CSc1cc(N)nc2[nH]nnc12] | 7-(((1-(cyclopropylmethyl)-3,5-dimethyl-1H-pyrazol-4-yl)methyl)thio)-3H-[1,2,3]triazolo[4,5-b]pyridin-5-amine | MS(ESI) 316.1 (M + H)$^+$. $^1$H NMR (500 MHz, DMSO-d$_6$) δ 6.57 (br. s., 1H), 4.26 (s, 2H), 2.32 (s, 3H), 2.16-2.04 (m, 3H), 1.06-0.83 (m, 5H) |
| 81 | 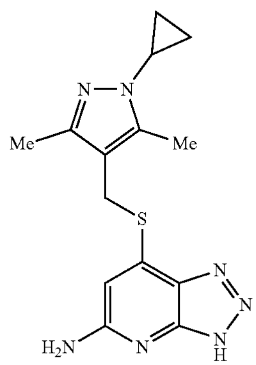 [SMILES: Cc1nn(C2CC2)c(C)c1CSc1cc(N)nc2[nH]nnc12] | 7-(((1-cyclopropyl-3,5-dimethyl-1H-pyrazol-4-yl)methyl)thio)-3H-[1,2,3]triazolo[4,5-b]pyridin-5-amine | MS(ESI) 330.2 (M + H)$^+$. $^1$H NMR (500 MHz, DMSO-d$_6$) δ 6.62-6.47 (m, 1H), 4.86-4.65 (m, 1H), 4.25 (s, 2H), 2.52 (br. s., 2H), 2.36-2.26 (m, 2H), 2.19 (d, J = 13.5 Hz, 6H), 1.81-1.67 (m, 2H) |
| 82 | 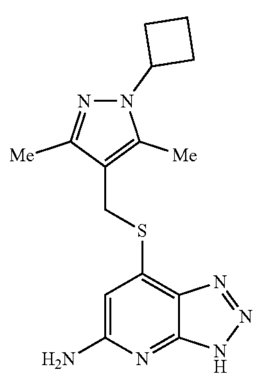 [SMILES: Cc1nn(C2CCC2)c(C)c1CSc1cc(N)nc2[nH]nnc12] | 7-(((1-cyclobutyl-3,5-dimethyl-1H-pyrazol-4-yl)methyl)thio)-3H-[1,2,3]triazolo[4,5-b]pyridin-5-amine | MS(ESI) 317.0 (M + H)$^+$. |
| 83 | 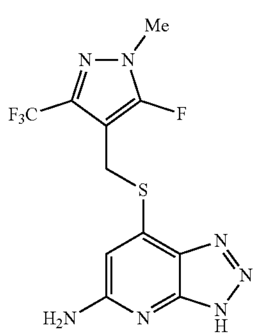 [SMILES: Cn1nc(C(F)(F)F)c(CSc2cc(N)nc3[nH]nnc23)c1F] | 7-(((5-fluoro-1-methyl-3-(trifluoromethyl)-1H-pyrazol-4-yl)methyl)thio)-3H-[1,2,3]triazolo[4,5-b]pyridin-5-amine | MS(ESI) 330.1 (M + H)$^+$. $^1$H NMR (500 MHz, DMSO-d$_6$) δ 8.00 (s, 1H), 6.51 (br. s., 1H), 4.42 (s, 2H), 3.90 (s, 3H) |

| Ex. No. | Structure | Name | Analytical Data |
|---|---|---|---|
| 84 | 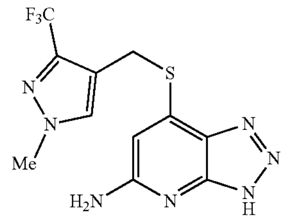 [SMILES: Cn1cc(CSc2cc(N)nc3[nH]nnc23)c(C(F)(F)F)n1] | 7-(((1-methyl-3-(trifluoromethyl)-1H-pyrazol-4-yl)methyl)thio)-3H-[1,2,3]triazolo[4,5-b]pyridin-5-amine | MS(ESI) 324.1 (M + H)+. |
| 85 | 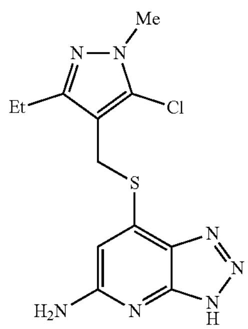 [SMILES: CCc1nn(C)c(Cl)c1CSc1cc(N)nc2[nH]nnc12] | 7-(((5-chloro-3-ethyl-1-methyl-1H-pyrazol-4-yl)methyl)thio)-3H-[1,2,3]triazolo[4,5-b]pyridin-5-amine | MS(ESI) 330.1 (M + H)+. |
| 86 | 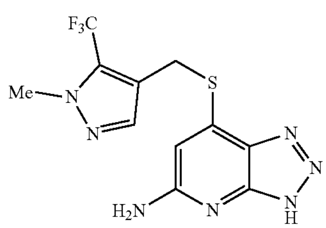 [SMILES: Cn1ncc(CSc2cc(N)nc3[nH]nnc23)c1C(F)(F)F] | 7-(((1-methyl-5-(trifluoromethyl)-1H-pyrazol-4-yl)methyl)thio)-3H-[1,2,3]triazolo[4,5-b]pyridin-5-amine | MS(ESI) 323.1 (M + H)+. 1H NMR (500 MHz, DMSO-$d_6$) δ 7.98 (s, 1H), 6.50 (br. s., 1H), 4.40 (s, 2H), 3.88 (s, 1H). |
| 87 | 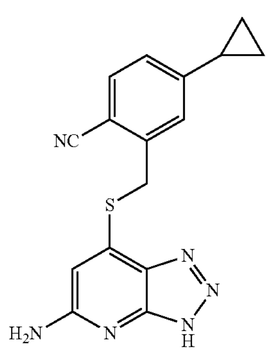 [SMILES: N#Cc1ccc(C2CC2)cc1CSc1cc(N)nc2[nH]nnc12] | 2-(((5-amino-3H-[1,2,3]triazolo[4,5-b]pyridin-7-yl)thio)methyl)-4-cyclopropylbenzonitrile | MS(ESI) 323.1 (M + H)+. |
| 88 | 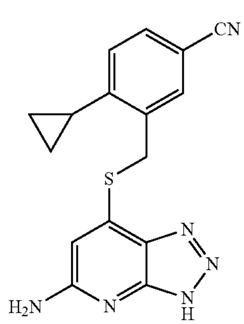 [SMILES: N#Cc1ccc(C2CC2)c(CSc2cc(N)nc3[nH]nnc23)c1] | 3-(((5-amino-3H-[1,2,3]triazolo[4,5-b]pyridin-7-yl)thio)methyl)-4-cyclopropylbenzonitrile | MS(ESI) 323.1 (M + H)+. |

| Ex. No. | Structure | Name | Analytical Data |
|---|---|---|---|
| 89 | 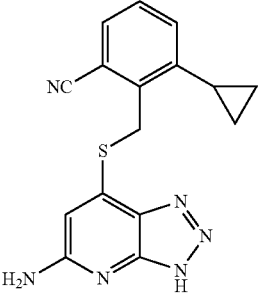 [SMILES: N#Cc1cccc(C2CC2)c1CSc1cc(N)nc2[nH]nnc12] | 2-(((5-amino-3H-[1,2,3]triazolo[4,5-b]pyridin-7-yl)thio)methyl)-3-cyclopropylbenzonitrile | MS(ESI) 323.1 (M + H)+. |
| 90 | 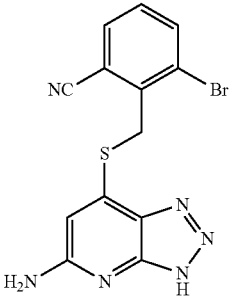 [SMILES: N#Cc1cccc(Br)c1CSc1cc(N)nc2[nH]nnc12] | 2-(((5-amino-3H-[1,2,3]triazolo[4,5-b]pyridin-7-yl)thio)methyl)-3-bromobenzonitrile | MS(ESI) 360.0 (M + H)+. $^1$H NMR (500 MHz, DMSO-$d_6$) δ 8.24-7.90 (m, 2H), 7.65-7.43 (m, 1H), 6.85-6.44 (m, 3H), 4.75 (br. s., 2H) |
| 91 | 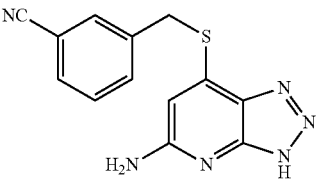 [SMILES: N#Cc1cccc(CSc2cc(N)nc3[nH]nnc23)c1] | 3-(((5-amino-3H-[1,2,3]triazolo[4,5-b]pyridin-7-yl)thio)methyl)benzonitrile | MS(ESI) 283.1 (M + H)+. $^1$H NMR (500 MHz, DMSO-$d_6$) δ 7.96 (s, 1H), 7.84 (d, J = 7.7 Hz, 1H), 7.78 (d, J = 7.7 Hz, 1H), 7.64-7.53 (m, 1H), 6.49 (br. s., 1H), 4.55 (s, 2H) |
| 92 | 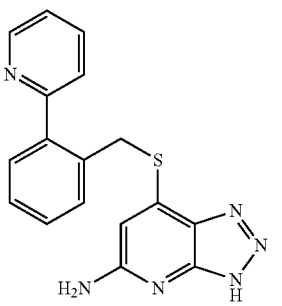 [SMILES: Nc1cc(SCc2ccccc2-c2ccccn2)c2nn[nH]c2n1] | 7-((2-(pyridin-2-yl)benzyl)thio)-3H-[1,2,3]triazolo[4,5-b]pyridin-5-amine | MS(ESI) 335.1 (M + H)+. $^1$H NMR (500 MHz, DMSO-$d_6$) δ 8.67 (d, J = 4.7 Hz, 1H), 8.00-7.88 (m, 1H), 7.73-7.62 (m, 2H), 7.55-7.33 (m, 4H), 6.49-6.33 (m, 1H), 4.71 (s, 2H) |
| 93 | 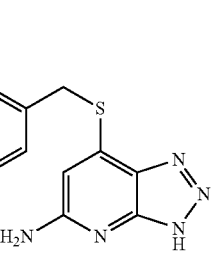 | 7-((3-((dimethylamino)methyl)benzyl)thio)-3H-[1,2,3]triazolo[4,5-b]pyridin-5-amine | MS(ESI) 315.1 (M + H)+. $^1$H NMR (500 MHz, DMSO-$d_6$) δ 7.57 (m, 2H), 7.47-7.34 (m, 2H), 6.50 (s, 1H), 4.49 (s, 2H), 4.24 (s, 2H), 2.73-2.61 (m, 6H) |

| Ex. No. | Structure | Name | Analytical Data |
|---|---|---|---|
| 94 | 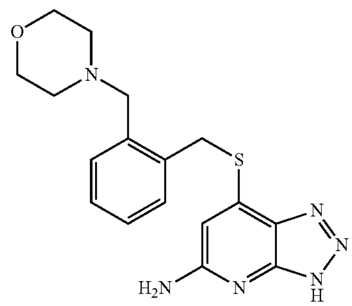 [SMILES: Nc1cc(SCc2ccccc2CN2CCOCC2)c2nn[nH]c2n1] | 7-((2-(morpholinomethyl)benzyl)thio)-3H-[1,2,3]triazolo[4,5-b]pyridin-5-amine | MS(ESI) 357.2 (M + H)$^+$. $^1$H NMR (500 MHz, DMSO-$d_6$) δ 7.69-7.48 (m, 2H), 7.44-7.31 (m, 2H), 6.50 (s, 1H), 4.67 (s, 2H), 4.51 (s, 2H), 3.65 (br. s., 2H), 3.27 (br. s., 3H), 2.50 (br. s., 3H) |
| 95 | 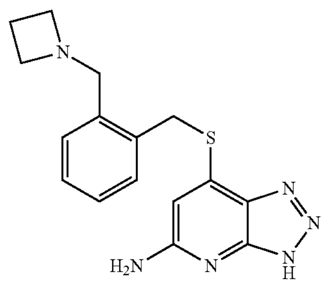 [SMILES: Nc1cc(SCc2ccccc2CN2CCC2)c2nn[nH]c2n1] | 7-((2-(azetidin-1-ylmethyl)benzyl)thio)-3H-[1,2,3]triazolo[4,5-b]pyridin-5-amine | MS(ESI) 327.1 (M + H)$^+$. |
| 96 | 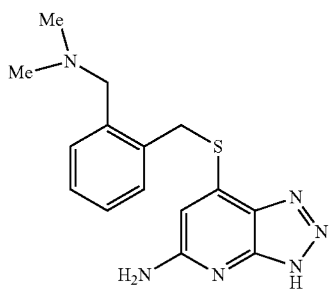 [SMILES: CN(C)Cc1ccccc1CSc1cc(N)nc2[nH]nnc12] | 7-((2-((dimethylamino)methyl)benzyl)thio)-3H-[1,2,3]triazolo[4,5-b]pyridin-5-amine | MS(ESI) 315.1 (M + H)$^+$. |
| 97 | 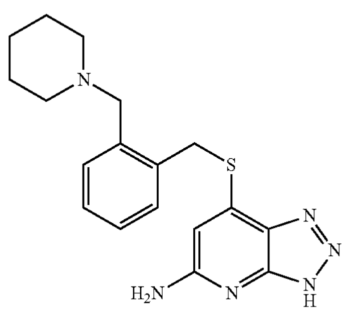 [SMILES: Nc1cc(SCc2ccccc2CN2CCCCC2)c2nn[nH]c2n1] | 7-((2-(piperidin-1-ylmethyl)benzyl)thio)-3H-[1,2,3]triazolo[4,5-b]pyridin-5-amine | MS(ESI) 355.2 (M + H)$^+$. $^1$H NMR (500 MHz, DMSO-$d_6$) δ 7.68-7.49 (m, 2H), 7.43-7.32 (m, 2H), 6.50 (s, 1H), 4.67 (s, 2H), 4.48 (br. s., 2H), 3.59-3.45 (m, 2H), 3.35 (m, 2H), 3.08 (m, 2H), 1.80 (m, 2H), 1.72-1.52 (m, 2H) |
| 98 | 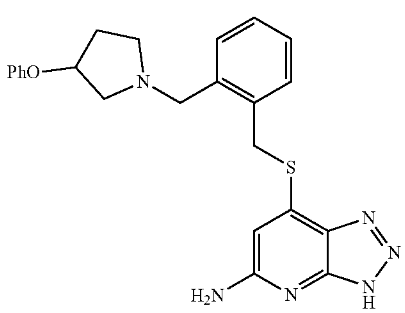 [SMILES: Nc1cc(SCc2ccccc2CN2CCC(Oc3ccccc3)C2)c2nn[nH]c2n1] | 7-((2-((3-phenoxypyrrolidin-1-yl)methyl)benzyl)thio)-3H-[1,2,3]triazolo[4,5-b]pyridin-5-amine | MS(ESI) 433.2 (M + H)$^+$. |

| Ex. No. | Structure | Name | Analytical Data |
|---|---|---|---|
| 99 | 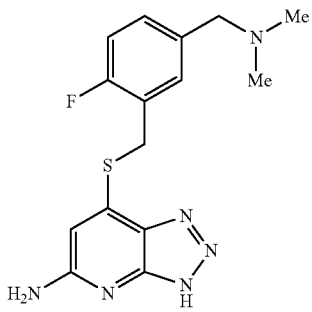 [SMILES: CN(C)Cc1ccc(F)c(CSc2cc(N)nc3[nH]nnc23)c1] | 7-((5-((dimethylamino) methyl)-2-fluorobenzyl) thio)-3H-[1,2,3]triazolo[4,5-b]pyridin-5-amine | MS(ESI) 333.1 (M + H)+. 1H NMR (500 MHz, DMSO-$d_6$) δ 7.43 (d, J = 7.0 Hz, 1H), 7.34-7.09 (m, 2H), 6.57 (br. s., 2H), 6.47 (s, 1H), 4.49 (s, 2H), 1.91 (s, 3H) |
| 100 | 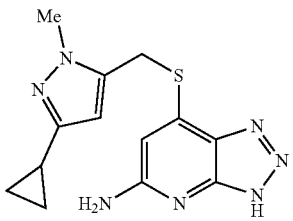 [SMILES: Cn1nc(C2CC2)cc1CSc1cc(N)nc2[nH]nnc12] | 7-(((3-cyclopropyl-1-methyl-1H-pyrazol-5-yl)methyl) thio)-3H-[1,2,3]triazolo[4,5-b]pyridin-5-amine | MS(ESI) 302.1 (M + H)+. 1H NMR (500 MHz, DMSO-$d_6$) δ 6.60 (br. s., 2H), 6.45 (s, 1H), 6.00 (s, 1H), 4.51 (s, 2H), 3.75 (s, 3H), 1.82-1.68 (m, 1H), 0.85-0.71 (m, 2H), 0.62-0.52 (m, 2H) |
| 101 | 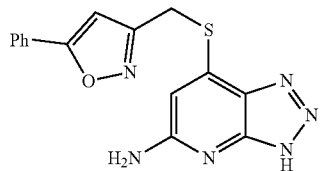 [SMILES: Nc1cc(SCc2cc(-c3ccccc3)on2)c2nn[nH]c2n1] | 7-(((5-phenylisoxazol-3-yl)methyl)thio)-3H-[1,2,3] triazolo[4,5-b]pyridin-5-amine | MS(ESI) 325.1 (M + H)+. 1H NMR (500 MHz, CD3OD) δ 7.77 (dd, J = 7.7, 2.2 Hz, 2H), 7.51-7.36 (m, 3H), 6.76 (s, 1H), 6.59 (s, 1H), 4.50 (s, 2H) |
| 102 | 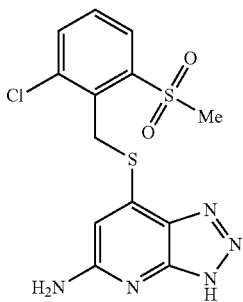 [SMILES: CS(=O)(=O)c1cccc(Cl)c1CSc1cc(N)nc2[nH]nnc12] | 7-((2-chloro-6-(methylsulfonyl)benzyl) thio)-3H-[1,2,3]triazolo[4,5-b]pyridin-5-amine | MS(ESI) 370.0 (M + H)+. |
| 103 | 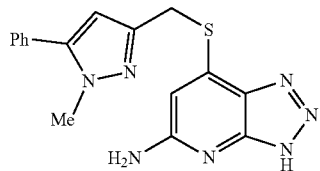 [SMILES: Cn1nc(CSc2cc(N)nc3[nH]nnc23)cc1-c1ccccc1] | 7-(((1-methyl-5-phenyl-1H-pyrazol-3-yl)methyl)thio)-3H-[1,2,3]triazolo[4,5-b] pyridin-5-amine | MS(ESI) 338.1 (M + H)+. 1H NMR (500 MHz, CD3OD) δ 7.53-7.35 (m, 5H), 6.62 (s, 1H), 6.39 (s, 1H), 4.40 (s, 2H), 3.86 (s, 3H) |
| 104 | 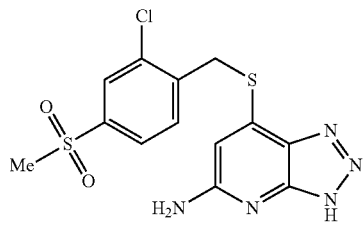 [SMILES: CS(=O)(=O)c1ccc(CSc2cc(N)nc3[nH]nnc23)c(Cl)c1] | 7-((2-chloro-4-(methylsulfonyl)benzyl) thio)-3H-[1,2,3]triazolo[4,5-b]pyridin-5-amine | MS(ESI) 370.0 (M + H)+. |

-continued

| Ex. No. | Structure | Name | Analytical Data |
|---|---|---|---|
| 105 | 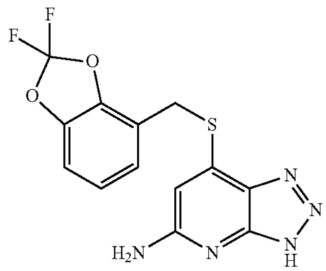 [SMILES: Nc1cc(SCc2cccc3c2OC(F)(F)O3)c2nn[nH]c2n1] | 7-(((2,2-difluorobenzo[d][1,3]dioxol-4-yl)methyl)thio)-3H-[1,2,3]triazolo[4,5-b]pyridin-5-amine | MS(ESI) 338.0 (M + H)⁺. ¹H NMR (500 MHz, DMSO-d₆) δ 7.35 (d, J = 7.9 Hz, 1H), 7.28 (d, J = 7.9 Hz, 1H), 7.23-7.15 (m, 1H), 6.51 (br. s., 1H), 4.60 (s, 2H) |
| 106 | 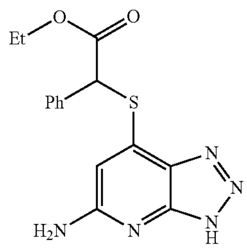 [SMILES: CCOC(=O)C(Sc1cc(N)nc2[nH]nnc12)c1ccccc1] | ethyl 2-((5-amino-3H-[1,2,3]triazolo[4,5-b]pyridin-7-yl)thio)-2-phenylacetate | MS(ESI) 330.1 (M + H)⁺. ¹H NMR (500 MHz, CD₃OD) δ 7.62-7.55 (m, 2H), 7.47-7.36 (m, 3H), 6.65 (s, 1H), 5.89 (s, 1H), 4.33-4.13 (m, 2H), 1.28-1.13 (m, 3H) |
| 107 | 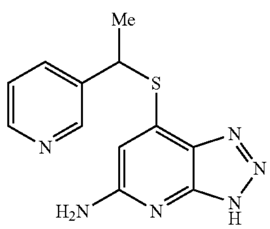 [SMILES: CC(Sc1cc(N)nc2[nH]nnc12)c1cccnc1] | 7-((1-(pyridin-3-yl)ethyl)thio)-3H-[1,2,3]triazolo[4,5-b]pyridin-5-amine | MS(ESI) 273.0 (M + H)⁺. |
| 108 | 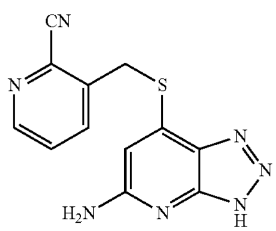 [SMILES: N#Cc1ncccc1CSc1cc(N)nc2[nH]nnc12] | 3-(((5-amino-3H-[1,2,3]triazolo[4,5-b]pyridin-7-yl)thio)methyl)picolinonitrile | MS(ESI) 284.1 (M + H)⁺. NMR (500 MHz, DMSO-d₆) δ 8.69 (s, 1H), 8.11 (d, J = 7.7 Hz, 1H), 7.78-7.67 (m, 1H), 6.46 (s, 1H), 4.75 (s, 2H). |
| 109 | 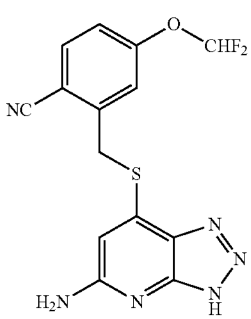 [SMILES: N#Cc1ccc(OC(F)F)cc1CSc1cc(N)nc2[nH]nnc12] | 2-(((5-amino-3H-[1,2,3]triazolo[4,5-b]pyridin-7-yl thio)methyl)-4-(difluoromethoxy)benzonitrile | MS(ESI) 349.1 (M + H)⁺. ¹H NMR (500 MHz, DMSO-d₆) δ 8.00 (m, 1H), 7.55-7.20 (m, 3H), 6.51 (s, 1H), 4.70 (s, 2H). |

-continued

| Ex. No. | Structure | Name | Analytical Data |
|---|---|---|---|
| 110 | 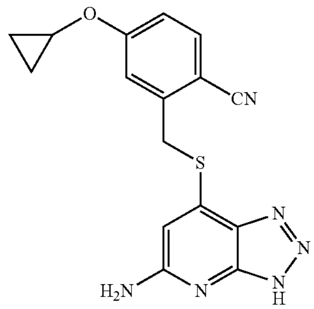 [SMILES: N#Cc1ccc(OC2CC2)cc1CSc1cc(N)nc2[nH]nnc12] | 2-(((5-amino-3H-[1,2,3]triazolo[4,5-b]pyridin-7-yl)thio)methyl)-4-cyclopropoxybenzonitrile | MS(ESI) 339.2 (M + H)+. |
| 111 | 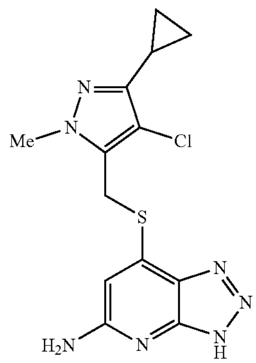 [SMILES: Cn1nc(C2CC2)c(Cl)c1CSc1cc(N)nc2[nH]nnc12] | 7-(((4-chloro-3-cyclopropyl-1-methyl-1H-pyrazol-5-yl)methyl)thio)-3H-[1,2,3]triazolo[4,5-b]pyridin-5-amine | MS(ESI) 336.1 (M + H)+. $^1$H NMR (500 MHz, CD$_3$OD) δ 6.78 (s, 1H), 4.65 (s, 2H), 3.87 (s, 3H), 1.92-1.84 (m, 1H), 0.97-0.90 (m, 2H), 0.90-0.83 (m, 2H). |
| 112 | 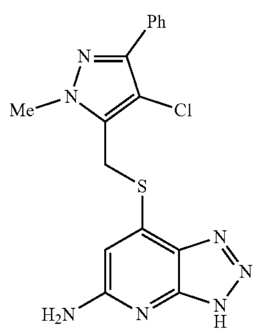 [SMILES: Cn1nc(-c2ccccc2)c(Cl)c1CSc1cc(N)nc2[nH]nnc12] | 7-(((4-chloro-1-methyl-3-phenyl-1H-pyrazol-5-yl)methyl)thio)-3H-[1,2,3]triazolo[4,5-b]pyridin-5-amine | MS(ESI) 372.1 (M + H)+. $^1$H NMR (500 MHz, DMSO-d$_6$) δ 7.95 (s, 1H), 7.80 (m, 2H), 7.51-7.43 (m, 2H), 7.39 (m, 1H), 6.65 (s, 2H), 6.57 (s, 1H), 4.70 (s, 2H), 3.95 (s, 3H). |
| 113 | 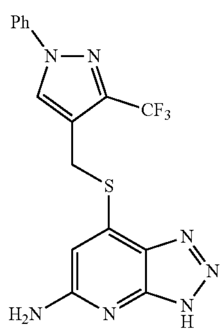 [SMILES: Nc1cc(SCc2cn(-c3ccccc3)nc2C(F)(F)F)c2nn[nH]c2n1] | 7-(((1-phenyl-3-(trifluoromethyl)-1H-pyrazol-4-yl)methyl)thio)-3H-[1,2,3]triazolo[4,5-b]pyridin-5-amine | MS(ESI) 392.1 (M + H)+. $^1$H NMR (500 MHz, CD$_3$OD) δ 8.40 (s, 1H), 7.98 (s, 1H), 7.75 (m, 2H), 7.51 (m, 2H), 7.39 (s, 1H), 6.56 (s, 1H), 4.51 (s, 2H). |
| 114 | 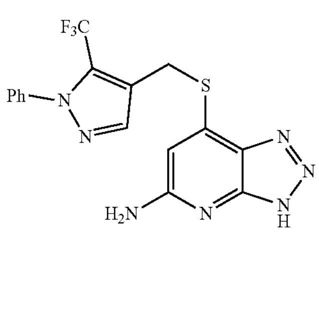 [SMILES: Nc1cc(SCc2cnn(-c3ccccc3)c2C(F)(F)F)c2nn[nH]c2n1] | 7-(((1-phenyl-5-(trifluoromethyl)-1H-pyrazol-4-yl)methyl)thio)-3H-[1,2,3]triazolo[4,5-b]pyridin-5-amine | MS(ESI) 392.1 (M + H)+. $^1$H NMR (500 MHz, CD$_3$OD) δ 7.83 (s, 1H), 7.59-7.51 (m, 3H), 7.49-7.42 (m, 2H), 6.59 (s, 1H), 4.56 (s, 2H). |

-continued

| Ex. No. | Structure | Name | Analytical Data |
|---|---|---|---|
| 115 | 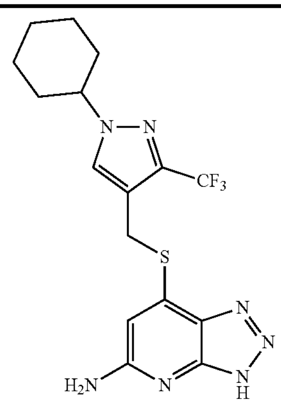 | 7-(((1-cyclohexyl-3-(trifluoromethyl)-1H-pyrazol-4-yl)methyl)thio)-3H-[1,2,3]triazolo[4,5-b]pyridin-5-amine | MS(ESI) 398.2 (M + H)+. 1H NMR (500 MHz, CD3OD) δ 7.90 (s, 1H), 6.67 (br. s., 1H), 4.47 (s, 2H), 4.18 (t, J = 11.4 Hz, 1H), 2.07 (d, J = 12.1 Hz, 2H), 1.89 (d, J = 13.2 Hz, 2H), 1.82-1.67 (m, 3H), 1.46 (q, J = 12.7 Hz, 2H), 1.37-1.20 (m, 1H). |
| 116 | 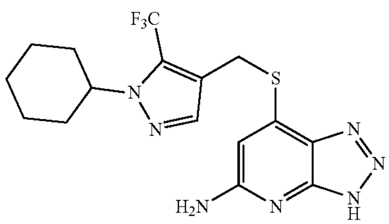 [SMILES: Nc1cc(SCc2cnn(C3CCCCC3)c2C(F)(F)F)c2nn[nH]c2n1] | 7-(((1-cyclohexyl-5-(trifluoromethyl)-1H-pyrazol-4-yl)methyl)thio)-3H-[1,2,3]triazolo[4,5-b]pyridin-5-amine | MS(ESI) 398.2 (M + H)+. 1H NMR (500 MHz, CD3OD) δ 7.69 (s, 1H), 6.68 (s, 1H), 4.51 (s, 2H), 4.30-4.16 (m, 1H), 2.01-1.85 (m, 5H), 1.75 (d, J = 12.4 Hz, 1H), 1.55-1.37 (m, 2H), 1.37-1.21 (m, 1H). |
| 117 | 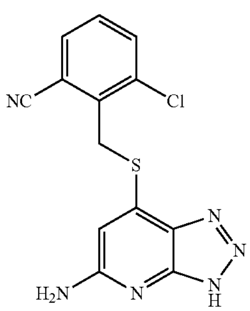 [SMILES: N#Cc1cccc(Cl)c1CSc1cc(N)nc2[nH]nnc12] | 2-(((5-amino-3H-[1,2,3]triazolo[4,5-b]pyridin-7-yl)thio)methyl)-3-chlorobenzonitrile | MS(ESI) 317.1 (M + H)+. |
| 118 | 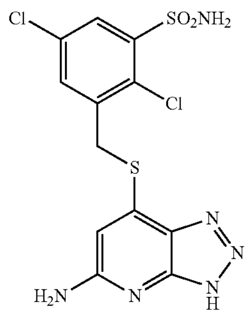 [SMILES: Nc1cc(SCc2cc(Cl)cc(S(N)(=O)=O)c2Cl)c2nn[nH]c2n1] | 3-(((5-amino-3H-[1,2,3]triazolo[4,5-b]pyridin-7-yl)thio)methyl)-2,5-dichlorobenzenesulfonamide | MS(ESI) 405.1 (M + H)+. |
| 119 | 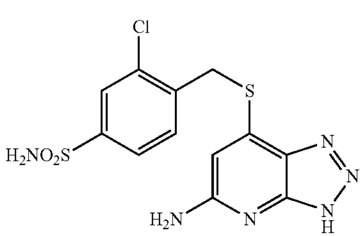 [SMILES: Nc1cc(SCc2ccc(S(N)(=O)=O)cc2Cl)c2nn[nH]c2n1] | 4-(((5-amino-3H-[1,2,3]triazolo[4,5-b]pyridin-7-yl)thio)methyl)-3-chlorobenzenesulfonamide | MS(ESI) 441.2 (M + H)+. |

-continued

| Ex. No. | Structure | Name | Analytical Data |
|---|---|---|---|
| 120 | 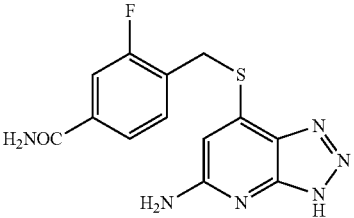 [SMILES: NC(=O)c1ccc(CSc2cc(N)nc3[nH]nnc23)c(F)c1] | 4-(((5-amino-3H-[1,2,3]triazolo[4,5-b]pyridin-7-yl)thio)methyl)-3-fluorobenzamide | MS(ESI) 319.2 (M + H)$^+$. |
| 121 | 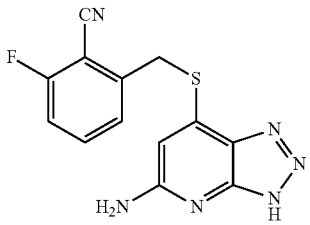 [SMILES: N#Cc1c(F)cccc1CSc1cc(N)nc2[nH]nnc12] | 2-(((5-amino-3H-[1,2,3]triazolo[4,5-b]pyridin-7-yl)thio)methyl)-6-fluorobenzonitrile | MS(ESI) 300.1 (M + H)$^+$. |
| 122 | 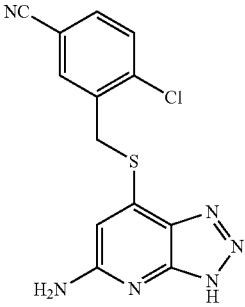 [SMILES: N#Cc1ccc(Cl)c(CSc2cc(N)nc3[nH]nnc23)c1] | 3-(((5-amino-3H-[1,2,3]triazolo[4,5-b]pyridin-7-yl)thio)methyl)-4-chlorobenzonitrile | MS(ESI) 316.0 (M + H)$^+$. |
| 123 | 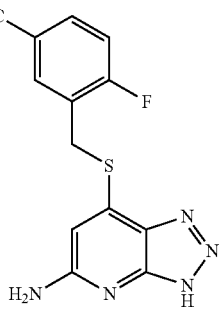 | 3-(((5-amino-3H-[1,2,3]triazolo[4,5-b]pyridin-7-yl)thio)methyl)-4-fluorobenzonitrile | MS(ESI) 300.1 (M + H)$^+$. |
| 124 | 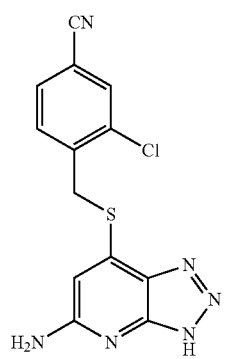 [SMILES: N#Cc1ccc(CSc2cc(N)nc3[nH]nnc23)c(Cl)c1] | 4-(((5-amino-3H-[1,2,3]triazolo[4,5-b]pyridin-7-yl)thio)methyl)-3-chlorobenzonitrile | MS(ESI) 316.0 (M + H)$^+$. |

| Ex. No. | Structure | Name | Analytical Data |
|---|---|---|---|
| 125 | 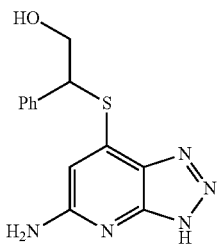 | 7-((quinolin-8-ylmethyl)thio)-3H-[1,2,3]triazolo[4,5-b]pyridin-5-amine | MS(ESI) 309.1 (M + H)+. |

Example 126: 2-((5-Amino-3H-[1,2,3]triazolo[4,5-b]pyridin-7-yl)thio)-2-phenylethanol

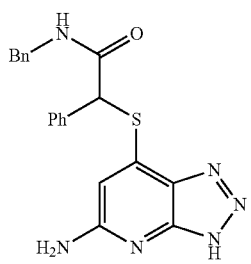 [SMILES: Nc1cc(SC(C(=O)NCc2ccccc2)c2ccccc2)c2nn[nH]c2n1]

LAH (17 μl, 0.061 mmol) was added to a solution of Example 106 (20 mg, 0.061 mmol) in THF (600 μl) and the mixture was stirred over night. The reaction was quenched by the addition of conc. HCl (5 drops) and stirred for 1 h. The mixture was filtered and concentrated. The crude was purified by prep HPLC to yield Example 126 (5.3 mg, 0.013 mmol, 20% yield). MS(ESI) m/z: 288.1 (M+H)+. $^1$H NMR (500 MHz, CD$_3$OD) δ 7.60-7.52 (m, 2H), 7.44-7.36 (m, 2H), 7.36-7.28 (m, 1H), 6.68 (s, 1H), 5.01 (t, J=6.6 Hz, 1H), 4.09 (dd, J=11.8, 6.1 Hz, 1H), 4.01 (dd, J=11.8, 6.9 Hz, 1H).

Example 127: 2-((5-Amino-3H-[1,2,3]triazolo[4,5-b]pyridin-7-yl)thio)-N-benzyl-2-phenylacetamide

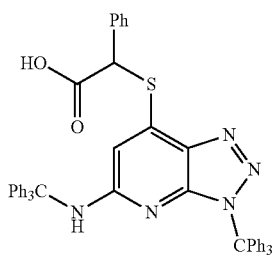

Example 127A: 2-Phenyl-2-((3-trityl-5-(tritylamino)-3H-[1,2,3]triazolo[4,5-b]pyridin-7-yl)thio)acetic Acid Lithium hydroxide (0.66 mL, 0.66 mmol, 1 M aq) was added to a solution of Example 106 (270 mg, 0.33 mmol) in THF (3 mL) and stirred over night. The mixture was diluted with EtOAc. Citric acid (1 mL, sat'd aqueous) was added. The organics were washed with water and brine, dried over Na$_2$SO$_4$ and concentrated in vacuo. The crude reaction mixture was used in the next reaction without purification. MS(ESI) 786.2

Example 127

2,4,6-Tripropyl-1,3,5,2,4,6-trioxatriphosphorinane-2,4,6-trioxide (0.25 mL, 0.41 mmol) was added to a solution of Example 21A (260 mg, 0.33 mmol), benzylamine (0.051 mL, 0.46 mmol) and TEA (0.14 mL, 0.99 mmol) in THF (3 mL) and stirred over night. A 50% sat'd sodium bicarbonate was added was added and the resulting mixture stirred vigorously. After 15 min EtOAc was added, and the resulting mixture was stirred for 15 min. The organic layer was separated, washed with sodium bicarbonate (50% sat'd) and water, dried over Na$_2$SO$_4$ and concentrated in vacuo. The crude product was purified by flash chromatography (loading in chloroform, 0% to 100% ethyl acetate in hexane over 10 min using a 4 g silica gel cartridge) to yield N-benzyl-2-phenyl-2-((3-trityl-5-(tritylamino)-3H-[1,2,3]triazolo[4,5-b]pyridin-7-yl)thio)acetamide (180 mg, 0.206 mmol, 62.2% yield). TFA (0.5 mL) was added to a suspension of N-benzyl-2-phenyl-2-((3-trityl-5-(tritylamino)-3H-[1,2,3]triazolo[4,5-b]pyridin-7-yl)thio)acetamide (40 mg, 0.046 mmol) in CH$_2$Cl$_2$ (0.5 mL). After stirring 15 min, triethylsilane (0.022 mL, 0.14 mmol) was added. After stirring for 2 h at rt, the mixture was concentrated. The crude product was purified by prep HPLC to yield Example 127 (17.1 mg, 0.043 mmol, 95% yield). MS(ESI) 391.1 (M+H)±.

Example 128: 7-((2-(Benzylamino)-1-phenylethyl)thio)-3H-[1,2,3]triazolo[4,5-b]pyridin-5-amine

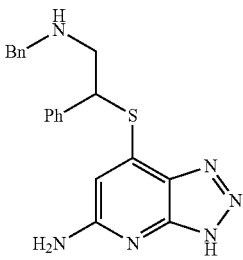 [SMILES: Nc1cc(SC(CNCc2ccccc2)c2ccccc2)c2nn[nH]c2n1]

BH$_3$-THF (640 μl, 0.64 mmol 1 M in THF) was added to a solution of Example 118 (140 mg, 0.160 mmol) in THF (1600 μl) and stirred at 80° C. over night. NH$_4$Cl (4 mL, sat'd aq) was added and the mixture was stirred for 1 h at rt. The mixture was diluted with EtOAc, washed with brine, dried over Na$_2$SO$_4$ and concentrated in vacuo. The crude material was dissolve in DCM. TFA (1 mL) and triethylsilane (0.1 mL) was added. After stirring for 2 h at rt, the mixture was concentrated. The crude product was purified by prep HPLC to yield Example 128 (5.9 mg, 0.016 mmol, 11% yield). MS(ESI) 377.2 (M+H)$^+$. $^1$H NMR (500 MHz, CD$_3$OD) δ 7.49-7.42 (m, 2H), 7.38-7.32 (m, 2H), 7.32-7.23 (m, 6H), 6.45 (s, 1H), 5.15 (m, 1H), 3.96-3.82 (m, 2H), 3.23 (d, J=7.4 Hz, 2H).

Example 129: 2-(((5-Amino-3H-[1,2,3]triazolo[4,5-b]pyridin-7-yl)thio)methyl)-3-(1H-pyrazol-1-yl)benzonitrile

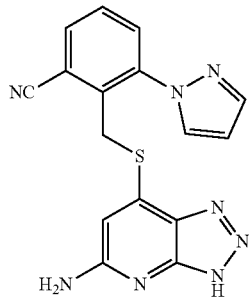 [SMILES: N#Cc1cccc(-n2cccn2)c1CSc1cc(N)nc2[nH]nnc12]

Example 129A: 3-Bromo-2-(bromomethyl)benzonitrile

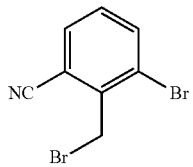 [SMILES: N#Cc1cccc(Br)c1CBr]

Example 129A was synthesized using a procedure similar to that described in Example 12B. MS(ESI) 274.2 (M+H)$^+$.

Example 129B: 3-Bromo-2-(((3-trityl-5-(tritylamino)-3H-[1,2,3]triazolo[4,5-b]pyridin-7-yl)thio)methyl)benzonitrile

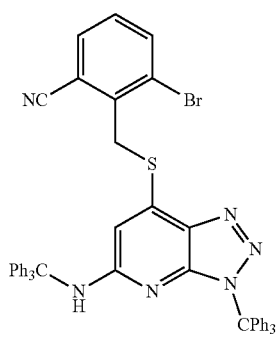

To a solution of ethyl 3-((3-trityl-5-(tritylamino)-3H-[1,2,3]triazolo[4,5-b]pyridin-7-yl)thio)propanoate (300 mg, 0.40 mmol) in THF (2 mL) was added KOtBu (130 mg, 1.2 mmol). After stirring for 1 h, Example 13A (120 mg, 0.44 mmol) was added and the reaction mixture was stirred at room temperature for 10 h. The reaction mixture was loaded onto a 24-g Isco column and eluted with EtOAc/hexanes (0-100%) to obtain Example 129B (250 mg, 0.30 mmol, 74% yield).

Example 129

Example 129B (100 mg, 0.12 mmol), 1H-pyrazole (80 mg, 1.2 mmol), CuI (34 mg, 0.18 mmol), K$_2$CO$_3$ (49 mg, 0.36 mmol), quinolin-8-ol (26 mg, 0.18 mmol) and DMSO (1 mL) were added to a 5 mL microwave vial. The vial was quickly purged with argon and capped, and the contents were stirred at 100° C. overnight. DCM (1 mL), TFA (2 mL) and triethylsilane (0.048 mL, 0.03 mmol) were added to the reaction mixture and stirred for 20 min. The reaction mixture was concentrated and purified by preparatory HPLC to yield Example 129. MS(ESI) 349.1 (M+H)$^+$.

Example 130: 3-(((5-Amino-3H-[1,2,3]triazolo[4,5-b]pyridin-7-yl)thio)methyl)-4-(pyridin-4-yl)benzonitrile

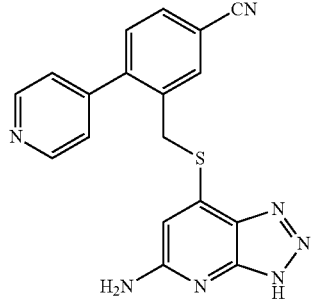 [SMILES: N#Cc1ccc(-c2ccncc2)c(CSc2cc(N)nc3[nH]nnc23)c1]

To a solution of 4-iodo-3-(((3-trityl-5-(tritylamino)-3H-[1,2,3]triazolo[4,5-b]pyridin-7-yl)thio)methyl)benzonitrile (synthesized from 4-iodo-3-methylbenzonitrile using procedures in Example 120) ((80 mg, 0.090 mmol) in toluene/water (1.1 mL, 10:1) under nitrogen was added 4-(4,4,5,5-tetramethyl-1,3,2-dioxaborolan-2-yl)pyridine (45.9 mg, 0.224 mmol), tricyclohexylphosphine (84 mg, 0.090 mmol), phosphoric acid, potassium salt (57 mg, 0.27 mmol) and palladium (II) acetate (10 mg, 0.045 mmol). The reaction mixture was microwaved at 100° C. for 1 h. DCM (1 mL), TFA (2 mL) and triethylsilane (0.048 mL, 0.03 mmol) were added to the reaction mixture and stirred for 20 min. The reaction mixture was concentrated and purified by preparatory HPLC to yield Example 130. MS(ESI) 360.1 (M+H)$^+$. $^1$H NMR (500 MHz, DMSO-d$_6$) δ 8.68 (br. s., 2H), 8.13 (s, 1H), 7.93 (dd, J=8.0, 1.4 Hz, 1H), 7.60-7.43 (m, 3H), 6.61 (br. s., 2H), 6.29 (s, 1H), 4.47 (s, 2H).

The following compounds were prepared in a manner similar to experimental procedures that are described in Examples 120 and 121 using the aryl iodide or bromide as starting material. The aryl iodide and bromide can be prepared using procedures previous shown in this patent from commercially available starting material.

| Ex. No. | Structure | Name | Analytical Data |
|---|---|---|---|
| 131 | 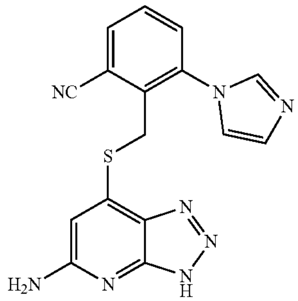 [SMILES: N#Cc1cccc(-n2ccnc2)c1CSc1cc(N)nc2[nH]nnc12] | 2-(((5-amino-3H-[1,2,3]triazolo[4,5-b]pyridin-7-yl)thio)methyl)-3-(1H-imidazol-1-yl)benzonitrile | MS(ESI) 349.1 (M + H)+. |
| 132 | 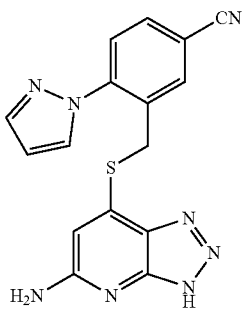 [SMILES: N#Cc1ccc(-n2cccn2)c(CSc2cc(N)nc3[nH]nnc23)c1] | 3-(((5-amino-3H-[1,2,3]triazolo[4,5-b]pyridin-7-yl)thio)methyl)-4-(1H-pyrazol-1-yl)benzonitrile | MS(ESI) 349.1 (M + H)+. $^1$H NMR (500 MHz, DMSO-$d_6$) δ 8.31 (br. s., 1H), 8.18 (br. s., 1H), 8.00-7.95 (m, 1H), 7.87 (s, 1H), 7.73 (d, J = 8.0 Hz, 1H), 7.22 (s, 1H), 7.12 (s, 1H), 7.02 (s, 1H), 6.62 (br. s., 2H), 6.45-6.24 (m, 1H), 4.76 (br. s., 2H) |
| 133 | 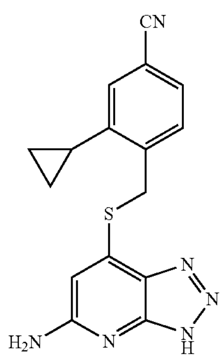 [SMILES: N#Cc1ccc(CSc2cc(N)nc3[nH]nnc23)c(C2CC2)c1] | 4-(((5-amino-3H-[1,2,3]triazolo[4,5-b]pyridin-7-yl)thio)methyl)-3-cyclopropylbenzonitrile | MS(ESI) 323.1 (M + H)+. $^1$H NMR (500 MHz, DMSO-$d_6$) δ 7.70-7.56 (m, 2H), 7.50 (d, J = 8.0 Hz, 1H, 6.58-6.43 (m, 1H), 4.73 (s, 2H), 2.18 (s, 1H), 1.08-0.96 (m, 2H), 0.84 (dd, J = 5.2, 1.9 Hz, 2H) |

Example 134: 7-(((3-Cyclopropyl-1-phenyl-1H-pyrazol-4-yl)methyl)thio)-3H-[1,2,3]triazolo[4,5-b]pyridin-5-amine

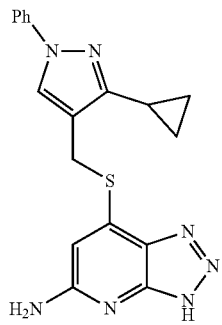 [SMILES: Nc1cc(SCc2cn(-c3ccccc3)nc2C2CC2)c2nn[nH]c2n1]

Example 134A: Ethyl 3-cyclopropyl-1-phenyl-1H-pyrazole-4-carboxylate

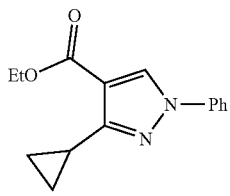 [SMILES: CCOC(=O)c1cn(-c2ccccc2)nc1C1CC1]

A mixture of ethyl 3-cyclopropyl-1H-pyrazole-4-carboxylate (0.50 g, 2.8 mmol), $K_2CO_3$ (0.84 g, 6.1 mmol) and CuI (0.16 g, 0.83 mmol) in toluene (2.8 ml) was degassed with Ar. Iodobenzene (0.37 ml, 3.3 mmol) and N,N'-dimethylenediamine (0.18 ml, 1.7 mmol) were added and the mixture was heated in a sealed tube at 110° C. for 16 h. The mixture was diluted with EtOAc, filtered and concentrated. The crude product was purified by flash chromatography (loading in chloroform, 0% to 50% ethyl acetate in hexane over 15 min using a 24 g silica gel cartridge) to yield Example 134A (440 mg, 1.7 mmol, 62% yield) as a white solid. ¹H NMR (400 MHz, CDCl₃) δ 8.30 (s, 1H), 7.70-7.61 (m, 2H), 7.47-7.40 (m, 2H), 7.33-7.27 (m, 1H), 4.34 (q, J=7.3 Hz, 2H), 2.65-2.54 (m, 1H), 1.38 (t, J=7.0 Hz, 3H), 1.10-0.96 (m, 4H).

Example 134B:
(3-Cyclopropyl-1-phenyl-1H-pyrazol-4-yl)methanol

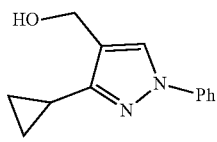 [SMILES: OCc1cn(-c2ccccc2)nc1C1CC1]

LAH (0.039 g, 1.0 mmol) was added portionwise to a solution of Example 127A (0.13 g, 0.51 mmol) in THF (5.1 ml) at 0° C. over 15 min. The mixture was stirred for 3 h at rt. NaOH (1 M, 0.3 mL) was added dropwise. MgSO₄ was added and the mixture was stirred for 1 h. The mixture was filtered and concentrated. The crude product was purified by flash chromatography (loading in chloroform, 0% to 75% ethyl acetate in hexane over 15 min using a 40 g silica gel cartridge) to yield Example 134B (0.058 g, 0.27 mmol, 53% yield) as a white solid. ¹H NMR (400 MHz, CDCl₃) δ 7.82 (s, 1H), 7.64-7.58 (m, 2H), 7.45-7.35 (m, 2H), 7.22 (tt, J=7.4, 1.1 Hz, 1H), 4.71 (d, J=4.2 Hz, 2H), 2.00-1.90 (m, 1H), 1.50 (t, J=4.8 Hz, 1H), 1.04-0.90 (m, 4H).

Example 134C: 4-(Chloromethyl)-3-cyclopropyl-1-phenyl-1H-pyrazole

Thionyl chloride (0.040 ml, 0.54 mmol) was added to a solution of Example 134B (0.058 g, 0.27 mmol) in DCM (3 ml) and stirred at rt for 3 h. The mixture was concentrated in vacuo and the product was used without further purification. ¹H NMR (500 MHz, CDCl₃) δ 7.85 (s, 1H), 7.63-7.57 (m, 2H), 7.45-7.38 (m, 2H), 7.25-7.20 (m, 1H), 4.68 (s, 2H), 1.99-1.88 (m, 1H), 1.05-0.94 (m, 4H).

Example 134

Example 134 was synthesized from Example 134C using conditions found in Example 11. MS(ESI) 364.2 (M+H)⁺. ¹H NMR (500 MHz, CD₃OD) δ 8.12 (s, 1H), 7.98 (s, 1H), 7.63 (m, 2H), 7.43 (m, 2H), 7.29-7.22 (m, 1H), 6.60 (s, 1H), 4.48 (s, 2H), 2.00 (m, 1H), 1.01-0.90 (m, 4H).

The following compounds were prepared in a manner similar to experimental procedures that are described in Example 127 using ethyl 3-((3-trityl-5-(tritylamino)-3H-[1,2,3]triazolo[4,5-b]pyridin-7-yl)thio)propanoate and the appropriately substituted pyrazole ester as starting material.

| Ex. No. | Structure | Name | Analytical Data |
|---|---|---|---|
| 135 | 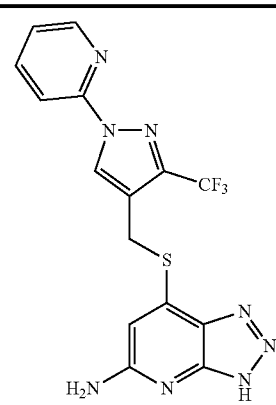 | 7-(((1-(pyridin-2-yl)-3-(trifluoromethyl)-1H-pyrazol-4-yl)methyl)thio)-3H-[1,2,3]triazolo[4,5-b]pyridin-5-amine | MS(ESI) 393.2 (M + H)⁺. ¹H NMR (500 MHz, CD₃OD) δ 8.76 (s, 1H), 8.44 (d, J = 4.7 Hz, 1H), 8.03-7.95 (m, 2H), 7.38 (td, J = 5.0, 3.4 Hz, 1H), 6.62 (s, 1H), 4.55 (s, 2H). |
| 136 | 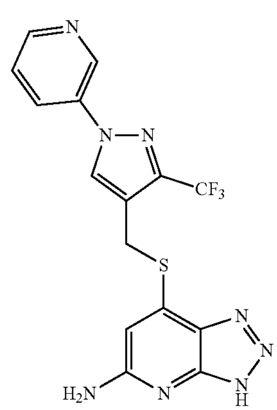 [SMILES: Nc1cc(SCc2cn(-c3cccnc3)nc2C(F)(F)F)c2nn[nH]c2n1] | 7-(((1-(pyridin-2-yl)-3-(trifluoromethyl)-1H-pyrazol-4-yl)methyl)thio)-3H-[1,2,3]triazolo[4,5-b]pyridin-5-amine | MS(ESI) 393.1 (M + H)⁺. ¹H NMR (500 MHz, CD₃OD) δ 9.05 (d, J = 2.5 Hz, 1H), 8.63 (s, 1H), 8.58 (dd, J = 4.8, 1.0 Hz, 1H), 8.32-8.24 (m, 1H), 7.97 (s, 1H), 7.61 (dd, J = 8.4, 4.8 Hz, 1H), 6.69 (s, 1H), 4.59 (s, 2H). |

| Ex. No. | Structure | Name | Analytical Data |
|---|---|---|---|
| 137 | 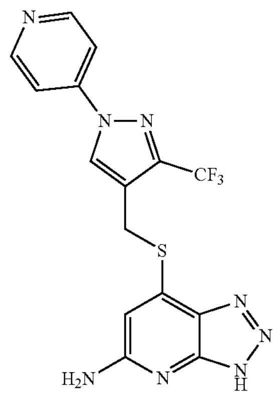 [SMILES: Nc1cc(SCc2cn(-c3ccncc3)nc2C(F)(F)F)c2nn[nH]c2n1] | 7-(((1-(pyridin-2-yl)-3-(trifluoromethyl)-1H-pyrazol-4-yl)methyl)thio)-3H-[1,2,3]triazolo[4,5-b]pyridin-5-amine | MS(ESI) 393.1 (M + H)+. |
| 138 | 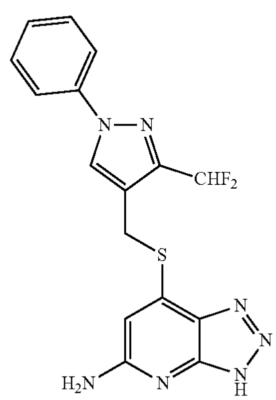 [SMILES: Nc1cc(SCc2cn(-c3ccccc3)nc2C(F)F)c2nn[nH]c2n1] | 7-(((3-(difluoromethyl)-1-phenyl-1H-pyrazol-4-yl)methyl)thio)-3H-[1,2,3]triazolo[4,5-b]pyridin-5-amine | MS(ESI) 374.1 (M + H)+. <br> 1H NMR (500 MHz, CD3OD) δ 8.41 (s., 1H), 7.76 (m, 2H), 7.50 (m, 2H), 7.37 (m 1H), 6.96 (t, J = 54.7 Hz, 1H), 6.71 (s., 1H), 4.59 (s., 2H). |
| 139 | 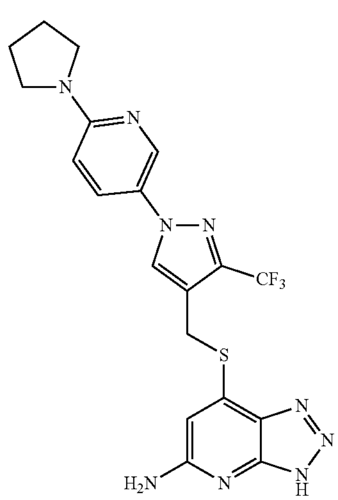 [SMILES: Nc1cc(SCc2cn(-c3ccc(N4CCCC4)nc3)nc2C(F)(F)F)c2nn[nH]c2n1] | 7-(((1-(pyrrolidin-1-yl)pyridin-3-yl-)-3-(trifluoromethyl)-1H-pyrazol-4-yl)methyl)thio)-3H-[1,2,3]triazolo[4,5-b]pyridin-5-amine | MS(ESI) 462.2 (M + H)+. <br> 1H NMR (500 MHz, CD3OD) δ 8.34 (m, 2H), 8.06 (m, 1H), 6.86 (m, 1H), 6.61 (s., 1H), 4.54 (s., 2H), 3.55 (m, 4H), 2.11 (m, 4H). |

| Ex. No. | Structure | Name | Analytical Data |
|---|---|---|---|
| 140 | 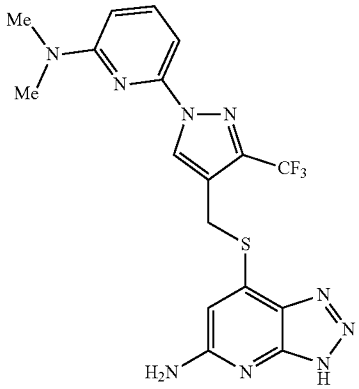 [SMILES: CN(C)c1cccc(-n2cc(CSc3cc(N)nc4[nH]nnc34)c(C(F)(F)F)n2)n1] | 7-(((1-(6-(dimethylamino)pyridin-2-yl)-3-(trifluoromethyl)-1H-pyrazol-4-yl)methyl)thio)-3H-[1,2,3]triazolo[4,5-b]pyridin-5-amine | MS(ESI) 436.2 (M + H)+. $^1$H NMR (500 MHz, CD$_3$OD) δ 8.54 (s, 1H), 7.66-7.59 (m, 1H), 7.09 (d, J = 7.7 Hz, 1H), 6.60-6.54 (m, 2H), 4.58-4.51 (m, 3H), 3.08 (s, 6H). |
| 141 | 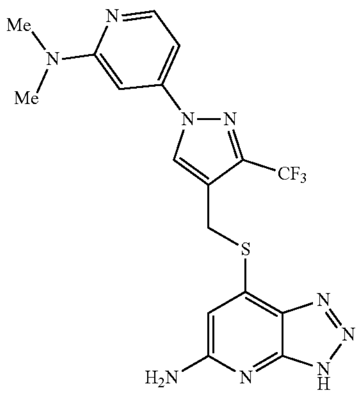 [SMILES: CN(C)c1cc(-n2cc(CSc3cc(N)nc4[nH]nnc34)c(C(F)(F)F)n2)ccn1] | 7-(((1-(2-(dimethylamino)pyridin-4-yl)-3-(trifluoromethyl)-1H-pyrazol-4-yl)methyl)thio)-3H-[1,2,3]triazolo[4,5-b]pyridin-5-amine | MS(ESI) 436.2 (M + H)+. |
| 142 | 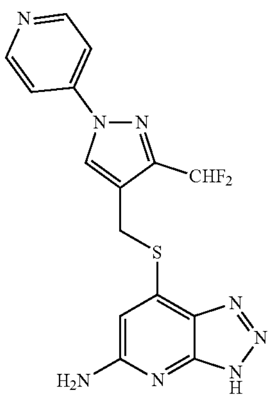 [SMILES: Nc1cc(SCc2cn(-c3ccncc3)nc2C(F)F)c2nn[nH]c2n1] | 7-(((3-(difluoromethyl)-1-pyridin-4-yl)-1H-pyrazol-4-yl)methyl)thio)-3H-[1,2,3]triazolo[4,5-b]pyridin-5-amine | MS(ESI) 375.1 (M + H)+. $^1$H NMR (500 MHz, CD$_3$OD) δ 8.87-8.69 (m, 3H), 8.17 (d, J = 6.1 Hz, 2H), 7.04 (t, J = 53.6 Hz, 1H), 6.71 (s, 1H), 4.63 (s, 2H). |
| 143 | 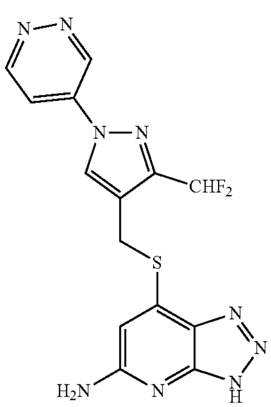 [SMILES: Nc1cc(SCc2cn(-c3ccnnc3)nc2C(F)F)c2nn[nH]c2n1] | 7-(((3-(difluoromethyl)-1-pyridazin-4-yl)-1H-pyrazol-4-yl)methyl)thio)-3H-[1,2,3]triazolo[4,5-b]pyridin-5-amine | MS(ESI) 376.0 (M + H)+. $^1$H NMR (500 MHz, DMSO-d$_6$) δ 9.82 (m, 1H), 9.33 (m), 9.01 (s, 1H), 8.10 (m1H), 7.31 (s, 1H), 6.46 (br. s., 1H), 4.50 (s, 2H) |

-continued

| Ex. No. | Structure | Name | Analytical Data |
|---|---|---|---|
| 144 | 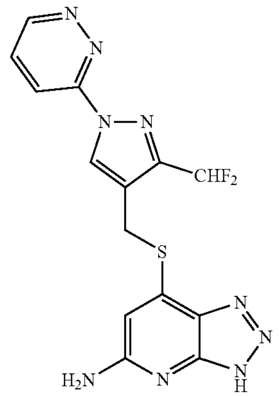 [SMILES: Nc1cc(SCc2cn(-c3cccnn3)nc2C(F)F)c2nn[nH]c2n1] | 7-(((3-(difluoromethyl)-1-pyridazin-3-yl)-1H-pyrazol-4-yl)methyl)thio)-3H-[1,2,3]triazolo[4,5-b]pyridin-5-amine | MS(ESI) 376.1 (M + H)+. ¹H NMR (500 MHz, DMSO-d₆) δ 9.26 (d, J = 3.7 Hz, 1H), 9.01 (s, 1H), 8.20 (d, J = 7.9 Hz, 1H), 8.02 - 7.89 (m, 2H), 7.31 (t, J = 53.1 Hz, 1H), 6.61 (br. s., 1H), 4.55 (s, 2H) |
| 145 | 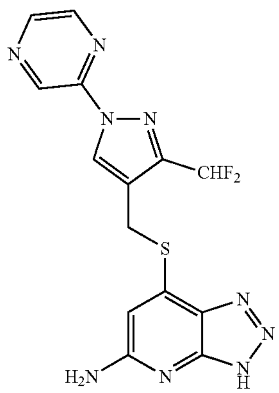 [SMILES: Nc1cc(SCc2cn(-c3cnccn3)nc2C(F)F)c2nn[nH]c2n1] | 7-(((3-(difluoromethyl)-1-pyrazin-2-yl)-1H-pyrazol-4-yl)methyl)thio)-3H-[1,2,3]triazolo[4,5-b]pyridin-5-amine | MS(ESI) 376.1 (M + H)+. ¹H NMR (500 MHz, DMSO-d₆) δ 9.18 (s, 1H), 8.76 (s, 1H), 8.68 (d, J = 2.4 Hz, 1H), 8.58 (s, 1H), 7.30 (t, J = 53.4 Hz, 1H), 6.54 (br. s., 1H), 4.53 (s, 2H) |
| 146 | 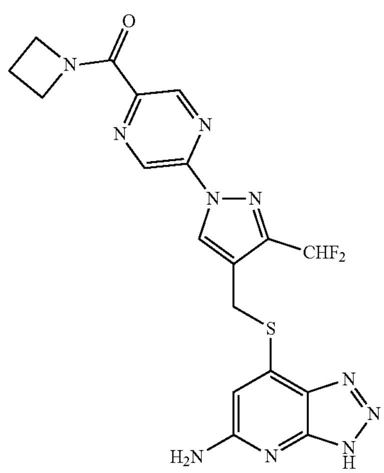 [SMILES: Nc1cc(SCc2cn(-c3cnc(C(=O)N4CCC4)cn3)nc2C(F)F)c2nn[nH]c2n1] | (5-(4-(((5-amino-3H-[1,2,3]triazolo[4,5-b]pyridin-7-yl)thio)methyl)-3-(difluoromethyl)-1H-pyrazol-1-yl)pyrazin-2-yl)(azetidin-1-yl)methanone | MS(ESI) 459.1 (M + H)+. ¹H NMR (500 MHz, DMSO-d₆) δ 9.19 (s, 1H), 9.01 (s, 1H), 8.85 (s, 1H), 7.36 (t, J = 51.9 Hz, 1H), 6.68 (br. s., 2H), 6.58 (br. s., 1H), 4.70-4.52 (m, 4H), 4.16 (t, J = 7.5 Hz, 2H), 2.35 (quin, J = 7.6 Hz, 2H) |
| 147 | 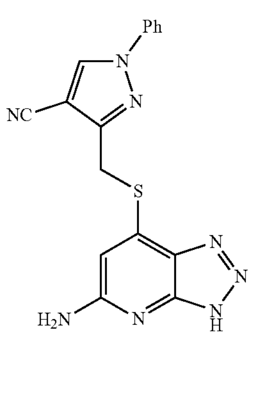 [SMILES: N#Cc1cn(-c2ccccc2)nc1CSc1cc(N)nc2[nH]nnc12] | 3-(((5-amino-3H-[1,2,3]triazolo[4,5-b]pyridin-7-yl)thio)methyl)-1-phenyl-1H-pyrazol-4-carbonitrile | MS(ESI) 349.1 (M + H)+. ¹H NMR (500 MHz, DMSO-d₆) δ 8.32 (s, 1H), 7.68-7.49 (m, 5H), 6.64 (br. s., 2H), 6.42 (s, 1H), 4.83 (s, 2H) |

| Ex. No. | Structure | Name | Analytical Data |
|---|---|---|---|
| 148 | 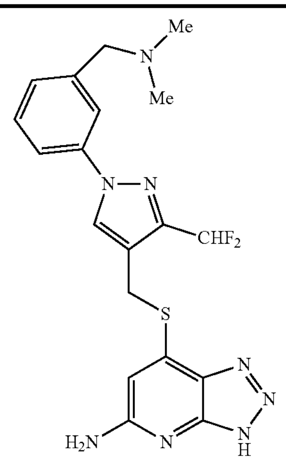 | 7-(((3-(difluoromethyl)-1-(3-((dimethylamino)methyl)phenyl)-1H-pyrazol-4-yl)methyl)thio)-3H-[1,2,3]triazolo[4,5-b]pyridin-5-amine | MS(ESI) 431.2 (M + H)+. |
| 149 | 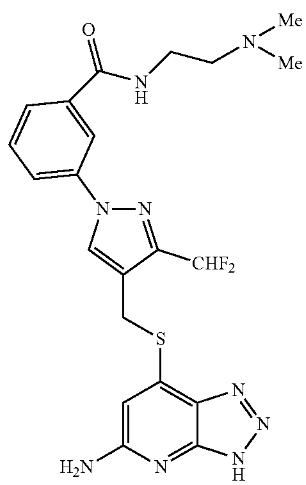 [SMILES: CN(C)CCNC(=O)c1cccc(-n2cc(CSc3cc(N)nc4[nH]nnc34)c(C(F)F)n2)c1] | 3-(4-(((5-amino-3H-[1,2,3]triazolo[4,5-b]pyridin-7-yl)thio)methyl)-3-(difluoromethyl)-1H-pyrazol-1-yl)-N-(2-(dimethylamino)ethyl)benzamide | MS(ESI) 488.2 (M + H)+. $^1$H NMR (500 MHz, DMSO-$d_6$) δ 8.86 (t, J = 5.5 Hz, 1H), 8.72 (s, 1H), 8.25 (s, 1H), 7.97 (d, J = 7.9 Hz, 1H), 7.84 (d, J = 7.9 Hz, 1H), 7.66 (t, J = 8.1 Hz, 1H), 7.23 (t, J = 53.7 Hz, 1H), 6.54 (s, 1H), 4.49 (s, 2H), 3.59 (d, J = 10.4 Hz, 1H), 3.27 (br. s., 2H), 2.84 (s, 7H) |
| 150 | 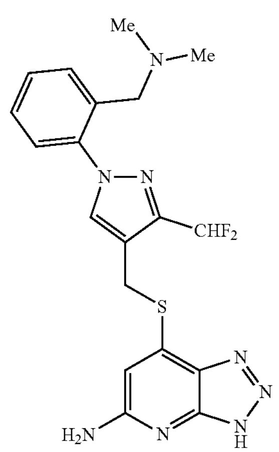 [SMILES: CN(C)Cc1ccccc1-n1cc(CSc2cc(N)nc3[nH]nnc23)c(C(F)F)n1] | 7-(((3-(difluoromethyl)-1-(2-((dimethylamino)methyl)phenyl)-1H-pyrazol-4-yl)methyl)thio)-3H-[1,2,3]triazolo[4,5-b]pyridin-5-amine | MS(ESI) 431.1 (M + H)+. $^1$H NMR (500 MHz, DMSO-$d_6$) δ 8.56 (s, 1H), 7.76-7.63 (m, 3H), 7.63-7.53 (m, 1H), 7.42-7.01 (m, 2H), 6.53 (s, 1H), 4.51 (s, 2H), 4.30 (s, 2H), 2.76 (s, 6H) |

| Ex. No. | Structure | Name | Analytical Data |
|---|---|---|---|
| 151 | 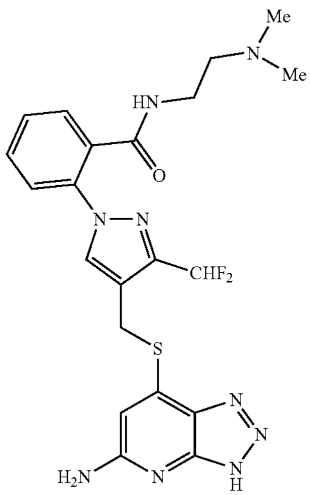 [SMILES: CN(C)CCNC(=O)c1ccccc1-n1cc(CSc2cc(N)nc3[nH]nnc23)c(C(F)F)n1] | 2-(4-(((5-amino-3H-[1,2,3]triazolo[4,5-b]pyridin-7-yl)thio)methyl)-3-(difluoromethyl)-1H-pyrazol-1-yl)-N-(2-(dimethylamino)ethyl)benzamide | MS(ESI) 488.1 (M + H)$^+$. $^1$H NMR (500 MHz, DMSO-d$_6$) δ 8.37 (br. s., 1H), 8.32 (br. s., 1H), 8.26 (s, 1H), 7.72-7.56 (m, 4H), 7.21 (t, J = 55.2 Hz, 1H), 6.65 (br. s., 1H), 6.57 (s, 1H), 4.53 (s, 2H), 3.71 (br. s., 2H), 3.33-3.22 (m, 2H), 2.34-2.27 (m, 6H) |
| 152 | 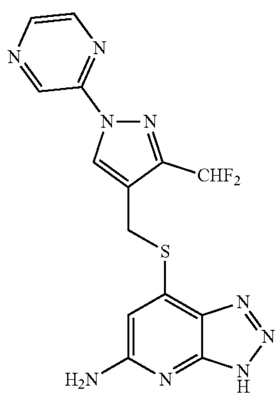 [SMILES: Nc1cc(SCc2cn(-c3cnccn3)nc2C(F)F)c2nn[nH]c2n1] | 7-(((3-(difluoromethyl)-1-(pyrazin-2-yl)-1H-pyrazol-4-yl)methyl)thio)-3H-[1,2,3]triazolo[4,5-b]pyridin-5-amine | MS(ESI) 376.1 (M + H)$^+$. $^1$H NMR (500 MHz, DMSO-d$_6$) δ 9.18 (s, 1H), 8.76 (s, 1H), 8.68 (d, J = 2.4 Hz, 1H), 8.58 (s, 1H), 7.30 (t, J = 53.4 Hz, 1H), 6.54 (br. s., 1H), 4.53 (s, 2H) |
| 153 | 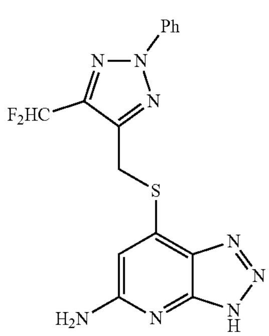 [SMILES: Nc1cc(SCc2nn(-c3ccccc3)nc2C(F)F)c2nn[nH]c2n1] | 7-(((5-(difluoromethyl)-2-phenyl-2H-1,2,3-triazol-4-yl)methyl)thio)-3H-[1,2,3]triazolo[4,5-b]pyridin-5-amine | MS(ESI) 376.1 (M + H)$^+$. $^1$H NMR (500 MHz, DMSO-d$_6$) δ 7.99 (d, J = 8.2 Hz, 2H), 7.60 (t, J = 7.6 Hz, 2H), 7.54-7.33 (m, 2H), 6.62 (br. s., 1H), 4.74 (s, 2H) |

Example 154: 2-(((5-Amino-3H-[1,2,3]triazolo[4,5-d]pyrimidin-7-yl)thio)methyl)-3-fluorobenzonitrile

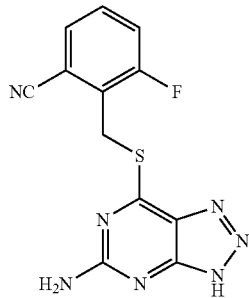 [SMILES: N#Cc1cccc(F)c1CSc1nc(N)nc2[nH]nnc12]

To a mixture of Intermediate 4 (50 mg, 0.22 mmol), and ethyl 3-mercaptopropanoate (90 mg, 0.67 mmol) in DMSO (1 mL) was added $Cs_2CO_3$ (220 mg, 0.67 mmol) and stirred at room temperature overnight. 3-(5-Amino-7-mercapto-3H-[1,2,3]triazolo[4,5-d]pyrimidin-3-yl)propanenitrile was detected by LC/MS (MS(ESI) 222.2 (M+H)$^+$.) 2-(Bromomethyl)-3-fluorobenzonitrile (150 mg, 0.68 mmol) was added to the reaction mixture and it was stirred at room temperature for 2 h. Potassium tert-butoxide (100 mg, 0.90 mmol) was added to the reaction mixture. After stirring for 15 min showed mass of the desired product, methanol (1 mL) added to quench reaction. The reaction mixture was partially concentrated and purified by prep HPLC to yield Example 154. MS(ESI) 302.1 (M+H)$^+$. $^1$H NMR (500 MHz, DMSO-$d_6$) δ 7.81-7.53 (m, 3H), 6.99 (br. s., 2H), 4.80 (s, 2H).

The following compounds were prepared in a manner similar to experimental procedures that are described in Example 147 using Intermediate 4 the appropriate alkyl chloride or bromide as starting material. The alkyl chloride and bromide can be prepared from the corresponding ester or alcohol using standard procedures.

| Ex. No. | Structure | Name | Analytical Data |
|---|---|---|---|
| 155 | 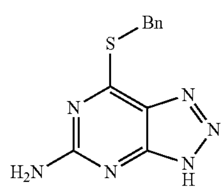 [SMILES: Nc1nc(SCc2ccccc2)c2nn[nH]c2n1] | 7-(benzylthio)-3H-[1,2,3]triazolo[4,5-d]pyrimidin-5-amine | MS(ESI) 259.3 (M + H)$^+$. $^1$H NMR (500 MHz, CD$_3$OD) δ 7.52-7.44 (m, 2H), 7.37-7.20 (m, 3H), 4.64 (s, 2H) |
| 156 | 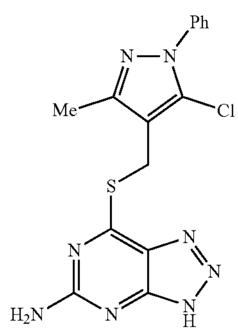 | 7-(((5-chloro-3-methyl-1-phenyl-1H-pyrazol-4-yl)methyl)thio)-3H-[1,2,3]triazolo[4,5-b]pyrimidin-5-amine | MS(ESI) 373.1 (M + H)$^+$. $^1$H NMR (500 MHz, DMSO-$d_6$) δ 7.63-7.31 (m, 5H), 4.53 (s, 2H), 2.30 (s, 3H) |
| 157 | 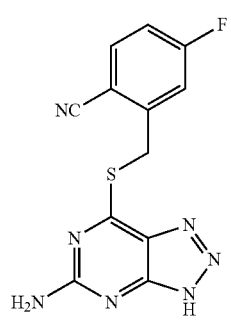 [SMILES: N#Cc1ccc(F)cc1CSc1nc(N)nc2[nH]nnc12] | 2-(((5-amino-3H-[1,2,3]triazolo[4,5-d]pyrimidin-7-yl)thio)methyl)-4-fluorobenzonitrile | MS(ESI) 302.1 (M + H)$^+$. $^1$H NMR (500 MHz, DMSO-$d_6$) δ 8.02-7.91 (m, 1H), 7.80 (d, J = 9.5 Hz, 1H), 7.34 (t, J = 8.1 Hz, 1H) 4.73 (s, 2H) |

-continued

| Ex. No. | Structure | Name | Analytical Data |
|---|---|---|---|
| 158 | 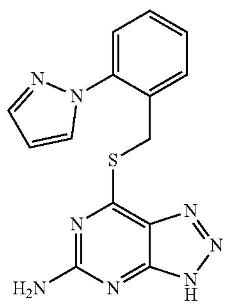 [SMILES: Nc1nc(SCc2ccccc2-n2cccn2)c2nn[nH]c2n1] | 7-((2-(1H-pyrazol-1-yl)benzyl)thio)-3H-[1,2,3]triazolo[4,5-d]pyrimidin-5-amine | MS(ESI) 325.1 (M + H)+. <sup>1</sup>H NMR (500 MHz, DMSO-d<sub>6</sub>) δ 8.12 (s, 1H), 7.91-7.79 (m, 2H), 7.49-7.33 (m, 3H), 6.57 (s, 1H), 4.75-4.63 (m, 2H) |
| 159 | 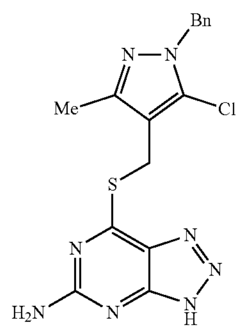 [SMILES: Cc1nn(Cc2ccccc2)c(Cl)c1CSc1nc(N)nc2[nH]nnc12] | 7-(((1-benzyl-5-chloro-3-methyl-1H-pyrazol-4-yl)methyl)thio)-3H-[1,2,3]triazolo[4,5-d]pyrimidin-5-amine | MS(ESI) 387.1 (M + H)+. <sup>1</sup>H NMR (500 MHz, DMSO-d<sub>6</sub>) δ 7.44-7.33 (m, 3H), 7.23 (d, J = 7.3 Hz, 1H), 7.12 (br. s., 2H), 5.34 (s, 2H), 4.53 (s, 2H), 2.28 (s, 3H) |
| 160 | 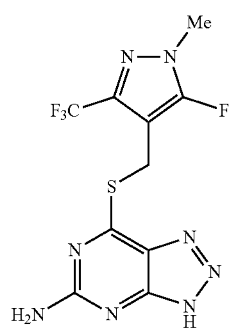 [SMILES: Cn1nc(C(F)(F)F)c(CSc2nc(N)nc3[nH]nnc23)c1F] | 7-(((5-fluoro-1-methyl-3-(trifluoromethyl)-1H-pyrazol-4-yl)methyl)thio)-3H-[1,2,3]triazolo[4,5-d]pyrimidin-5-amine | MS(ESI) 349.1 (M + H)+. <sup>1</sup>H NMR (500 MHz, DMSO-d<sub>6</sub>) δ 4.51 (s, 2H), 2.57-2.32 (m, 3H) |
| 161 | 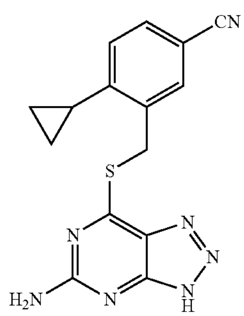 [SMILES: N#Cc1ccc(C2CC2)c(CSc2nc(N)nc3[nH]nnc23)c1] | 3-(((5-amino-3H-[1,2,3]triazolo[4,5-d]pyrimidin-7-yl)thio)methyl)-4-cyclopropylbenzonitrile | MS(ESI) 324.1 (M + H)+. <sup>1</sup>H NMR (500 MHz, DMSO-d<sub>6</sub>) δ 8.13 (s, 1H), 7.77-7.65 (m, 1H), 7.20 (d, J = 8.2 Hz, 1H), 4.88 (s, 2H), 1.30 (br. s., 1H), 1.16 (br. s., 2H), 0.87 (d, J = 4.6 Hz, 2H) |

-continued

| Ex. No. | Structure | Name | Analytical Data |
|---|---|---|---|
| 162 | 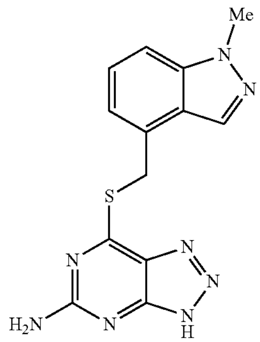 [SMILES: Cn1ncc2c(CSc3nc(N)nc4[nH]nnc34)cccc21] | 7-(((1-methyl-1H-indazol-4-yl)methyl)thio)-3H-[1,2,3]triazolo[4,5-d]pyrimidin-5-amine | MS(ESI) 313.1 (M + H)$^+$. $^1$H NMR (500 MHz, DMSO-$d_6$) δ 8.21 (s, 1H), 7.53 (d, J = 7.9 Hz, 1H), 7.40-7.25 (m, 2H), 4.95 (s, 2H), 4.02 (s, 3H) |
| 163 | 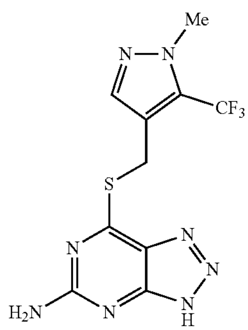 [SMILES: Cn1ncc(CSc2nc(N)nc3[nH]nnc23)c1C(F)(F)F] | 7-(((1-methyl-5-(trifluoromethyl)-1H-pyrazol-4-yl)methyl)thio)-3H-[1,2,3]triazolo[4,5-d]pyrimidin-5-amine | MS(ESI) 331.1 (M + H)$^+$. $^1$H NMR (500 MHz, DMSO-$d_6$) δ 8.15 (s, 1H), 4.63-4.38 (m, 2H), 4.01-3.83 (m, 3H) |
| 164 | 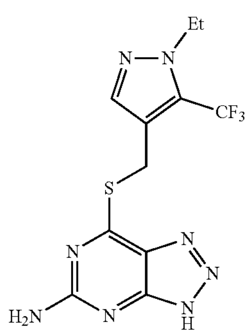 [SMILES: CCn1ncc(CSc2nc(N)nc3[nH]nnc23)c1C(F)(F)F] | 7-(((1-ethyl-5-(trifluoromethyl)-1H-pyrazol-4-yl)methyl)thio)-3H-[1,2,3]triazolo[4,5-d]pyrimidin-5-amine | MS(ESI) 345.1 (M + H)$^+$. $^1$H NMR (500 MHz, DMSO-$d_6$) δ 7.15 (br. s., 2H), 6.92 (s, 1H), 4.58 (s, 2H), 4.21 (q, J = 7.0 Hz, 2H), 1.36 (t, J = 7.2 Hz, 3H) |
| 165 | 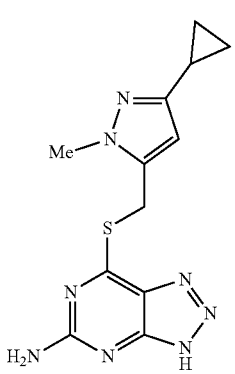 [SMILES: Cn1nc(C2CC2)cc1CSc1nc(N)nc2[nH]nnc12] | 7-(((3-cyclopropyl-1-methyl-1H-pyrazol-5-yl)methyl)thio)-3H-[1,2,3]triazolo[4,5-d]pyrimidin-5-amine | MS(ESI) 303.1 (M + H)$^+$. $^1$H NMR (500 MHz, DMSO-$d_6$) δ 7.19 (br. s., 1H), 6.14 (s, 1H), 4.68 (s, 3H), 3.80 (s, 2H), 1.82 (br. s., 1H), 0.87 (d, J = 7.9 Hz, 2H), 0.61 (d, J = 2.1 Hz, 2H) |

| Ex. No. | Structure | Name | Analytical Data |
|---|---|---|---|
| 166 | 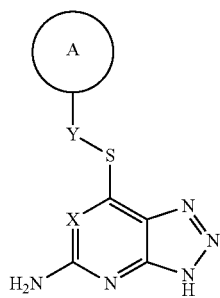 | 7-((2-(pyrrolidin-1-ylmethyl)benzyl)thio)-3H-[1,2,3]triazolo[4,5-d]pyrimidin-5-amine | MS(ESI) 342.2 (M + H)$^+$. |

What is claimed is:

1. A compound according to the formula (I)

$$\text{(I)}$$

or a stereoisomer, a tautomer, a pharmaceutically acceptable salt, a polymorph, or a solvate thereof, wherein:

ring A is independently phenyl substituted with 0-1 $R^2$ and 0-4 $R^3$, or a 5- to 6-membered heteroaryl comprising carbon atoms and 1-4 heteroatoms selected from N, $NR^a$, O, and $S(O)_p$, wherein said heteroaryl is substituted with 0-1 $R^2$ and 0-3 $R^3$;

X is independently CH or N;

Y is independently selected from: a hydrocarbon linker substituted with 0-1 $R^1$, or a hydrocarbon-heteroatom linker substituted with 0-1 $R^1$; wherein said hydrocarbon linker has one to six carbon atoms and may be straight or branched; and said hydrocarbon-heteroatom linker has one to four carbon atoms and one heteroatom selected from the group consisting of from O, S, NH, $N(C_{1-4}$ alkyl), CONH, and NHCO;

$R^1$ is independently selected from: CN, OH, —$C_{1-4}$ alkyl substituted with 0-1 $R^{18}$ $C_{1-4}$ haloalkyl, Ph, Bn, COPh, CH(OH)Ph, $CO_2(C_{1-4}$ alkyl), and CONHBn;

$R^2$ is independently selected from: —$CH(NH_2)CF_3$, —$(CH_2)_tOH$, —$O(CH_2)_{2-3}N(C_{1-4}$ alkyl)$_2$, —$(CH_2)_nR^4$, and —$(CH_2)_n(X_1)_n(CH_2)_nR^5$;

$X_1$ is independently selected from: $C(Me)_2$, O, S, CO and $SO_2$;

$R^3$ is, at each occurrence, independently selected from: halogen, CN, $C_{1-4}$ alkyl, $C_{1-4}$ alkoxy, $C_{1-4}$ haloalkyl, $C_{1-4}$ haloalkoxy, $NO_2$, $CONH_2$, and $SO_2(C_{1-4}$ alkyl);

alternatively, $R^2$ and $R^3$, together with the carbon atoms to which they are attached, combine to form a 5- to 6-membered carbocyclic or heterocyclic ring comprising carbon atoms and 0-3 heteroatoms selected from N, $NR^a$, O, and $S(O)_p$; wherein said heterocycle is substituted with 0-2 $R^{19}$;

$R^4$ is independently selected from: halogen, $C_{1-4}$ alkyl, $C_{1-4}$ alkoxy, $C_{1-4}$ alkylthio, $C_{1-4}$ haloalkyl, $C_{1-4}$ haloalkoxy, $C_{1-4}$ haloalkylthio, CN, $CO_2(C_{1-4}$ alkyl), $NO_2$, $NR^6R^7$, $CONR^6R^7$, $COR^{10}$, —$CONH(CH_2)_{1-2}NR^9R^{10}$, $SO_2NR^9R^{10}$, and $S(O)_pR^8$;

$R^5$ is independently selected from: $C_{3-10}$ carbocycle substituted with 0-2 $R^{11}$, phenyl substituted with 0-3 $R^{11}$ and 0-1 $R^{12}$, and 5- to 10-membered heterocycle comprising carbon atoms and 1-4 heteroatoms selected from N, $NR^a$, O, and $S(O)_p$; wherein said heterocycle is substituted with 0-2 $R^{11}$ and 0-1 $R^{13}$;

$R^6$ is, at each occurrence, independently selected from: H, $C_{1-4}$ haloalkyl, a $C_{1-6}$ alkyl substituted with 0-2 $R^{15}$, $(CH_2)_n$—$C_{3-6}$ cycloalkyl substituted with 0-1 $R^{14}$, $(CH_2)_n$-phenyl substituted with 0-1 $R^{16}$, —$(CH_2)_n$-5- to 10-membered heterocycle comprising carbon atoms and 1-4 heteroatoms selected from N, $NR^a$, O, and $S(O)_p$, wherein said heterocycle is substituted with 0-1 $R^{17}$;

$R^7$ is, at each occurrence, independently selected from: H and $C_{1-4}$ alkyl substituted with $R^{11}$;

alternatively, $R^6$ and $R^7$, together with the nitrogen atom to which they are attached, combine to form a 4- to 10-membered heterocyclic ring comprising carbon atoms and 1-4 heteroatoms selected from N, $NR^a$, O, and $S(O)_p$; wherein said heterocycle is substituted with 0-1 $R^{17}$;

$R^8$ is, at each occurrence, independently selected from: $C_{1-4}$ alkyl, —$(CH_2)_r$—$C_{3-6}$ cycloalkyl, and —$(CH_2)_r$-phenyl;

$R^9$ is, at each occurrence, independently selected from: H and $C_{1-4}$ alkyl;

$R^{10}$ is, at each occurrence, independently selected from: $R^8$ and H;

$R^{11}$ is, at each occurrence, independently selected from: OH, halogen, $C_{1-4}$ alkoxy, $C_{1-4}$ haloalkyl, and $C_{1-4}$ haloalkoxy;

$R^{12}$ is independently selected from: halogen, CN, $C_{1-4}$ alkyl, $C_{1-4}$ alkoxy, $C_{1-4}$ haloalkyl, $C_{1-4}$ haloalkoxy, $C_{1-4}$ alkylthio, OH, $CH_2OH$, $CO_2H$, $CO_2(C_{1-4}$ alkyl), $NH_2$, $CH_2NH_2$, $N(C_{1-4}$ alkyl)$_2$, $CH_2N(C_{1-4}$ alkyl)$_2$, $CONH_2$, $CONH(C_{1-4}$ alkyl), $CONHCH_2CH_2(C_{1-4}$ alkyl)$_2$, $CON(C_{1-4}$ alkyl)$_2$, $SO_2NH_2$, $SO_2NH(C_{1-4}$ alkyl), $SO_2N(C_{1-4}$ alkyl)$_2$, CONHPh, NHCOPh, $(CH_2)_n$—$C_{3-6}$ carbocycle substituted with 0-2 $R^c$, and a 5- to 6-membered heterocycle comprising carbon atoms and 1-4 heteroatoms selected from N, $NR^a$, O, and $S(O)_p$, wherein said heterocycle is substituted with 0-2 $R^c$;

$R^{13}$ is independently selected from: $R^{12}$ and =O;

$R^{14}$ and $R^{16}$ are, at each occurrence, independently selected from: halogen, $C_{1-4}$ alkyl, $C_{1-4}$ alkoxy, $C_{1-4}$ haloalkyl, $C_{1-4}$ haloalkoxy, OH, $CH_2OH$, $N(C_{1-4}$ alkyl$)_2$, $CONH_2$, $CONH(C_{1-4}$ alkyl), $CON(C_{1-4}$ alkyl$)_2$, $OCH_2CONH_2$, $NHCO(C_{1-4}$ alkyl), $NHCO_2(C_{1-4}$ alkyl), $SO_2(C_{1-4}$ alkyl), —$(CH_2)_n$-phenyl, —O—$(CH_2)_n$-phenyl, and pyridylmethyl;

$R^{15}$ is, at each occurrence, independently selected from: OH, $C_{1-4}$ alkoxy, $C_{1-4}$ haloalkyl, $C_{1-4}$ haloalkoxy, $N(C_{1-4}$ alkyl$)_2$, $CONH_2$, $CONH(C_{1-4}$ alkyl), and $CON(C_{1-4}$ alkyl$)_2$;

$R^{17}$ is independently selected from: $R^{14}$ and =O;

$R^{18}$ is independently selected from: OH, CN, $NH_2$, $N(C_{1-4}$ alkyl$)_2$, NHBn, imidazolyl and morpholinyl;

$R^{19}$ is independently selected from: halogen and $CO_2(C_{1-4}$ alkyl);

$R^a$ is, at each occurrence, independently selected from: H, $C_{1-4}$ alkyl, $CO(C_{1-4}$ alkyl), $CO_2(C_{1-4}$ alkyl), $SO_2(C_{1-4}$ alkyl), —$(CH_2)_n$—$C_{3-6}$ cycloalkyl, $(CH_2)_n$-phenyl substituted with 0-2$R^c$, —CO(—$(CH_2)_n$-phenyl), a 5- to 6-membered heteroaryl comprising carbon atoms and 1-4 heteroatoms selected from N, $NR^b$, O, and $S(O)_p$, wherein said heteroaryl is substituted with 0-2 $R^c$;

$R^b$ is, at each occurrence, independently selected from: H and $C_{1-4}$ alkyl;

$R^c$ is, at each occurrence, independently selected from: OH, CN, $C_{1-4}$ alkyl, halogen, $C_{1-4}$ alkoxy, $C_{1-4}$ haloalkyl, $C_{1-4}$ haloalkoxy, $N(C_{1-4}$ alkyl$)_2$, —$CH_2N(C_{1-4}$ alkyl$)_2$, $CONHCH_2CH_2N(C_{1-4}$ alkyl$)_2$, pyrrolidinyl, piperazinyl, and

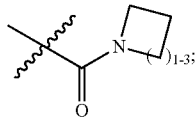

n is, at each occurrence, independently selected from: 0, 1 and 2;

p is, at each occurrence, independently selected from: 0, 1 and 2; and t is, at each occurrence, independently selected from: 1 and 2;

provided that

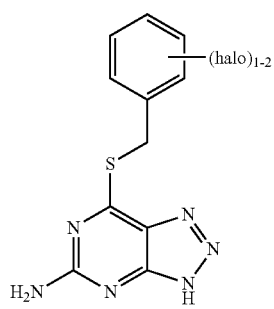

is excluded.

2. The compound according to claim 1 or a stereoisomer, a tautomer, a pharmaceutically acceptable salt, a polymorph, or a solvate thereof, wherein: X is CH.

3. The compound according to claim 2 or a stereoisomer, a tautomer, a pharmaceutically acceptable salt, a polymorph, or a solvate thereof, wherein: ring A is independently phenyl substituted with 0-1 $R^2$ and 0-3 $R^3$, or a heteroaryl substituted with 0-1 $R^2$ and 0-2 $R^3$ selected from: oxazolyl, isoxazolyl, thiazolyl, pyrazolyl, 1-$R^a$-pyrazolyl, imidazolyl 1-$R^a$-imidazolyl, triazolyl, 1-$R^a$-triazolyl, pyridyl, and pyrimidinyl; and alternatively, $R^2$ and $R^3$, together with the carbon atoms to which they are attached, combine to form a 5- to 6-membered carbocyclic or heterocyclic ring comprising carbon atoms and 0-3 heteroatoms selected from N, $NR^a$, O, and $S(O)_p$; wherein said heterocycle is substituted with 0-2 $R^{19}$.

4. The compound according to claim 1, or a stereoisomer, a tautomer, or a pharmaceutically acceptable salt thereof, wherein the compound is selected from 7-(Benzylthio)-3H-[1,2,3]triazolo[4,5-b]pyridin-5-amine, 7-((1-phenylethyl)thio)-3H-[1,2,3]triazolo[4,5-b]pyridin-5-amine, 7-((2-fluorobenzyl) thio)-3H-[1,2,3]triazolo [4,5-b]pyridin-5-amine, 7-((2-chlorobenzyl) thio)-3H-[1,2,3]triazolo [4,5-b]pyridin-5-amine, 7-((2-(trifluoromethyl) benzyl)thio)-3H-[1,2,3] triazolo [4,5-b]pyridin-5-amine, 7-((3-fluorobenzyl) thio)-3H-[1,2,3]triazolo [4,5-b]pyridin-5-amine, 7-((4-(trifluoromethoxy) benzyl)thio)-3H-[1,2,3] triazolo [4,5-b]pyridin-5-amine, 7-((4-chlorobenzyl) thio)-3H-[1,2,3]triazolo [4,5-b]pyridin-5-amine, 7-((4-methoxybenzyl) thio)-3H-[1,2,3]triazolo [4,5-b] pyridin-5-amine, 7-((2,6-Difluorobenzyl)thio)-3H-[1,2,3]triazolo[4,5-b] pyridin-5-amine, 7-((2,6-Dichlorobenzyl)thio)-3H-[1,2,3]triazolo[4,5-b] pyridin-5-amine, 2-(((5-Amino-3H-[1,2,3]triazolo[4,5-b]pyridin-7-yl)thio) methyl)-4-(1H-pyrazol-1-yl)benzonitrile, 7-((4-(Benzylamino)-1-phenylbutyl)thio)-3H-[1,2,3]triazolo[4,5-b]pyridin-5-amine, 7-((3-(Pyrrolidin-1-ylmethyl)benzyl)thio)-3H-[1,2,3]triazolo[4,5-b]pyridin-5-amine, 7-(((3-Cyclopropyl-4-fluoro-1-methyl-1H-pyrazol-5-yl) methyl)thio)-3H-[1,2,3]triazolo[4,5-b]pyridin-5-amine, 7-(((4-Fluoro-1-methyl-3-phenyl-1H-pyrazol-5-yl) methyl)thio)-3H-[1,2,3]triazolo[4,5-b]pyridin-5-amine, 7-((4-chloro-2-(methylsulfonyl)benzyl) thio)-3H-[1,2,3] triazolo[4,5-b]pyridin-5-amine, 7-((2,5-difluorobenzyl)thio)-3H-[1,2,3]triazolo[4,5-b] pyridin-5-amine, 2-(((5-amino-3H-[1,2,3] triazolo[4,5-b]pyridin-7-yl)thio) methyl)-4-fluorobenzonitrile, 2-(((5-amino-3H-[1,2,3] triazolo[4,5-b]pyridin-7-yl)thio) methyl)-5-bromobenzonitrile, 7-(((5-methyl-2-(p-tolyl) thiazol-4-yl)methyl)thio)-3H-[1,2,3]triazolo[4,5-b]pyridin-5-amine, 7-((4-chloro-2,6-difluorobenzyl)thio)-3H-[1,2,3]triazolo [4,5-b]pyridin-5-amine, 7-(((2,6-dichloro-5-methylpyridin-3-yl)methyl) thio)-3H-[1,2,3]triazolo[4,5-b]pyridin-5-amine, (6-(((5-amino-3H-[1,2,3] triazolo[4,5-b]pyridin-7-yl) thio)methyl)pyridin-2-yl) methanol, methyl 3-(((5-amino-3H-[1,2,3]triazolo[4,5-b]pyridin-7-yl)thio)methyl)picolinate,
7-(((6-aminopyridin-2-yl) methyl)thio)-3H-[1,2,3] triazolo[4,5-b]pyridin-5-amine,
7-((2,5-difluoro-4-(1,2,4-oxadiazol-3-yl)benzyl)thio)-3H-[1,2,3]triazolo[4,5-b]pyridin-5-amine,
7-((2-(trifluoromethoxy) benzyl)thio)-3H-[1,2,3] triazolo[4,5-b]pyridin-5-amine,
7-((1-(2-(trifluoromethyl) phenyl)ethyl)thio)-3H-[1,2,3] triazolo[4,5-b]pyridin-5-amine,
methyl 2-(((5-amino-3H-[1,2,3]triazolo[4,5-b]pyridin-7-yl)thio)methyl)quinoline-6-carboxylate,
7-(((1-benzyl-1H-pyrazol-4-yl)methyl)thio)-3H-[1,2,3] triazolo[4,5-b]pyridin-5-amine,
7-(((1-methyl-3-phenyl-1H-pyrazol-5-yl)methyl)thio)-3H-[1,2,3]triazolo[4,5-b]pyridin-5-amine,
7-(((1-phenyl-1H-1,2,3-triazol-4-yl)methyl)thio)-3H-[1,2,3]triazolo[4,5-b]pyridin-5-amine,
7-((2-((phenylsulfonyl) methyl)benzyl)thio)-3H-[1,2,3] triazolo[4,5-b]pyridin-5-amine,
7-(((1-ethyl-3-(trifluoromethyl)-1H-pyrazol-5-yl)methyl)thio)-3H-[1,2,3]triazolo[4,5-b]pyridin-5-amine,
7-(((5-methyl-2-(2,4,6-trifluorophenyl)oxazol-4-yl)methyl)thio)-3H-[1,2,3] triazolo[4,5-b]pyridin-5-amine,
7-((2,2,2-trifluoro-1-phenylethyl)thio)-3H-[1,2,3] triazolo[4,5-b]pyridin-5-amine,
7-((2,5-bis(trifluoromethyl) benzyl)thio)-3H-[1,2,3] triazolo[4,5-b]pyridin-5-amine,
2-((5-amino-3H-[1,2,3] triazolo[4,5-b]pyridin-7-yl)thio)-1,2-diphenylethanone,
7-((2-(1H-pyrazol-1-yl) benzyl)thio)-3H-[1,2,3] triazolo[4,5-b]pyridin-5-amine,
7-((4-bromo-2-fluoro-6-(methylsulfonyl)benzyl) thio)-3H-[1,2,3]triazolo[4,5-b]pyridin-5-amine,
7-((3-bromo-2,6-difluorobenzyl)thio)-3H-[1,2,3]triazolo[4,5-b]pyridin-5-amine,
7-((3-(dimethylamino)-1-phenylpropyl)thio)-3H-[1,2,3] triazolo[4,5-b]pyridin-5-amine,
7-((1-phenylpropyl)thio)-3H-[1,2,3]triazolo[4,5-b]pyridin-5-amine,
2-((5-amino-3H-[1,2,3] triazolo[4,5-b]pyridin-7-yl)thio)-1,2-diphenylethanol,
4-(((5-amino-3H-[1,2,3] triazolo[4,5-b]pyridin-7-yl)thio)methyl)-3-fluorobenzonitrile,
7-(((2,4-dichloropyridin-3-yl)methyl)thio)-3H-[1,2,3] triazolo[4,5-b]pyridin-5-amine,
7-((2-fluoro-5-(trifluoromethoxy)benzyl) thio)-3H-[1,2,3] triazolo[4,5-b]pyridin-5-amine,
methyl 2-((5-amino-3H-[1,2,3]triazolo[4,5-b]pyridin-7-yl)thio)-2-(2-chlorophenyl)acetate,
7-(((1-methyl-1H-indazol-4-yl)methyl)thio)-3H-[1,2,3] triazolo[4,5-b]pyridin-5-amine,
methyl 3-(((5-amino-3H-[1,2,3]triazolo[4,5-b]pyridin-7-yl)thio)methyl)-4-fluorobenzoate,
7-((5-fluoro-2-(methylsulfonyl)benzyl) thio)-3H-[1,2,3] triazolo[4,5-b]pyridin-5-amine,
7-((1-(2-(methylsulfonyl) phenyl)ethyl)thio)-3H-[1,2,3] triazolo[4,5-b]pyridin-5-amine,
3-(((5-amino-3H-[1,2,3] triazolo[4,5-b]pyridin-7-yl)thio) methyl)-4-fluoro-N-(1-methylcyclopropyl) benzamide,
2-(((5-amino-3H-[1,2,3]triazolo[4,5-b]pyridin-7-yl)thio) methyl)-5-fluorobenzonitrile,
7-((pyrimidin-2-ylmethyl) thio)-3H-[1,2,3]triazolo[4,5-b]pyridin-5-amine,
7-(((1,3-dimethyl-1H-pyrazol-5-yl)methyl)thio)-3H-[1,2,3]triazolo[4,5-b] pyridin-5-amine,
7-(((1,3,5-trimethyl-1H-pyrazol-4-yl)methyl)thio)-3H-[1,2,3]triazolo[4,5-b] pyridin-5-amine,
7-(((5-chloro-1,3-dimethyl-1H-pyrazol-4-yl)methyl)thio)-3H-[1,2,3]triazolo[4,5-b]pyridin-5-amine,
7-((2-(benzylsulfonyl)-5-chlorobenzyl)thio)-3H-[1,2,3] triazolo[4,5-b]pyridin-5-amine,
7-(((1-benzyl-1H-indazol-3-yl)methyl)thio)-3H-[1,2,3] triazolo[4,5-b]pyridin-5-amine,
7-(((5-ethyl-2-phenyl-2H-1,2,3-triazol-4-yl)methyl)thio)-3H-[1,2,3]triazolo[4,5-b]pyridin-5-amine,
2-(((5-amino-3H-[1,2,3] triazolo[4,5-b]pyridin-7-yl)thio) methyl)-3-chlorobenzenesulfonamide,
7-(((5-methyl-2-phenyl-2H-1,2,3-triazol-4-yl)methyl)thio)-3H-[1,2,3]triazolo[4,5-b]pyridin-5-amine,
7-((5-fluoro-2-(trifluoromethoxy)benzyl) thio)-3H-[1,2,3] triazolo[4,5-b]pyridin-5-amine,
7-(((2-(3-fluorophenyl)-5-methyl-2H-1,2,3-triazol-4-yl) methyl)thio)-3H-[1,2,3] triazolo[4,5-b]pyridin-5-amine,
2-(((5-amino-3H-[1,2,3] triazolo[4,5-b]pyridin-7-yl)thio) methyl)-3-fluorobenzonitrile,
7-(((2-(3-methoxyphenyl)-5-methyl-2H-1,2,3-triazol-4-yl)methyl)thio)-3H-[1,2,3] triazolo[4,5-b]pyridin-5-amine,
ethyl 5-(((5-amino-3H-[1,2,3]triazolo[4,5-b]pyridin-7-yl)thio)methyl)-1-methyl-1H-pyrazole-3-carboxylate,
7-(((5-chloro-1-methyl-3-phenyl-1H-pyrazol-4-yl)methyl)thio)-3H-[1,2,3] triazolo[4,5-b]pyridin-5-amine,
7-(((1-(4-fluorophenyl)-3,5-dimethyl-1H-pyrazol-4-yl) methyl)thio)-3H-[1,2,3] triazolo[4,5-b]pyridin-5-amine,
2-(((5-amino-3H-[1,2,3] triazolo[4,5-b]pyridin-7-yl)thio) methyl)-4-chlorobenzonitrile,
2-(((5-amino-3H-[1,2,3] triazolo[4,5-b]pyridin-7-yl)thio) methyl)-5-chlorobenzonitrile,
2-(((5-amino-3H-[1,2,3] triazolo[4,5-b]pyridin-7-yl)thio) methyl)-6-chlorobenzonitrile,
7-(((1-benzyl-5-chloro-3-methyl-1H-pyrazol-4-yl) methyl)thio)-3H-[1,2,3] triazolo[4,5-b]pyridin-5-amine,
7-(((1,4-dimethyl-1H-imidazol-5-yl)methyl)thio)-3H-[1,2,3]triazolo[4,5-b] pyridin-5-amine,
7-(((5-chloro-1-methyl-3-(trifluoromethyl)-1H-pyrazol-4-yl)methyl)thio)-3H-[1,2,3]triazolo[4,5-b] pyridin-5-amine,
7-(((5-chloro-3-methyl-1-phenyl-1H-pyrazol-4-yl) methyl)thio)-3H-[1,2,3] triazolo[4,5-b]pyridin-5-amine,
7-(((1-(cyclopropylmethyl)-3,5-dimethyl-1H-pyrazol-4-yl)methyl)thio)-3H-[1,2,3] triazolo[4,5-b]pyridin-5-amine,
7-(((1-cyclopropyl-3,5-dimethyl-1H-pyrazol-4-yl) methyl)thio)-3H-[1,2,3] triazolo[4,5-b]pyridin-5-amine,
7-(((1-cyclobutyl-3,5-dimethyl-1H-pyrazol-4-yl)methyl)thio)-3H-[1,2,3] triazolo[4,5-b]pyridin-5-amine,
7-(((5-fluoro-1-methyl-3-(trifluoromethyl)-1H-pyrazol-4-yl)methyl)thio)-3H-[1,2,3]triazolo[4,5-b] pyridin-5-amine,
7-(((1-methyl-3-(trifluoromethyl)-1H-pyrazol-4-yl) methyl)thio)-3H-[1,2,3]triazolo[4,5-b] pyridin-5-amine,
7-(((5-chloro-3-ethyl-1-methyl-1H-pyrazol-4-yl)methyl) thio)-3H-[1,2,3] triazolo[4,5-b]pyridin-5-amine, 7-(((1-methyl-5-(trifluoromethyl)-1H-pyrazol-4-yl) methyl)thio)-3H-[1,2,3]triazolo[4,5-b]pyridin-5-amine, 2-(((5-amino-3H-[1,2,3] triazolo[4,5-b]pyridin-7-yl)thio) methyl)-4-cyclopropylbenzonitrile, 3-(((5-amino-3H-[1,2,3] triazolo[4,5-b]pyridin-7-yl)thio) methyl)-4-cyclopropylbenzonitrile, 2-(((5-amino-3H-[1,2,3] triazolo[4,5-b]pyridin-7-yl)thio) methyl)-3-cyclopropylbenzonitrile, 2-(((5-amino-3H-[1,2,3] triazolo[4,5-b]pyridin-7-yl)thio) methyl)-3-bromobenzonitrile, 3-(((5-amino-3H-[1,2,3] triazolo[4,5-b]pyridin-7-yl)thio) methyl)benzonitrile, 7-((2-(pyridin-2-yl)benzyl) thio)-3H-[1,2,3]triazolo[4,5-b]pyridin-5-amine, 7-((3-((dimethylamino) methyl)benzyl)thio)-3H-[1,2,3] triazolo[4,5-b]pyridin-5-amine, 7-((2-(morpholinomethyl) benzyl)thio)-3H-[1,2,3] triazolo[4,5-b]pyridin-5-amine, 7-((2-(azetidin-1-ylmethyl) benzyl)thio)-3H-[1,2,3] triazolo[4,5-b]pyridin-5-amine, 7-((2-((dimethylamino) methyl)benzyl)thio)-3H-[1,2,3] triazolo[4,5-b]pyridin-5-amine, 7-((2-(piperidin-1-ylmethyl) benzyl)thio)-3H-[1,2,3] triazolo[4,5-b]pyridin-5-amine, 7-((2-((3-phenoxypyrrolidin-1-yl)methyl)benzyl)thio)-3H-[1,2,3]triazolo[4,5-b] pyridin-5-amine, 7-((5-((dimethylamino) methyl)-2-fluorobenzyl) thio)-3H-[1,2,3]triazolo[4,5-b]pyridin-5-amine, 7-(((3-cyclopropyl-1-methyl-1H-pyrazol-5-yl)methyl) thio)-3H-[1,2,3]triazolo[4,5-b]pyridin-5-amine, 7-(((5-phenylisoxazol-3-yl)methyl)thio)-3H-[1,2,3] triazolo[4,5-b]pyridin-5-amine, 7-((2-chloro-6-(methylsulfonyl)benzyl) thio)-3H-[1,2,3] triazolo[4,5-b]pyridin-5-amine, 7-(((1-methyl-5-phenyl-1H-pyrazol-3-yl)methyl)thio)-3H-[1,2,3]triazolo[4,5-b] pyridin-5-amine, 7-((2-chloro-4-(methylsulfonyl)benzyl) thio)-3H-[1,2,3] triazolo[4,5-b]pyridin-5-amine, 7-(((2,2-difluorobenzo[d] [1,3]dioxol-4-yl)methyl) thio)-3H-[1,2,3]triazolo[4,5-b]pyridin-5-amine, ethyl 2-((5-amino-3H-[1,2,3] triazolo[4,5-b]pyridin-7-yl) thio)-2-phenylacetate, 7-((1-(pyridin-3-yl)ethyl) thio)-3H-[1,2,3]triazolo[4,5-b] pyridin-5-amine, 3-(((5-amino-3H-[1,2,3] triazolo[4,5-b]pyridin-7-yl) thio) methyl)picolinonitrile, 2-(((5-amino-3H-[1,2,3] triazolo[4,5-b]pyridin-7-yl thio) methyl)-4-(difluoromethoxy) benzonitrile, 2-(((5-amino-3H-[1,2,3] triazolo[4,5-b]pyridin-7-yl)thio) methyl)-4-cyclopropoxybenzonitrile, 7-(((4-chloro-3-cyclopropyl-1-methyl-1H-pyrazol-5-yl) methyl)thio)-3H-[1,2,3] triazolo[4,5-b]pyridin-5-amine, 7-(((4-chloro-1-methyl-3-phenyl-1H-pyrazol-5-yl) methyl)thio)-3H-[1,2,3] triazolo[4,5-b]pyridin-5-amine, 7-(((1-phenyl-3-(trifluoromethyl)-1H-pyrazol-4-yl) methyl)thio)-3H-[1,2,3]triazolo[4,5-b] pyridin-5-amine, 7-(((1-phenyl-5-(trifluoromethyl)-1H-pyrazol-4-yl) methyl)thio)-3H-[1,2,3]triazolo[4,5-b] pyridin-5-amine, 7-(((1-cyclohexyl-3-(trifluoromethyl)-1H-pyrazol-4-yl) methyl)thio)-3H-[1,2,3]triazolo[4,5-b] pyridin-5-amine, 7-(((1-cyclohexyl-5-(trifluoromethyl)-1H-pyrazol-4-yl) methyl)thio)-3H-[1,2,3]triazolo[4,5-b] pyridin-5-amine, 2-(((5-amino-3H-[1,2,3] triazolo[4,5-b]pyridin-7-yl)thio) methyl)-3-chlorobenzonitrile, 3-(((5-amino-3H-[1,2,3] triazolo[4,5-b]pyridin-7-yl)thio) methyl)-2,5-dichlorobenzenesulfonamide, 4-(((5-amino-3H-[1,2,3] triazolo[4,5-b]pyridin-7-yl)thio) methyl)-3-chlorobenzenesulfonamide, 4-(((5-amino-3H-[1,2,3] triazolo[4,5-b]pyridin-7-yl)thio) methyl)-3-fluorobenzamide, 2-(((5-amino-3H-[1,2,3] triazolo[4,5-b]pyridin-7-yl)thio) methyl)-6-fluorobenzonitrile, 3-(((5-amino-3H-[1,2,3] triazolo[4,5-b]pyridin-7-yl)thio) methyl)-4-chlorobenzonitrile, 3-(((5-amino-3H-[1,2,3] triazolo[4,5-b]pyridin-7-yl)thio) methyl)-4-fluorobenzonitrile, 4-(((5-amino-3H-[1,2,3] triazolo[4,5-b]pyridin-7-yl)thio) methyl)-3-chlorobenzonitrile, 7-((quinolin-8-ylmethyl)thio)-3H-[1,2,3] triazolo[4,5-b] pyridin-5-amine, 2-((5-Amino-3H-[1,2,3]triazolo[4,5-b]pyridin-7-yl)thio)-2-phenylethanol, 2-((5-Amino-3H-[1,2,3]triazolo[4,5-b]pyridin-7-yl)thio)-N-benzyl-2-phenylacetamide, 7-((2-(Benzylamino)-1-phenylethyl)thio)-3H-[1,2,3]triazolo[4,5-b]pyridin-5-amine, 2-(((5-Amino-3H-[1,2,3]triazolo[4,5-b]pyridin-7-yl)thio) methyl)-3-(1H-pyrazol-1-yl)benzonitrile, 3-(((5-Amino-3H-[1,2,3]triazolo[4,5-b]pyridin-7-yl)thio) methyl)-4-(pyridin-4-yl)benzonitrile, 2-(((5-amino-3H-[1,2,3] triazolo[4,5-b]pyridin-7-yl)thio) methyl)-3-(1H-imidazol-1-yl)benzonitrile, 3-(((5-amino-3H-[1,2,3]triazolo[4,5-b] pyridin-7-yl)thio) methyl)-4-(1H-pyrazol-1-yl) benzonitrile, 4-(((5-amino-3H-[1,2,3]triazolo[4,5-b] pyridin-7-yl)thio) methyl)-3-cyclopropylbenzonitrile, 7-(((3-Cyclopropyl-1-phenyl-1H-pyrazol-4-yl)methyl) thio)-3H-[1,2,3]triazolo[4,5-b]pyridin-5-amine, 7-(((1-(pyridin-2-yl)-3-(trifluoromethyl)-1H-pyrazol-4-yl)methyl) thio)-3H-[1,2,3] triazolo[4,5-b]pyridin-5-amine, 7-(((1-(pyridin-3-yl)-3-(trifluoromethyl)-1H-pyrazol-4-yl)methyl) thio)-3H-[1,2,3] triazolo [4,5-b]pyridin-5-amine, 7-(((1-(pyridin-4-yl)-3-(trifluoromethyl)-1H-pyrazol-4-yl)methyl) thio)-3H-[1,2,3]triazolo [4,5-b]pyridin-5-amine, 7-(((3-(difluoromethyl)-1-phenyl-1H-pyrazol-4-yl) methyl)thio)-3H-[1,2,3]triazolo[4,5-b]pyridin-5-amine, 7-(((1-(6-(pyrrolidin-1-yl)pyridin-3-yl)-3-(trifluoromethyl)-1H-pyrazol-4-yl)methyl) thio)-3H-[1,2,3]triazolo [4,5-b]pyridin-5-amine, 7-(((1-(6-(dimethylamino) pyridin-2-yl)-3-(trifluoromethyl)-1H-pyrazol-4-yl)methyl) thio)-3H-[1,2,3]triazolo [4,5-b]pyridin-5-amine, 7-(((1-(2-(dimethylamino) pyridin-4-yl)-3-(trifluoromethyl)-1H-pyrazol-4-yl)methyl) thio)-3H-[1,2,3]triazolo [4,5-b]pyridin-5-amine, 7-(((3-(difluoromethyl)-1-(pyridin-4-yl)-1H-pyrazol-4-yl)methyl) thio)-3H-[1,2,3]triazolo [4,5-b]pyridin-5-amine, 7-(((3-(difluoromethyl)-1-(pyridazin-4-yl)-1H-pyrazol-4-yl)methyl) thio)-3H-[1,2,3]triazolo [4,5-b]pyridin-5-amine, 7-(((3-(difluoromethyl)-1-(pyridazin-3-yl)-1H-pyrazol-4-yl)methyl) thio)-3H-[1,2,3]triazolo [4,5-b]pyridin-5-amine, 7-(((3-(difluoromethyl)-1-(pyrazin-2-yl)-1H-pyrazol-4-yl)methyl) thio)-3H-[1,2,3]triazolo [4,5-b]pyridin-5-amine, (5-(4-(((5-amino-3H-[1,2,3]triazolo[4,5-b] pyridin-7-yl) thio) methyl)-3-(difluoromethyl)-1H-pyrazol-1-yl) pyrazin-2-yl)(azetidin-1-yl)methanone, 3-(((5-amino-3H-[1,2,3]triazolo[4,5-b] pyridin-7-yl)thio) methyl)-1-phenyl-1H-pyrazole-4-carbonitrile, 7-(((3-(difluoromethyl)-1-(3-((dimethylamino) methyl) phenyl)-1H-pyrazol-4-yl)methyl) thio)-3H-[1,2,3]triazolo [4,5-b]pyridin-5-amine, 3-(4-(((5-amino-3H-[1,2,3]triazolo[4,5-b] pyridin-7-yl) thio) methyl)-3-(difluoromethyl)-1H-pyrazol-1-yl)-N-(2-(dimethylamino)ethyl) benzamide, 7-(((3-(difluoromethyl)-1-(2-((dimethylamino) methyl) phenyl)-1H-pyrazol-4-yl)methyl) thio)-3H-[1,2,3]triazolo [4,5-b]pyridin-5-amine, 2-(4-(((5-amino-3H-[1,2,3]triazolo[4,5-b] pyridin-7-yl) thio) methyl)-3-(difluoromethyl)-1H-pyrazol-1-yl)-N-(2-(dimethylamino)ethyl) benzamide, 7-(((3-(difluoromethyl)-1-(pyrazin-2-yl)-1H-pyrazol-4-yl)methyl) thio)-3H-[1,2,3]triazolo [4,5-b]pyridin-5-amine, 7-(((5-(difluoromethyl)-2-phenyl-2H-1,2,3-triazol-4-yl) methyl) thio)-3H-[1,2,3]triazolo [4,5-b]pyridin-5-amine, 2-(((5-Amino-3H-[1,2,3]triazolo[4,5-d]pyrimidin-7-yl) thio)methyl)-3-fluorobenzonitrile, 7-(benzylthio)-3H-[1,2,3] triazolo[4,5-d]pyrimidin-5-amine, 7-(((5-chloro-3-methyl-1-phenyl-1H-pyrazol-4-yl) methyl)thio)-3H-[1,2,3] triazolo[4,5-d]pyrimidin-5-amine, 2-(((5-amino-3H-[1,2,3] triazolo[4,5-d]pyrimidin-7-yl) thio)methyl)-4-fluorobenzonitrile, 7-((2-(1H-pyrazol-1-yl) benzyl)thio)-3H-[1,2,3] triazolo [4,5-d]pyrimidin-5-amine, 7-(((1-benzyl-5-chloro-3-methyl-1H-pyrazol-4-yl) methyl)thio)-3H-[1,2,3] triazolo[4,5-d]pyrimidin-5-amine, 7-(((5-fluoro-1-methyl-3-(trifluoromethyl)-1H-pyrazol-4-yl)methyl)thio)-3H-[1,2,3]triazolo[4,5-d]pyrimidin-5-amine, 3-(((5-amino-3H-[1,2,3] triazolo[4,5-d]pyrimidin-7-yl) thio)methyl)-4-cyclopropylbenzonitrile, 7-(((1-methyl-1H-indazol-4-yl)methyl)thio)-3H-[1,2,3] triazolo[4,5-d] pyrimidin-5-amine, 7-(((1-methyl-5-(trifluoromethyl)-1H-pyrazol-4-yl) methyl)thio)-3H-[1,2,3]triazolo[4,5-d]pyrimidin-5-amine, 7-(((1-ethyl-5-(trifluoromethyl)-1H-pyrazol-3-yl)methyl) thio)-3H-[1,2,3]triazolo[4,5-d]pyrimidin-5-amine, 7-(((3-cyclopropyl-1-methyl-1H-pyrazol-5-yl) methyl) thio)-3H-[1,2,3] triazolo[4,5-d]pyrimidin-5-amine, and 7-((2-(pyrrolidin-1-ylmethyl)benzyl)thio)-3H-[1,2,3]triazolo[4,5-d] pyrimidin-5-amine.

5. A pharmaceutical composition, comprising a pharmaceutically acceptable carrier and a compound of claim 1, or a stereoisomer, a tautomer, or a pharmaceutically acceptable salt, a polymorph, or a solvate thereof.

* * * * *